United States Patent
Gao et al.

(10) Patent No.: US 6,858,637 B2
(45) Date of Patent: Feb. 22, 2005

(54) SUBSTITUTED BIARYL AMIDES AS C5A RECEPTOR MODULATORS

(75) Inventors: Yang Gao, Branford, CT (US); Alan J. Hutchison, Madison, CT (US); Wallace C. Pringle, Guilford, CT (US); Andrew Thurkauf, Danbury, CT (US); Taeyoung Yoon, Guilford, CT (US); He Zhao, Branford, CT (US)

(73) Assignee: Neurogen Corporation, Branford, CT (US)

( * ) Notice: Subject to any disclaimer, the term of this patent is extended or adjusted under 35 U.S.C. 154(b) by 54 days.

(21) Appl. No.: 10/401,270

(22) Filed: Mar. 27, 2003

(65) Prior Publication Data

US 2004/0048913 A1 Mar. 11, 2004

Related U.S. Application Data

(60) Provisional application No. 60/368,462, filed on Mar. 28, 2002.

(51) Int. Cl.[7] ............... A61K 31/40; A61K 31/341; A61K 31/4164; C07D 207/32; C07D 307/40
(52) U.S. Cl. ............... 514/385; 514/427; 514/461; 548/338.1; 548/561; 568/132; 549/496
(58) Field of Search ............... 568/132, 138; 514/385, 427, 461; 548/561, 338.1; 549/496

(56) References Cited

U.S. PATENT DOCUMENTS 6,723,743 B1   4/2004   Thurkauf et al. ............ 514/548

2004/0014782 A1   1/2004   Krause

FOREIGN PATENT DOCUMENTS

| EP | 1308438 A1 | 5/2003 |
|---|---|---|
| EP | 1318140 A1 | 6/2003 |
| WO | WO 96/34851 | 11/1996 |
| WO | WO 99/44987 | 9/1999 |
| WO | WO 01/055107 | 8/2001 |
| WO | WO 02/49993 | 6/2002 |
| WO | WO 04/020414 | 3/2004 |

OTHER PUBLICATIONS

Arumugam et al. (2002) *Journal of Surgical Research* 103:260–67.

*Primary Examiner*—Taofiq Solola
(74) *Attorney, Agent, or Firm*—Ann T. Kadlecek; Seth Fidel

(57) ABSTRACT

Substituted biaryl amides of Formula I are provided. Such compounds are ligands that may be used to modulate C5a receptor activity in vivo or in vitro, and are particularly useful in the treatment of conditions associated with pathological C5a receptor activation in humans, domesticated companion animals and livestock animals. Pharmaceutical compositions and methods for using them to treat such disorders are provided, as are methods for using such ligands for receptor localization studies.

Formula I

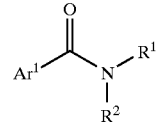

20 Claims, No Drawings

SUBSTITUTED BIARYL AMIDES AS C5A RECEPTOR MODULATORS

This application claims the benefit of Provisional application Ser. No. 60/368,462 filed on Mar. 28, 2002.

Considerable experimental evidence implicates increased levels of C5a in a number of autoimmune diseases and inflammatory and related disorders.

Agents that block the binding of C5a to its receptor other agents, including inverse agonists, which modulate signal transduction associated with C5a-receptor interactions, can inhibit the pathogenic events, including chemotaxis, associated with anaphylatoxin activity contributing to such inflammatory and autoimmune conditions.

SUMMARY OF THE INVENTION

The present invention provides substituted biarylamides of Formula I, below. Such compounds are useful as modulators of C5a receptor and preferably inhibit C5a receptor activation and/or C5a receptor-mediated signal transduction.

Thus, in one aspect the invention provides compounds of Formula I:

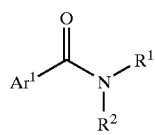

Formula I or a pharmaceutically acceptable salt thereof.

$Ar^1$ is, in Formula I:

i) optionally substituted phenyl having at least one optionally substituted phenyl or optionally substituted heterocyclic substituent attached thereto, or ii) optionally substituted carbocycle having from 2 to about 4 partially unsaturated or aromatic rings, 3 to 8 members in each ring, or iii) optionally substituted heteroaryl.

$R^1$ is optionally substituted cycloalkyl, optionally substituted (cycloalkyl)alkyl, optionally substituted (heteroaryl)alkyl, optionally substituted (aryl)alkyl, optionally substituted aryl, optionally substituted heteroaryl having about 5 to 7 ring atoms and between 1 and 3 ring heteroatoms selected from N, O, and S, or optionally substituted (aryl)alkyl, wherein the aryl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from halogen, alkyl and alkoxy.

$R^2$ is alkyl, cycloalkyl, (cycloalkyl)alkyl, heteroaryl, (heteroaryl)alkyl, aryl, (aryl)alkyl, indanyl, or tetrahydronapthyl, each of which is optionally substituted, or $R^2$ is optionally substituted phenyl($C_0$–$C_2$alkyl), wherein the phenyl portion is fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, alkyl, alkoxy, haloalkyl, and haloalkoxy.

Within certain aspects, compounds as described above exhibit an $IC_{50}$ value no greater than 1 μM, 500 nM, 200 nM, 100 nM, 50 nM, 25 nM, 10 nM or 5 nM in a standard C5a receptor-mediated chemotaxis assay, radioligand binding assay, or calcium mobilization assay. Preferred C5a receptors are mammalian receptors that and may either be cloned, recombinantly expressed receptors or naturally expressed receptors. In certain embodiments the C5a receptors are primate C5a receptors, including human C5a receptors. In certain embodiments, C5a receptor modulators described herein exhibit an affinity for human C5a receptors that is higher than for non-primate C5a receptors; for example in certain embodiments compounds of Formula I exhibit 5-fold or 10-fold greater affinity for human C5a receptors that for most or all non-primate C5a receptors.

Certain aspects of the invention are directed to compounds of Formula I, above, that bind specifically to C5a receptors, and preferably also exhibit an $IC_{50}$ value no greater than 1 μM, 500 nM, 200 nM, 100 nM, 50 nM, 25 nM, 10 nM or 5 nM in a standard C5a receptor-mediated chemotaxis assay, radioligand binding assay, calcium mobilization assay.

The invention further provides, within certain embodiments, compounds of Formula I, that exhibit less than 5% agonist activity in a GTP binding assay.

The present invention further provides, within other aspects, pharmaceutical compositions comprising at least one compound or salt as described above (or a prodrug or hydrate thereof) in combination with a physiologically acceptable carrier or excipient.

The present invention provides, within further aspects, methods for treating a patient suffering from a condition responsive to C5a receptor modulation (e.g., a human or non-human animal, such as a domesticated companion animal or livestock animal). Such methods generally comprise administering to the patient a C5a receptor modulatory amount of at least one compound or salt as described above. For example the invention comprises methods for treating a patient in need of anti-inflammatory treatment or immune treatment with an effective amount of a compound of the invention, e.g. an amount of a compound of the invention sufficient to yield a plasma concentration of the compound (or its active metabolite, if a pro-drug) or high enough to inhibit white blood cell (e.g., neutrophil) chemotaxis in vitro. Treatment of humans, domesticated companion animals (pets) or livestock animals suffering such conditions with an effective amount of a compound of the invention is contemplated by the invention. For treating non-human animals of any particular species, a compound exhibiting high affinity for the C5a receptor of that particular species is preferred.

Within further aspects, methods are provided for inhibiting signal transduction activity of a cellular C5a receptor, comprising contacting a cell expressing a C5a receptor with an effective amount of at least one compound or salt as described above. Such contact may occur in vivo or in vitro. In certain embodiments, the signal transduction activity inhibited is calcium conductance. In other embodiments, the signal transduction activity inhibited is C5a receptor-mediated cellular chemotaxis, and the method comprises contacting mammalian white blood cells with a C5a receptor modulatory amount of a compound or salt as described above.

Methods are further provided, within other aspects, for inhibiting binding of C5a to a C5a receptor. Within certain such aspects, the inhibition takes place in vitro. Such methods comprise contacting a C5a receptor with at least one compound or salt as described above, under conditions and in an amount sufficient to detectably inhibit C5a binding to the receptor. Within other such aspects, the C5a receptor is in a patient. Such methods comprise contacting cells expressing a C5a receptor in a patient with at least one compound or salt as described above at a concentration that would be sufficient to detectably inhibit C5a binding to cells expressing a cloned C5a receptor in vitro.

Compounds as described above are also, in certain aspects, labeled with a detectable marker (e.g., radiolabeled or fluorescein conjugated). The invention provides methods of using appropriately labeled compounds of the invention as probes for localization of receptors, particularly C5a receptors, for example in tissue sections (e.g., via autoradiography) or in vivo (e.g., via positron emission tomography, PET, or single positron emission computed tomography, SPECT, scanning and imaging).

In a separate aspect, the invention provides methods of using compounds of the invention as positive controls in assays for receptor activity, such as radioligand binding, calcium mobilization, and C5a-mediated chemotaxis assays.

The present invention further provides packaged pharmaceutical preparation, comprising: (a) a pharmaceutical composition as described herein in a container; and (b) instructions for using the composition to treat one or more conditions responsive to C5a receptor modulation.

In yet another aspect, the invention provides methods of preparing the compounds disclosed herein, including the intermediates.

These and other aspects of the present invention will become apparent upon reference to the following detailed description.

DETAILED DESCRIPTION OF THE INVENTION

Chemical Description and Terminology

Compounds of the present invention are generally described using standard nomenclature.

The term "substituted biaryl amide," as used herein, encompasses all compounds that satisfy one or more of Formulas I, IA, and II–XIV herein, as well as pharmaceutically acceptable salts, prodrugs and hydrates of such compounds.

Certain compounds described herein contain one or more asymmetric elements such as stereogenic centers, stereogenic axes and the like (e.g., asymmetric carbon atoms) so that the compounds can exist in different stereoisomeric forms. These compounds can be, for example, racemates or optically active forms. For compounds with two or more asymmetric elements, these compounds can additionally be mixtures of diastereomers. Unless otherwise specified all optical isomers and mixtures thereof are encompassed for compounds having asymmetric centers. In addition, compounds with carbon-carbon double bonds may occur in Z- and E- forms, with all isomeric forms of the compounds being included in the present invention unless otherwise specified. Where a compound exists in various tautomeric forms, the invention is not limited to any one of the specific tautomers, but rather encompasses all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C.

Certain compounds are described herein using a general formula, such as Formula I, which includes variables, such as $Ar^1$, $R^1$, and $R^2$. Unless otherwise specified, each variable within such a formula is defined independently of other variables. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

A "substituent," as used herein, refers to a molecular moiety that is covalently bonded to an atom within a molecule of interest. For example, a "ring substituent" may be a moiety such as a halogen, alkyl group, haloalkyl group or other substituent discussed herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a tetrahydropyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Various groups within the compounds and formulae set forth herein are "optionally substituted" including, for example, $R^1$, $R^2$, and $Ar^1$. Optional substitution may also be indicated by the phrase "substituted with from 0 to X substituents," in which X is the maximum number of substituents.

Suitable substituents include, for example, halogen, cyano, amino, hydroxy, nitro, azido, carboxamido, —COOH, $SO_2NH_2$, alkyl (e.g., $C_1$–$C_8$alkyl), alkenyl (e.g., $C_2$–$C_8$alkenyl), alkynyl (e.g., $C_2$–$C_8$alkynyl), alkoxy (e.g., $C_1$–$C_8$alkoxy), alkyl ether (e.g., $C_2$–$C_8$alkyl ether), alkylthio (e.g., $C_1$–$C_8$alkylthio), mono- or di-($C_1$–$C_8$alkyl)amino, haloalkyl (e.g., $C_1$–$C_6$haloalkyl), hydroxyalkyl (e.g., $C_1$–$C_6$hydroxyalkyl), aminoalkyl (e.g., $C_1$–$C_6$aminoalkyl), haloalkoxy (e.g., $C_1$–$C_6$haloalkoxy), alkanoyl (e.g., $C_1$–$C_8$alkanoyl), alkanone (e.g., $C_1$–$C_8$alkanone), alkanoyloxy (e.g., $C_1$–$C_8$alkanoyloxy), alkoxycarbonyl (e.g., $C_1$–$C_8$alkoxycarbonyl), mono- and di-($C_1$–$C_8$alkyl)amino, mono- and di-($C_1$–$C_8$alkyl)amino$C_1$–$C_8$alkyl, mono- and di-($C_1$–$C_8$alkyl)carboxamido, mono- and di-($C_1$–$C_8$alkyl) sulfonamido, alkylsulfinyl (e.g., $C_1$–$C_8$alkylsulfinyl), alkylsulfonyl (e.g., $C_1$–$C_8$alkylsulfonyl), aryl (e.g., phenyl), arylalkyl (e.g., ($C_6$–$C_{18}$aryl)$C_1$–$C_8$alkyl, such as benzyl and phenethyl), aryloxy (e.g., $C_6$–$C_{18}$aryloxy such as phenoxy), arylalkoxy (e.g., ($C_6$–$C_{18}$aryl)$C_1$–$C_8$alkoxy) and/or 3- to 8-membered heterocyclic groups. Certain groups within the formulas provided herein are optionally substituted with from 1 to 3, 1 to 4 or 1 to 5 independently selected substituents.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, and where specified, having the specified number of carbon atoms. Thus, the term $C_1$–$C_6$alkyl, as used herein, indicates an alkyl group having from 1 to 6 carbon atoms. "$C_0$–$C_4$alkyl" refers to a bond or a $C_1$–$C_4$alkyl group. Alkyl groups include groups having from 1 to 8 carbon atoms ($C_1$–$C_8$alkyl), from 1 to 6 carbon atoms ($C_1$–$C_6$alkyl) and from 1 to 4 carbon atoms ($C_1$–$C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. "Aminoalkyl" is an alkyl group as defined herein substituted with one or more —$NH_2$ groups. "Hydroxyalkyl" is a hydroxy group as defined herein substituted with one or more —OH groups.

"Alkenyl" refers to a straight or branched hydrocarbon chain comprising one or more unsaturated carbon-carbon bonds, such as ethenyl and propenyl. Alkenyl groups include $C_2$–$C_8$alkenyl, $C_2$–$C_6$alkenyl and $C_2$–$C_4$alkenyl groups (which have from 2 to 8, 2 to 6 or 2 to 4 carbon atoms, respectively), such as ethenyl, allyl or isopropenyl.

"Alkynyl" refers to straight or branched hydrocarbon chains comprising one or more triple carbon-carbon bonds. Alkynyl groups include $C_2$–$C_8$alkynyl, $C_2$–$C_6$alkynyl and $C_2$–$C_4$alkynyl groups, which have from 2 to 8, 2 to 6 or 2 to 4 carbon atoms, respectively. Alkynyl groups include for example groups such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

The term "alkanoyl" refers to an acyl group in a linear or branched arrangement (e.g., —(C=O)-alkyl). Alkanoyl groups include $C_2$–$C_8$alkanoyl, $C_2$–$C_6$alkanoyl and $C_2$–$C_4$alkanoyl groups, which have from 2 to 8, 2 to 6, or 2 to 4 carbon atoms, respectively. "$C_1$alkanoyl" refers to —(C=O)—H, which (along with $C_2$–$C_8$alkanoyl) is encompassed by the term "$C_1$–$C_8$alkanoyl."

The term, "alkyl ether" refers to a linear or branched ether substituent linked via a carbon-carbon bond. Alkyl ether groups include $C_2$–$C_8$alkyl ether, $C_2$–$C_6$alkyl ether and $C_2$–$C_6$alkyl ether groups, which have 2 to 8, 2 to 6, or 2 to 4 carbon atoms, respectively. By way of example, a $C_2$alkyl ether group has the structure —$CH_2$—O—$CH_3$.

The term "alkoxycarbonyl" refers to an alkoxy group linked via a carbonyl (i.e., a group having the general structure —C(=O)—O-alkyl). Alkoxycarbonyl groups include $C_2$–$C_8$, $C_2$–$C_6$, and $C_2$–$C_4$alkoxycarbonyl groups, which have from 2 to 8, 2 to 6, or 2 to 4 carbon atoms, respectively. "$C_1$alkoxycarbonyl" refers to —C(=O)OH, and is encompassed by "$C_1$–$C_8$alkoxycarbonyl."

"Alkanoyloxy," as used herein, refers to an alkanoyl group linked via an oxygen bridge (i.e., a group having the general structure —O—C(=O)-alkyl). Alkanoyloxy groups include $C_2$–$C_8$, $C_2$–$C_6$, and $C_2$–$C_4$alkanoyloxy groups, which have from 2 to 8, 2 to 6, or 2 to 4 carbon atoms, respectively.

As used herein, the term "alkylthio" refers to an alkyl group attached via a thioether linkage. Alkylthio groups include $C_1$–$C_8$alkylthio, $C_1$–$C_6$alkylthio and $C_1$–$C_4$alkylthio, which have from 1 to 8, 1 to 6 or 1 to 4 carbon atoms, respectively.

"Alkylsulfinyl," as used herein, refers to an alkyl group attached via a sulfinyl linkage. Alkylsulfinyl groups include $C_1$–$C_8$alkylsulfinyl, $C_1$–$C_6$alkylsulfinyl, and $C_1$–$C_4$alkylsulfinyl, which have from 1 to 8, 1 to 6, and 1 to 4 carbon atoms, respectively.

By "alkylsulfonyl," as used herein, is meant an alkyl group attached via a sulfonyl linkage. Alkylsulfonyl groups include $C_1$–$C_8$alkylsulfonyl, $C_1$–$C_6$alkylsulfonyl, and $C_1$–$C_4$alkylsulfonyl, which have from 1 to 8, 1 to 6, and 1 to 4 carbon atoms, respectively.

"Alkylamino" refers to a secondary or tertiary amine having the general structure —NH— alkyl or —N(alkyl)(alkyl), wherein each alkyl may be the same or different. Such groups include, for example, mono- and di-($C_1$–$C_8$alkyl)amino groups, in which each alkyl may be the same or different and may contain from 1 to 8 carbon atoms, as well as mono- and di-($C_1$–$C_6$alkyl)amino groups and mono- and di-($C_1$–$C_4$alkyl)amino groups. Alkylaminoalkyl refers to an alkylamino group linked via an alkyl group (i.e., a group having the general structure -alkyl-NH-alkyl or -alkyl-N(alkyl)(alkyl)). Such groups include, for example, mono- and di-($C_1$–$C_8$alkyl)amino$C_1$–$C_8$alkyl, mono- and di-($C_1$–$C_6$alkyl)amino$C_1$–$C_6$alkyl, and mono- and di-($C_1$–$C_4$alkyl)amino$C_1$–$C_4$alkyl, in which each alkyl may be the same or different.

The term "carboxamido" or "amido" refers to an amide group (i.e., —C(=O)$NH_2$). "Alkylcarboxamido" refers to —NHC(=O)alkyl, preferably —NHC(=O)$C_1$–$C_2$alkyl.

The term "cycloalkyl" refers to hydrocarbon ring groups, having the specified number of carbon atoms, usually from 3 to about 8 ring carbon atoms, or from. Cycloalkyl groups include $C_3$–$C_8$, and $C_3$–$C_7$ cycloalkyl groups, which have from 3 to 8 and 3 to 7 carbon atoms, respectively. Examples of cycloalkyl groups include cyclopropyl, cyclobutyl, cyclopentyl, and cyclohexyl groups, as well as bridged and caged saturated ring groups such as norbornane or adamantane and the like.

In the term "(cycloalkyl)alkyl," "cycloalkyl" and "alkyl" are as defined above, and the point of attachment is on the alkyl group. This term encompasses, but is not limited to, cyclopropylmethyl, cyclohexylmethyl, and cyclohexylethyl.

The term "halogen" indicates fluorine, chlorine, bromine, or iodine.

"Haloalkyl" refers to both branched and straight-chain saturated aliphatic hydrocarbon groups having the specified number of carbon atoms, substituted with I or more halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge.

As used herein, the term "aryl" indicates aromatic groups containing only carbon in the aromatic ring(s). Such aromatic groups may be further substituted with carbon or non-carbon atoms or groups. Typical aryl groups contain 1 to 3 separate or fused rings, at least one of which is aromatic, and from 6 to about 18 ring atoms, without heteroatoms as ring members. Specifically preferred carbocyclic aryl groups include phenyl and napthyl, including 1-naphthyl and 2-naphthyl. When indicated, carbon atoms present within a carbocyclic ring may be optionally substituted with any of variety of ring substituents, as described above, or with specifically listed substituents.

The term "arylalkyl" refers to an aryl group is linked via an alkyl group. Certain arylalkyl groups are ($C_6$–$C_{18}$aryl)$C_1$–$C_8$alkyl groups (i.e., groups in which a 6- to 18-membered aryl group is linked via a $C_1$–$C_8$alkyl group). Such groups include, for example, groups in which phenyl or naphthyl is linked via a bond or $C_1$–$C_8$alkyl, preferably via $C_1$–$C_4$alkyl, such as benzyl, 1-phenyl-ethyl, 1-phenyl-propyl and 2-phenyl-ethyl.

The term "aryloxy" refers to an aryl group linked via a carbonyl (i.e., a group having the general structure —C(=O)—O-aryl). Phenoxy is a representative aryloxy group.

As used herein, the term "heteroaryl" is intended to indicate a stable 5- to 7-membered monocyclic or bicyclic or 7-to 10-membered bicyclic heterocyclic ring which contains at least 1 aromatic ring that contains from 1 to 4 heteroatoms selected from N, O, and S, with remaining ring atoms being carbon. When the total number of S and O atoms in the heteroaryl group exceeds 1, then these heteroatoms are not adjacent to one another. It is preferred that the total number of S and O atoms in the heterocycle is not more than 1, 2, or 3, more typically 1 or 2. It is particularly preferred that the total number of S and O atoms in the aromatic heterocycle is not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl. isoxazolyl, quinolinyl, pyrrolyl, pyrazolyl, and 5,6,7,8-tetrahydroisoquinoline.

The term "heterocyclic group" or "heterocycle" is used to indicate saturated, partially unsaturated, or aromatic groups having 1 or 2 rings, 3 to 8 atoms in each ring and in at least one ring between 1 and 3 heteroatoms selected from N, O, and S. Any nitrogen or sulfur heteroatoms may optionally be oxidized. The heterocyclic group may be attached to its pendant group at any heteroatom or carbon atom that results in a stable structure. The heterocyclic groups described herein may be substituted on a carbon or nitrogen atom if the resulting compound is stable. A nitrogen atom in the heterocycle may optionally be quaternized.

Representative examples of heteroaryl groups and heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;- 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3, 4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"A C5a receptor" is a G-coupled protein receptor that specifically binds C5a protein.

Preferably the C5a receptor is a human C5a receptor such as the protein product of the sequence of the resulting PCR product described by Gerard and Gerard, (1991) *Nature* 349:614–17. The human C5a receptor may also be that described by Boulay (1991) *Biochemistry*, 30(12): 2993–9 (GENBANK Accension No. M62505). Non-primate C5a receptors may be a rat C5a receptor such as a rat C5a receptor, GENBANK Accension Nos. X65862, Y09613, and AB003042, a canine C5a receptor, GENBANK Accension No. X65860, or a guinea pig C5a receptor, GENBANK Accension No. U86103.

A "C5a receptor modulator" is any compound that modulates C5a receptor activation and/or activity (i.e., C5a receptor-mediated signal transduction, as measured using a C5a receptor-mediated chemotaxis, radioligand binding assay, or calcium mobilization assay as provided herein). In certain embodiments, such a modulator may be exhibit an affinity constant or $IC_{50}$ for binding to a C5a receptor of less than 1 micromolar. In other embodiments the a C5a receptor modulator may exhibit an affinity constant or $IC_{50}$ of less than 500 nM, 200 nM, 100 nM, 50 nM, 25 nM, 10 nM or 5 nM in a standard C5a receptor-mediated chemotaxis assay, radioligand binding assay, or calcium mobilization assay. A modulator may be a C5a receptor agonist or antagonist, although, for certain purposes described herein, a modulator preferably inhibits C5a activation resulting from binding of C5a (i.e., the modulator is an antagonist). Preferred antagonists exhibit an antagonist $IC_{50}$ (which is used herein interchangeably with $EC_{50}$) of less than 1 micromolar, preferably less than 100 nanomolar, in an assay of C5a receptor-mediated chemotaxis, radioligand binding, and/or calcium mobilization. In addition, or alternatively, a modulator may act as an inverse agonist of C5a receptor. In certain embodiments, modulators provided herein modulate activation and/or activity of a primate C5a receptor, such as human C5a receptor, which may be a cloned, recombinantly expressed receptor or a naturally expressed receptor. For treating non-human animals of any particular species, a compound exhibiting high affinity for the C5a receptor of that particular species is preferred.

An "inverse agonist" of the C5a receptor is a compound which inhibits the activity of C5a at the C5a receptor, and reduces the activity of the C5a receptor below its basal activity level in the absence of added C5a. Inverse agonists of the C5a receptor may also inhibit binding of C5a to the C5a receptor. The ability of a compound to inhibit the binding of C5a to the C5a receptor may be measured by a binding assay, such as the radioligand binding assay given in Example 19. The basal activity of the C5a receptor may be determined from a GTP binding assay, such as the assay of Example 20. The reduction of C5a activity may also be determined from a GTP binding assay such as the assay of Example 20 or a calcium mobilization assay such as the assay of Example 21.

A "neutral antagonist of the C5a receptor is a compound which inhibits the activity of C5a at the C5a receptor, but does not significantly change the basal activity of the C5a receptor. Neutral antagonists of the C5a receptor may inhibit the binding of C5a to the C5a receptor.

A "partial agonist" of the C5a receptor elevates the activity of the C5a receptor above the basal activity level of the receptor in the absence of C5a, but does not elevate the activity of the C5a receptor to the level brought about by saturating levels of the natural agonist, C5a. Partial agonist compounds may inhibit the binding of C5a to the C5a receptor. Partial agonists of the C5a receptor usually elevate the active of the C5a receptor from 5% to 90% of the activity level brought about by saturated concentrations of the natural agonist, C5a.

A "C5a receptor modulatory amount" of a compound is an amount that is sufficient to yield a plasma concentration of the compound (or its active metabolite, if a prodrug) high enough to detectably alter (modulate) C5a receptor activity and/or ligand binding, when that concentration is used in an in vitro assay. Suitable in vitro assays include the standard in vitro C5a receptor-mediated chemotaxis assay (described in Example 14 herein); C5a receptor-mediated calcium mobilization assay (described in Example 21 herein); and/or radioligand binding assay such as the assay provided in Example 19.

A "therapeutically effective amount" of a compound is an amount that is sufficient to result in a discernible patient benefit. For example, a therapeutically effective amount may reduce symptom severity or frequency. Alternatively, or in addition, a therapeutically effective amount may improve patient outcome and/or prevent or delay disease or symptom onset.

As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4 and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited. A wide variety of synthetic procedures is available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water, an organic solvent, or a mixture of the two; generally, nonaqueous media like ether, ethyl acetate, ethanol, isopropanol or acetonitrile are preferred.

A "prodrug" is a compound that may not fully satisfy the structural requirements of the compounds provided herein, but is modified in vivo, following administration to a patient, to produce a substituted biaryl amide. For example, a prodrug may be an acylated derivative of a compound as provided herein. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, and benzoate derivatives of alcohol and amine functional groups within the compounds provided herein. Preferred prodrugs include acylated derivatives. Prodrugs may be prepared by modifying functional groups present in the compounds in such a way that the modifications are cleaved to the parent compounds. Those of ordinary skill in the art will recognize various synthetic methods that may be employed to prepare prodrugs of the compounds provided herein.

A "patient" is any individual treated with a C5a modulator as provided herein. Patients include humans, as well as other animals such as companion animals (e.g., dogs and cats) and livestock. Patients may be experiencing one or more symptoms of a condition responsive to C5an receptor modulation, or may be free of such symptom(s) (i.e., treatment may be prophylactic).

C5a Receptor Modulators

As noted above, the present invention provides C5a receptor modulators (i.e., compounds that modulate C5a receptor-mediated signal transduction; preferably compounds that also detectably bind to C5a receptor). C5a receptor modulators may be used to modulate C5a receptor activity in a variety of contexts, including in the treatment of patients suffering from diseases or disorders responsive to C5a receptor modulation, such as autoimmune disorders and inflammatory conditions. C5a receptor modulators may also be used within a variety of in vitro assays (e.g., assays for receptor activity), as probes for detection and localization of C5a receptor and as standards in assays of ligand binding and C5a receptor-mediated signal transduction.

C5a receptor modulators provided herein are substituted biaryl amides of Formula I (as well as pharmaceutically acceptable salts and prodrugs thereof) that detectably alter, preferably decrease, C5a receptor activation and/or signal transduction activity at submicromolar concentrations. Such an alteration in C5a receptor activity may be measured using a standard in vitro C5a receptor-mediated chemotaxis assay (Example 14), a C5a receptor-mediated calcium mobilization assay (Example 21) and/or a radioligand binding assay (Example 19). The present invention is based, in part, on the discovery that small molecules of Formula I act as antagonists and/or inverse agonists of C5a receptors.

Thus, an embodiment of the invention is directed to compounds of Formula I:

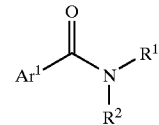

Formula I and the pharmaceutically acceptable salts thereof.

$Ar^1$ is in this embodiment of the invention is
i) optionally substituted phenyl having at least one optionally substituted phenyl or optionally substituted heterocyclic substituent attached thereto, or
ii) optionally substituted 9H-fluorenyl, optionally substituted heteroaryl, or substituted naphthyl.

In certain embodiments it is preferred that $Ar^1$ is an optionally substituted phenyl having at an optionally substituted phenyl or optionally substituted heterocyclic substituent attached thereto at the ortho position or that $Ar^1$ is an optionally substituted naphthyl group having a substituent at the ortho position.

$R^1$, in this embodiment, is optionally substituted cycloalkyl, optionally substituted (cycloalkyl)alkyl, optionally substituted (heteroaryl)alkyl, optionally substituted (aryl)alkyl, optionally substituted aryl, optionally substituted heteroaryl having about 5 to 7 ring atoms and between 1 and 3 ring heteroatoms selected from N, O, and S, or optionally substituted (aryl)alkyl, wherein the aryl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from halogen, alkyl and alkoxy.

$R^2$, in this embodiment, is alkyl, cycloalkyl, (cycloalkyl)alkyl, heteroaryl, (heteroaryl)alkyl, aryl, (aryl)alkyl, indanyl, or tetrahydronapthyl, each of which is optionally substituted, or $R^2$ is optionally substituted phenyl $(C_0–C_2$alkyl), wherein the phenyl portion is fused to a 5 to 7 membered saturated or partially unsaturated ring that (a)

has 0, 1 or 2 ring atoms independently chosen from N, O and S, with remaining ring atoms being carbon, and (b) is substituted with from 0 to 3 substituents independently chosen from halogen, alkyl, alkoxy, haloalkyl, and haloalkoxy.

In certain embodiments the invention includes compounds and pharmaceutically acceptable salts of Formula I wherein: $R^2$ is selected from indanyl, (aryl)alkyl, and cycloalkyl, each of which is optionally substituted.

The invention also includes compounds and pharmaceutically acceptable salts of Formula I in which $Ar^1$ is selected from: i) phenyl having at least one phenyl substituent or heterocyclic substituent attached thereto, wherein each phenyl, phenyl substituent, or heterocyclic substituent is substituted with from 0 to 4 substituents independently selected from halogen, amino, cyano, hydroxy, $C_1$–$C_4$alkyl, $C_1$–$C_4$alkoxy, $C_1$–$C_2$ haloalkyl, $C_1$–$C_2$ haloalkoxy, mono- and di-$C_1$–$C_4$alkylamino, $C_1$–$C_2$ alkylthio, and —NHC(=O) $C_1$–$C_2$ alkyl; ii) naphthyl substituted with from 1 to 3 substituents independently selected from halogen, amino, cyano, hydroxy, $C_1$–$C_4$alkyl, $C_1$–$C_4$alkoxy, $C_1$–$C_2$ haloalkyl, $C_1$–$C_2$ haloalkoxy, mono- and di-$C_1$–$C_4$alkylamino, $C_1$–$C_2$ alkylthio, —NHC(=O) $C_1$–$C_2$ alkyl, optionally substituted phenyl, and optionally substituted thienyl; iii) 9H-fluorenyl substituted with from 0 to 3 substituents independently selected from halogen, amino, cyano, hydroxy, $C_1$–$C_4$alkyl, $C_1$–$C_4$alkoxy, $C_1$–$C_2$ haloalkyl, $C_1$–$C_2$ haloalkoxy, mono- and di-$C_1$–$C_4$alkylamino, $C_1$–$C_2$ alkylthio, —NHC(=O) $C_1$–$C_2$ alkyl; and iv) heteroaryl substituted with from 0 to 3 substituents independently selected from halogen, amino, cyano, hydroxy, $C_1$–$C_4$alkyl, $C_1$–$C_4$alkoxy, $C_1$–$C_2$haloalkyl, $C_1$–$C_2$haloalkoxy, mono- and di-$C_1$–$C_4$alkylamino, $C_1$–$C_2$alkylthio, and —NHC(=O) $C_1$–$C_2$ alkyl.

$R^1$, in this embodiment is: i) (heteroaryl)$C_0$–$C_4$alkyl or (aryl) $C_0$–$C_4$alkyl, each of which is substituted with from 0 to 3 substituents independently selected from halogen, hydroxy, nitro, cyano, $C_1$–$C_4$ alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di($C_1$–$C_2$alkyl)amino, $C_2$–$C_3$alkanoyloxy, $C_1$–$C_3$alkoxycarbonyl, $C_1$-haloalkyl, $C_1$–$C_2$haloalkoxy, thienyl, and phenyl; or ii) (aryl) $C_1$–$C_4$alkyl substituted with from 0 to 5 substituents independently chosen from halogen, hydroxy, $C_1$–$C_2$ alkyl, $C_1$–$C_2$ alkoxy, $C_1$–$C_2$haloalkyl, and $C_1$–$C_2$haloalkoxy, wherein the aryl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from halogen, $C_1$–$C_4$alkyl and $C_1$–$C_4$alkoxy.

$R^2$ is selected from $C_3$–$C_7$ cycloalkyl, ($C_3$–$C_7$cycloalkyl) $C_1$–$C_4$alkyl, (heteroaryl)$C_1$–$C_4$alkyl, (aryl)$C_1$–$C_4$alkyl, and indanyl; each of which is substituted with from 0 to 5 substituents independently selected from halogen, hydroxy, $C_1$–$C_4$ alkyl, $C_1$–$C_4$ alkoxy, $C_1$–$C_4$alkylthio, —NC(=O)$C_1$–$C_2$alkyl, $C_1$–$C_2$haloalkyl, $C_1$–$C_2$haloalkoxy, thienyl, and phenyl. Compounds and salts of this embodiment will be referred to as compounds of Formula IA.

For certain compounds and salts of Formula IA, $R^2$ is selected from: (i) 2-indanyl substituted with from 0 to 2 substituents independently selected from halogen, $C_1$–$C_4$ alkyl, and $C_1$–$C_4$ alkoxy; and (ii) phenyl($C_1$–$C_2$alkyl) substituted with from 0 to 3 substituents independently selected from halogen, hydroxy, $C_1$–$C_4$alkyl, $C_1$–$C_4$alkoxy, $C_1$–$C_4$alkylthio, —NC(=O)$C_1$–$C_2$alkyl, $C_1$–$C_2$haloalkyl, and $C_1$–$C_2$haloalkoxy.

The invention also includes compounds and salts of Formula IA described by general Formula II:

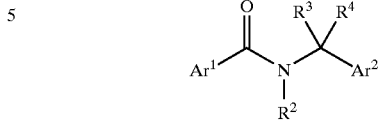

Formula II $Ar^1$, in Formula II, is i) phenyl substituted with from 0 to 4 substituents independently selected from halogen, hydroxy, $C_1$–$C_4$alkyl, $C_1$–$C_4$alkoxy, $C_1$–$C_2$ haloalkyl, $C_1$–$C_2$ haloalkoxy, $C_1$–$C_2$alkylthio, and —NHC(=O) $C_1$–$C_2$ alkyl, and substituted at the 2-position relative to the point of attachment with phenyl, thienyl, imidazolyl, pyrrolyl, pyrazolyl, oxazolyl, naphthyl, thiazolyl, or pyrimidinyl, each of which is substituted with from 0 to 3 substituents independently selected from halogen, amino, cyano, hydroxy, $C_1$–$C_4$alkyl, $C_1$–$C_4$alkoxy, $C_1$–$C_2$ haloalkyl, $C_1$–$C_2$haloalkoxy, mono- and di-$C_1$–$C_4$alkylamino, $C_1$–$C_2$ alkylthio, and —NHC(=O) $C_1$–$C_2$ alkyl, or ii) naphthyl substituted with from 1 to 3 substituents independently selected from (a) halogen, amino, cyano, hydroxy, $C_1$–$C_4$alkyl, $C_1$–$C_4$alkoxy, $C_1$–$C_2$haloalkyl, $C_1$–$C_2$ haloalkoxy, mono- and di-$C_1$–$C_4$alkylamino, $C_1$–$C_2$alkylthio, and —NHC(=O) $C_1$–$C_2$ alkyl, and (b) phenyl and thienyl, each of which is substituted with from 0 to 3 substituents independently chosen from halogen, $C_1$–$C_2$alkyl, $C_1$–$C_2$alkoxy, $C_1$–$C_2$haloalkyl, and $C_1$–$C_2$haloalkoxy; iii) 9H-fluorenyl substituted with from 0 to 3 substituents independently selected from halogen, amino, cyano, hydroxy, $C_1$–$C_4$alkyl, $C_1$–$C_4$alkoxy, $C_1$–$C_2$haloalkyl, $C_1$–$C_2$ haloalkoxy, mono- and di-$C_1$–$C_4$alkylamino, $C_1$–$C_2$alkylthio, and —NHC(=O) $C_1$–$C_2$ alkyl; or iv) heteroaryl substituted with from 0 to 3 substituents independently selected from halogen, amino, cyano, hydroxy, $C_1$–$C_4$alkyl, $C_1$–$C_4$alkoxy, $C_1$–$C_2$haloalkyl, $C_1$–$C_2$ haloalkoxy, mono- and di-$C_1$–$C_4$alkylamino, $C_1$–$C_2$alkylthio, and —NHC(=O) $C_1$–$C_2$ alkyl.

$Ar^2$, in Formula II, is selected from: i) phenyl, ii) naphthyl, iii) a heterocycle having 1 or 2 rings, 3 to 8 atoms in each ring, and 1 to 3 heteroatoms independently selected from N, O, and S; and iv) phenyl fused to a 5- to 7-membered saturated or partially unsaturated ring having 0, 1, or 2 ring atoms independently chosen from N, O, and S, with remaining ring atoms being carbon; wherein each of i), ii), iii), and iv) is substituted with from 0 to 5 substituents independently selected from halogen, hydroxy, —COOH, —CONH$_2$, $C_1$–$C_4$alkyl, $C_1$–$C_4$alkoxy, $C_1$–$C_2$ haloalkyl, $C_1$–$C_2$ haloalkoxy, $C_1$–$C_2$ alkylthio, and —NHC(=O) $C_1$–$C_2$ alkyl.

$R^2$, in Formula II, is selected from $C_3$–$C_7$ cycloalkyl, ($C_3$–$C_7$cycloalkyl)$C_1$–$C_4$alkyl, (heteroaryl)$C_1$–$C_4$alkyl, (aryl)$C_1$–$C_4$alkyl, and indanyl; each of which is substituted with from 0 to 3 substituents independently selected from halogen, hydroxy, $C_1$–$C_4$ alkyl, $C_1$–$C_4$alkoxy, $C_1$–$C_4$alkylthio, —NC(=O)$C_1$–$C_2$alkyl, $C_1$–$C_2$ haloalkyl, $C_1$–$C_2$ haloalkoxy, thienyl, and phenyl.

$R^3$ and $R^4$ are independently selected from hydrogen, $C_1$–$C_4$ alkyl, $C_2$–$C_4$alkenyl, and $C_2$–$C_4$alkynyl.

The invention also includes compounds of Formula IA wherein $R^1$ is i) phenyl($C_1$–$C_2$alkyl) substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio —NC(=O)$C_1$–$C_2$alkyl, mono- and di($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) (phenyl)$C_1$–$C_4$alkyl substituted with from 0 to 3 substituents independently chosen from halogen, hydroxy, $C_1$–$C_2$ alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from halogen, $C_1$–$C_2$alkyl and $C_1$–$C_2$alkoxy.

In other embodiments the invention includes compounds and salts of Formula IA wherein $R^1$ is: i) benzyl substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di-($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) phenyl-CH$_2$-substituted with from 0 to 3 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

The invention includes certain compounds and salts within in this embodiment in which $R^2$ is: i) 2-indanyl substituted with from 0 to 2 substituents independently selected from chloro, fluoro, methyl and methoxy; or ii) benzyl, piperonyl, benzodioxanylmethyl, and benzofuranylmethyl, each of which is substituted with from 0 to 3 substituents independently selected from halogen, hydroxy, $C_1$–$C_2$ alkyl, $C_1$–$C_2$alkoxy, $C_1$–$C_2$haloalkyl, and $C_1$–$C_2$haloalkoxy.

The invention includes certain compounds and salts within in this embodiment in which $R^2$ is 2-indanyl, substituted with from 0 to 2 substituents independently selected from chloro, fluoro, methyl and methoxy.

The invention further includes compounds as salts within this embodiment in which $R^2$ is benzyl substituted with from 0 to 3 substituents independently selected from halogen, hydroxy, $C_1$–$C_4$alkyl, $C_1$–$C_4$alkoxy, $C_1$–$C_4$alkylthio, —NC(=O)$C_1$–$C_2$alkyl, $C_1$–$C_2$haloalkyl, $C_1$–$C_2$haloalkoxy, thienyl, and phenyl.

In other embodiments the invention in pertains to compounds and pharmaceutically acceptable salts of Formula III:

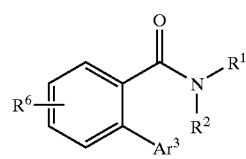

Formula III

Ar$^3$, in these embodiments, is phenyl, pyridyl, furanyl, thienyl, imidazolyl, pyrrolyl, pyrazolyl, oxazolyl, naphthyl, thiazolyl, or pyrimidinyl, each of which is substituted with from 0 to 3 substituents independently selected from halogen, hydroxy, amino, cyano, $C_1$–$C_4$alkyl, $C_1$–$C_4$alkoxy, mono- and di-($C_1$–$C_4$alkyl)amino, $C_1$–$C_2$ haloalkyl, $C_1$–$C_2$haloalkoxy, $C_1$–$C_2$ alkylthio, and —NHC(=O)$C_1$–$C_2$ alkyl.

$R^6$ represents from 0 to 4 substituents independently selected from halogen, hydroxy, $C_1$–$C_4$alkyl, $C_1$–$C_4$alkoxy, $C_1$–$C_2$haloalkyl, $C_1$–$C_2$haloalkoxy, $C_1$–$C_2$alkylthio, and —NHC(=O) $C_1$–$C_2$ alkyl.

$R^1$ and $R^2$ shown in Formula III carry the definitions set forth above for these variables in Formula I or (in certain embodiments) Formula IA.

In other embodiments the invention includes compounds of Formula III, wherein $R^2$ is: i) 2-indanyl, $C_3$–$C_7$cycloalkyl, or $C_3$–$C_7$cycloalkyl($C_1$–$C_4$alkyl), each of which is substituted with from 0 to 2 substituents independently selected from halogen, hydroxy, $C_1$–$C_2$alkyl, $C_1$–$C_2$alkoxy, $C_1$–$C_2$haloalkyl, and $C_1$–$C_2$haloalkoxy; or ii) benzyl, piperonyl, benzodioxanylmethyl, and benzofuranylmethyl, each of which is substituted with from 0 to 3 substituents independently selected from halogen, hydroxy, $C_1$–$C_4$alkyl, $C_1$–$C_4$alkoxy, $C_1$–$C_4$alkylthio, —NC(=O)$C_1$–$C_2$alkyl, $C_1$–$C_2$haloalkyl, $C_1$–$C_2$haloalkoxy, thienyl, and phenyl.

Other embodiments pertain to compounds and salts of Formula III, wherein $R^2$ is: i) 2-indanyl substituted with from 0 to 2 substituents independently selected from chloro, fluoro, methyl and methoxy; or ii) benzyl, piperonyl, benzodioxanylmethyl, or benzofuranylmethyl, each of which is substituted with from 0 to 3 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

Other embodiments of the invention pertain to compounds of Formula III, wherein $R^1$ is: i) benzyl substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) phenyl-CH$_2$-substituted with from 0 to 3 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

The invention includes compounds and salts of Formula III, in which $R^1$ is: (i) benzyl substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di($C_1$–$C_2$alkyl)amino, $C_2$–$C_3$alkanoyloxy, $C_1$–$C_3$alkoxycarbonyl, $C_1$—$C_2$haloalkyl, $C_1$–$C_2$haloalkoxy, thienyl, and phenyl; or (ii) phenyl-CH$_2$- substituted with from 0 to 3 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

Still other embodiments of the invention pertain to compounds and salts of Formula III, in which $R^1$ is: (i) benzyl substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or (ii) phenyl-$CH_2$- substituted with from 0 to 3 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

Further included in the invention are embodiments pertaining to compounds and salts of Formula III, wherein $Ar^3$ is 2-thienyl or 3-thienyl, each of which is substituted with from 0 to 3 substituents independently selected from halogen, hydroxy, amino, cyano, $C_1$–$C_4$alkyl, $C_1$–$C_4$alkoxy, mono- and di-$C_1$–$C_4$alkylamino, $C_1$–$C_2$haloalkyl, $C_1$–$C_2$haloalkoxy, $C_1$–$C_2$ alkylthio, and —NHC(=O)$C_1$–$C_2$ alkyl.

In certain of these embodiments, $R^2$ is further defined as:

(A) i) 2-indanyl, $C_3$–$C_7$cycloalkyl, and $C_3$–$C_7$cycloalkyl ($C_1$–$C_4$alkyl), each of which is substituted with from 0 to 2 substituents independently selected from halogen, hydroxy, $C_1$–$C_2$alkyl, $C_1$–$C_2$alkoxy, $C_1$–$C_2$haloalkyl, and $C_1$–$C_2$haloalkoxy; or ii) benzyl, piperonyl, benzodioxanylmethyl, and benzofuranylmethyl, each of which is substituted with from 0 to 3 substituents independently selected from halogen, hydroxy, $C_1$–$C_4$alkyl, $C_1$–$C_4$alkoxy, $C_1$–$C_4$alkylthio, —NC(=O)$C_1$–$C_2$alkyl, $C_1$–$C_2$haloalkyl, $C_1$–$C_2$haloalkoxy, thienyl, and phenyl; or $R^2$ is (B) $R^2$ is defined as benzyl, piperonyl, benzodioxanylmethyl, or benzofuranylmethyl, each of which is substituted with from 0 to 3 substituents independently chosen from halogen, hydroxy, $C_1$–$C_4$ alkyl, $C_1$–$C_4$ alkoxy, $C_1$–$C_4$alkylthio, —NC(=O)$C_1$–$C_2$alkyl, $C_1$–$C_2$ haloalkyl, $C_1$–$C_2$haloalkoxy, thienyl, and phenyl; or $R^2$ is (C) $R^2$ is defined as 2-indanyl substituted with from 0 to 2 substituents independently chosen from chloro, fluoro, methyl and methoxy.

Additionally in certain embodiments in which $R^2$ is defined as (A), (B), or (C) above:

$R^1$ is: i) benzyl substituted with from 0 to 5 substituents independently selected from halogen, hydroxy, nitro, cyano, —COOH, —$CONH_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di-($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) (phenyl)$C_1$–$C_4$alkyl substituted with from 0 to 3 substituents independently chosen from halogen, hydroxy, $C_1$–$C_2$ alkyl, $C_1$–$C_2$ alkoxy, haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

In other embodiments in which $R^2$ is defined as (A), (B), or (C) above, $R^1$ is: (i) benzyl substituted with from 0 to 5 substituents independently selected from halogen, hydroxy, nitro, cyano, —COOH, —$CONH_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di-($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or (ii) phenyl-$CH_2$- substituted with from 0 to 3 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

In still other embodiments in which $R^2$ is defined as (A), (B), or (C) above:

$R^1$ is benzyl optionally substituted with from 0 to 3 substituents independently selected from halogen, hydroxy, —COOH, —$CONH_2$, $C_1$–$C_4$ alkyl, $C_1$–$C_4$ alkoxy, $C_1$–$C_4$alkylthio, —NC(=O)$C_1$–$C_2$alkyl, mono- or di($C_1$–$C_2$alkyl)amino, $C_1$–$C_2$ haloalkyl, $C_1$–$C_2$haloalkoxy, and phenyl.

The invention also pertains to compounds and salts in which $R^2$ is defined as (A), (B), or (C) above wherein $R^1$ is piperonyl or benzofuranylmethyl, each of which is substituted with from 0 to 3 substituents independently chosen from is chloro, fluoro, methyl, and methoxy.

In separate embodiments the invention pertains to compounds and salts of Formula III, wherein $Ar^3$ is phenyl substituted with from 0 to 3 substituents independently selected from halogen, hydroxy, amino, cyano, $C_1$–$C_4$alkyl, $C_1$–$C_4$alkoxy, mono- and di-$C_1$–$C_4$alkylamino, $C_1$–$C_2$ haloalkyl, $C_1$–$C_2$ haloalkoxy, $C_1$–$C_2$ alkylthio, and —NHC(=O) $C_1$–$C_2$ alkyl.

In certain embodiments of this type:

$R^2$ is:

(D) i) 2-indanyl, $C_3$–$C_7$cycloalkyl, and $C_3$–$C_7$cycloalkyl ($C_1$–$C_4$alkyl), each of which is substituted with from 0 to 2 substituents independently selected from halogen, hydroxy, $C_1$–$C_2$alkyl, $C_1$–$C_2$alkoxy, $C_1$–$C_2$haloalkyl, and $C_1$–$C_2$haloalkoxy; or ii) benzyl, piperonyl, benzodioxanylmethyl, and benzofuranylmethyl, each of which is substituted with from 0 to 3 substituents independently selected from halogen, hydroxy, $C_1$–$C_4$alkyl, $C_1$–$C_4$alkoxy, $C_1$–$C_4$alkylthio, —NC(=O)$C_1$–$C_2$alkyl, $C_1$–$C_2$haloalkyl, $C_1$–$C_2$haloalkoxy, thienyl, and phenyl; or $R^2$ is (E) benzyl, piperonyl, benzodioxanylmethyl, or benzofuranylmethyl, each of which is substituted with from 0 to 3 substituents independently chosen from halogen, hydroxy, $C_1$–$C_4$ alkyl, $C_1$–$C_4$ alkoxy, $C_1$–$C_4$alkylthio, —NC(=O)$C_1$–$C_2$alkyl, $C_1$–$C_2$ haloalkyl, $C_1$–$C_2$haloalkoxy, thienyl and phenyl; or $R^2$ is (F) 2-indanyl substituted with from 0 to 2 substituents independently chosen from chloro, fluoro, methyl and methoxy.

In still other embodiments of this type in which $R^2$ is defined as (D), (E), or (F) above: $R^1$ is: i) benzyl substituted with from 0 to 5 substituents independently selected from halogen, hydroxy, nitro, cyano, —COOH, —$CONH_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di-($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) (phenyl)$C_1$–$C_4$alkyl substituted with from 0 to 3 substituents independently chosen from halogen, hydroxy, $C_1$–$C_2$ alkyl, $C_1$–$C_2$ alkoxy, haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

Other embodiments of this type in which $R^2$ is defined as (D), (E), or (F) above pertain to compounds in which $R^1$ is (i) benzyl substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di-($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or (ii) phenyl-CH$_2$- substituted with from 0 to 3 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

In certain embodiments of this type wherein $R^2$ is defined as (D), (E), or (F); $R^1$ is benzyl optionally substituted with from 0 to 3 substituents independently selected from halogen, hydroxy, $C_1$–$C_4$ alkyl, $C_1$–$C_4$ alkoxy, $C_1$–$C_4$alkylthio, —NC(=O)$C_1$–$C_2$alkyl, mono- or di($C_1$–$C_2$alkyl)amino, $C_1$–$C_2$haloalkyl, $C_1$–$C_2$haloalkoxy, and phenyl.

In still other embodiments of this type the invention includes compounds and salts wherein $R^2$ is defined as (D), (E), or (F); and $R^1$ is piperonyl or benzofuranylmethyl, each of which is substituted with from 0 to 3 substituents independently chosen from is chloro, fluoro, methyl, and methoxy.

In yet another embodiment the invention includes compounds and salts of Formula IV:

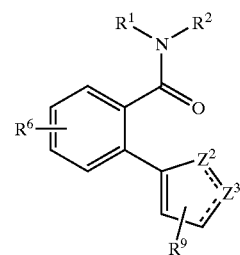

Formula IV

The variables $R^1$ and $R^2$ shown in Formula IV carry the definitions given in Formula IA.

$Z^1$, in this embodiment, is carbon or nitrogen; $Z^2$, $Z^3$, and each occurrence of $Z^4$ are independently selected from $CR^7$, $NR^8$, S, and O such that each S or ring atom, if any, is disposed between two $CR^7$ groups, and p is an integer ranging from 1 to 2.

$R^6$ in Formula IV, represents from 0 to 4 substituents independently selected from halogen, hydroxy, $C_1$–$C_4$alkyl, $C_1$–$C_4$alkoxy, $C_1$–$C_2$haloalkyl, $C_1$–$C_2$haloalkoxy, $C_1$–$C_2$ alkylthio, and —NHC(=O)$C_1$–$C_2$ alkyl.

$R^7$, in Formula IV, is independently selected at each occurrence from hydrogen, halogen, hydroxy, amino, $C_1$–$C_6$alkyl, $C_1$–$C_6$alkoxy, $C_1$–$C_6$haloalkyl, $C_1$–$C_6$haloalkoxy, $C_2$–$C_6$alkenyl, $C_2$$C_6$alkynyl, $C_3$–$C_8$cycloalkyl, mono- and di-($C_1$–$C_6$alkyl)amino, cyano, nitro, and $C_1$–$C_6$alkanoyl.

$R^8$, in Formula IV, is independently selected at each occurrence from hydrogen, $C_1$–$C_6$alkyl, $C_1$–$C_6$haloalkyl, $C_2$–$C_6$alkenyl, $C_2$–$C_6$alkynyl, $C_3$–$C_8$cycloalkyl, and $C_1$–$C_6$alkanoyl.

In certain embodiments the invention pertains to compounds and salts of Formula IV in which the group:

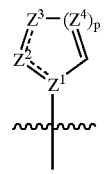

comprises from 1 to 4 nitrogen ring atoms and is substituted with from 0 to 3 substituents independently selected from hydrogen, halogen, hydroxy, amino, $C_1$–$C_6$alkyl, $C_1$–$C_6$alkoxy, $C_1$–$C_6$haloalkyl, $C_1$–$C_6$haloalkoxy, mono-and di-$C_1$–$C_6$alkylamino, and $C_1$–$C_6$ alkanoyl; and p is 1 or 2.

Other embodiments of the invention pertain to compounds and pharmaceutically acceptable salts of Formula V:

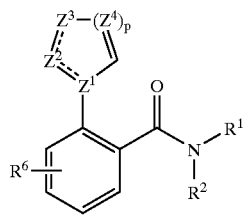

Formula V

The variables $R^1$ and $R^2$ shown in Formula V carry the definitions given in Formula IA.

$R^6$ carries the definition given in Formula IV.

In Formula V one of $Z^2$ or $Z^3$ is sulfur or oxygen; and $R^9$ represents from 0 to 3 substituents independently selected from hydrogen, fluoro, chloro, hydroxy, $C_1$–$C_6$ alkyl, $C_1$–$C_6$alkoxy, $C_1$–$C_2$haloalkyl, and $C_1$–$C_6$haloalkoxy.

Additional embodiments of the invention include compounds and pharmaceutically acceptable salts of Formula VI:

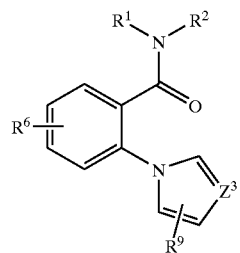

Formula VI

The variables $R^1$ and $R^2$ shown in Formula VI carry the definitions given in Formula IA.

$R^6$ carries the definition given in Formula IV.

In Formula VI, $Z^3$ is nitrogen or $CR^9$; and $R^9$ represents from 0 to 3 substituents independently selected from hydrogen, fluoro, chloro, hydroxy, $C_1$–$C_6$ alkyl, $C_1$–$C_6$alkoxy, $C_1$–$C_2$haloalkyl, and $C_1$–$C_6$haloalkoxy.

Additionally the invention includes compounds and pharmaceutically acceptable salts of Formulae IV–VI wherein $R^2$ is selected from: i) 2-indanyl, $C_3$–$C_7$cycloalkyl, and $C_3$–$C_7$cycloalkyl($C_1$–$C_4$alkyl), each of which is substituted with from 0 to 2 substituents independently selected from halogen, hydroxy, $C_1$–$C_2$alkyl, $C_1$–$C_2$alkoxy, $C_1$–$C_2$haloalkyl, and $C_1$–$C_2$haloalkoxy; and ii) benzyl, piperonyl, benzodioxanylmethyl, and benzofuranylmethyl, each of which is substituted with from 0 to 3 substituents independently selected from halogen, hydroxy, $C_1$–$C_4$ alkyl, $C_1$–$C_4$alkoxy, $C_1$–$C_4$alkylthio, —NC(=O)$C_1$–$C_2$alkyl, $C_1$–$C_2$haloalkyl, $C_1$–$C_2$haloalkoxy, thienyl and phenyl.

The invention also includes compounds and pharmaceutically acceptable salts of Formulae IV–VI wherein $R^2$ is benzyl, piperonyl, benzodioxanylmethyl, or benzofuranylmethyl, each of which is substituted with from 0 to 3 substituents independently chosen from halogen, hydroxy, $C_1$–$C_4$ alkyl, $C_1$–$C_4$alkoxy, $C_1$–$C_4$alkylthio, —NC(=O)$C_1$–$C_2$alkyl, $C_1$–$C_2$haloalkyl, $C_1$–$C_2$haloalkoxy, thienyl, and phenyl.

In other embodiments the invention provides compounds and pharmaceutically acceptable salts of Formulae IV–VI wherein $R^2$ is 2-indanyl substituted with from 0 to 2 substituents independently chosen from chloro, fluoro, methyl and methoxy.

The invention further includes compounds and salts of Formulae IV–VI in which $R^1$ is: i) (phenyl)$C_1$–$C_2$ alkyl substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di-($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) (phenyl)$C_1$–$C_4$alkyl substituted with from 0 to 3 substituents independently chosen from halogen, hydroxy, $C_1$–$C_2$ alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from chloro, fluoro, methyl and methoxy.

The invention includes compounds and salts of Formulae IV–VI in which $R^1$ is: i) benzyl substituted with from 0 to 5 substituents independently selected from halogen, hydroxy, nitro, cyano, —COOH, —CONH$_2$, $C_1$–$C_4$alkyl, $C_2$–$C_4$alkenyl, $C_2$–$C_4$alkynyl, $C_1$–$C_4$alkoxy, $C_1$–$C_4$alkylthio —NC(=O)$C_1$–$C_2$alkyl, mono- and di-($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) phenyl-CH$_2$- substituted with from 0 to 3 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy, wherein the phenyl portion is fused to a 5- to 7-membered saturated or partially unsaturated ring that (a) has 0, 1 or 2 ring atoms independently chosen from N, O and S, with remaining ring atoms being carbon, and (b) is substituted with fro 0 to 2 substituents independently chosen from chloro, fluoro, methyl and methoxy.

In certain embodiments the invention pertains to compounds and salts of Formulae IV–VI in which $R^1$ is benzyl substituted with from 0 to 3 substituents independently selected from halogen, hydroxy, —COOH, —CONH$_2$, $C_1$–$C_4$alkyl, $C_1$–$C_4$ alkoxy, $C_1$–$C_4$alkylthio, —NC(=O)$C_1$–$C_2$alkyl, mono- and di-($C_1$–$C_2$alkyl)amino, $C_1$–$C_2$haloalkyl, $C_1$–$C_2$haloalkoxy, and phenyl.

In other embodiments the invention pertains to compounds and salts of Formulae IV–VI in which $R^1$ is piperonyl or benzofuranylmethyl, each of which is substituted with from 0 to 2 substituents independently chosen from chloro, fluoro, methyl, and methoxy.

Additional embodiments of the invention include compounds and pharmaceutically acceptable salts of Formula VII:

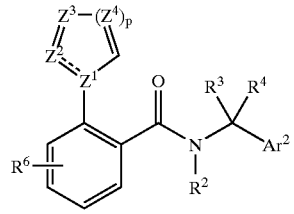

Formula VII

The variables $R^2$, $R^3$ and $R^4$ shown in Formula VII carry the definitions given in Formula II.

$Z^1$, in Formula VII, is carbon or nitrogen;

$Z^2$, $Z^3$, and each occurrence of $Z^4$ are independently selected from $CR^7$, $NR^8$, S, and O such that each S or O ring atom, if any, is disposed between two $CR^7$ groups, p is an integer ranging from 1 to 2; $R^7$ in Formula VII, is independently selected at each occurrence from hydrogen, halogen, hydroxy, amino, $C_1$–$C_6$alkyl, $C_1$–$C_6$alkoxy, $C_1$–$C_6$haloalkyl, $C_1$–$C_6$haloalkoxy, $C_2$–$C_6$alkenyl, $C_2$–$C_6$alkynyl, $C_3$–$C_8$cycloalkyl, mono-and di-($C_1$–$C_6$alkyl)amino, cyano, nitro, and $C_1$–$C_6$alkanoyl; and $R^8$ is independently selected at each occurrence from hydrogen, $C_1$–$C_6$alkyl, $C_1$–$C_6$haloalkyl, $C_2$–$C_6$alkenyl, $C_2$–$C_6$alkynyl, $C_3$–$C_8$cycloalkyl, and $C_1$–$C_6$alkanoyl.

$R^6$, in Formula VII, represents from 0 to 4 substituents independently selected from halogen, hydroxy, $C_1$–$C_4$alkyl, $C_1$–$C_4$alkoxy, $C_1$–$C_2$haloalkyl, $C_1$–$C_2$haloalkoxy, $C_1$–$C_2$ alkylthio, and —NHC(=O)$C_1$–$C_2$ alkyl.

In certain embodiments the invention pertains to compounds of Formula VII in which $Ar^2$ is: i) phenyl; or ii) phenyl fused to a 5- to 7-membered saturated or partially unsaturated ring having 0, 1 or 2 ring atoms independently chosen from N, O and S, with the remaining ring atoms being carbon; wherein each of i) and ii) is substituted with from 0 to 2 substituents independently selected from halogen, hydroxy, —COOH, —CONH$_2$, $C_1$–$C_2$alkyl, $C_1$–$C_2$alkoxy, $C_1$–$C_2$haloalkyl, and $C_1$–$C_2$haloalkoxy.

$R^2$ in this embodiment of the invention is i) 2-indanyl substituted with from 0 to 2 substituents independently selected from chloro, fluoro, methyl and methoxy; or ii) benzyl, piperonyl, benzodioxanylmethyl, or benzofuranylmethyl, each of which is substituted with from 0 to 3 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

$R^3$ and $R^4$ in this embodiment are hydrogen.

The group:

is phenyl or thienyl, each of which is substituted with from 0 to 3 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

$R^6$ in this embodiment represents from 0 to 2 substituents independently selected from halogen, hydroxy, $C_1$–$C_2$alkyl, $C_1$–$C_2$alkoxy, $C_1$–$C_2$haloalkyl and $C_1$–$C_2$haloalkoxy.

Embodiments of the invention pertain to compounds and pharmaceutically acceptable salts of Formula VIII:

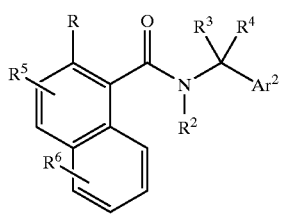

Formula VIII

R, in Formula VIII, is (i) halogen, hydroxy, $C_1$–$C_3$haloalkyl, or $C_1$–$C_3$haloalkoxy, or (ii) $C_1$–$C_6$alkyl, $C_2$–$C_6$alkenyl, $C_2$–$C_6$alkynyl, $C_1$–$C_6$alkoxy, mono- or di-($C_1$–$C_6$alkyl)amino, or $C_3$–$C_7$cycloalkyl($C_0$–$C_4$alkyl), each of which is substituted with from 0 to 4 substituents independently chosen from halogen, hydroxy, amino, oxo, cyano, $C_1$–$C_4$alkyl, $C_1$–$C_4$alkoxy, $C_1$–$C_2$haloalkyl, $C_1$–$C_2$haloalkoxy, and mono- and di($C_1$–$C_4$)alkylamino, (iii) phenyl, or (iv) a heterocyclic ring, having from 4 to 8 ring atoms, and 1 to 3 heteroatoms independently selected from N, O, and S; wherein each of (iii) and (iv) is substituted with from 0 to 3 substituents independently chosen from hydroxy, halogen, amino, cyano, nitro, $C_1$–$C_6$alkyl, $C_1$–$C_6$alkoxy, mono- and di-$C_1$–$C_6$alkylamino, mono- and di-$C_1$–$C_6$alkylamino$C_1$–$C_6$alkyl, $C_1$–$C_6$haloalkyl, $C_1$–$C_6$haloalkoxy, $C_1$–$C_2$ alkylthio, and —NHC(=O)$C_1$–$C_2$ alkyl.

$R^2$, in Formula VIII, is $C_3$–$C_7$ cycloalkyl, ($C_3$–$C_7$cycloalkyl)$C_1$–$C_4$alkyl, (heteroaryl)$C_0$–$C_2$alkyl, (aryl)$C_0$–$C_2$alkyl, or indanyl; each of which is substituted with from 0 to 3 groups independently selected from halogen, hydroxy, $C_1$–$C_4$ alkyl, $C_1$–$C_4$ alkoxy, $C_1$–$C_4$alkylthio, COOH, —NC(=O)$C_1$–$C_2$alkyl, $C_1$–$C_2$ haloalkyl, and $C_1$–$C_2$haloalkoxy; or $R^2$ is (phenyl)$C_0$–$C_2$alkyl, wherein the phenyl portion is fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, hydroxy, cyano, amino, $C_1$–$C_2$alkyl, $C_1$–$C_2$alkoxy, $C_1$–$C_2$ haloalkyl, and $C_1$–$C_2$ haloalkoxy.

$R^3$ and $R^4$ are independently hydrogen, methyl, or ethyl.

$R^5$ and $R^6$ each represent 0 or more substituents independently chosen from halogen, hydroxy, cyano, nitro, amino, $C_1$–$C_6$alkyl, $C_2$–$C_6$alkenyl, $C_1$–$C_6$alkynyl, $C_1$–$C_6$alkoxy, mono- and di-($C_1$–$C_6$)alkylamino, $C_1$–$C_3$haloalkyl, $C_1$–$C_3$haloalkoxy, $C_1$–$C_2$alkylthio, and —NHC(=O)$C_1$–$C_2$alkyl.

$Ar^2$ represents i) phenyl ii) naphthyl iii) a heterocycle having 1 or 2 rings, 3 to 8 atoms in each ring, and 1 to 3 heteroatoms independently selected from N, O, and S; or iv) phenyl fused to a 5- to 7-membered saturated or partially unsaturated ring having 0, 1, or 2 ring atoms independently chosen from N, O, and S, with remaining ring atoms being carbon; wherein each of i), ii), iii), and iv) is substituted with from 0 to 5 substituents independently selected from a) halogen, hydroxy, cyano, amino, —COOH, —CONH$_2$, $C_1$–$C_3$haloalkyl, and $C_1$–$C_3$haloalkoxy, b) $C_1$–$C_6$alkyl, $C_2$–$C_6$alkenyl, $C_2$–$C_6$alkynyl, $C_1$–$C_6$alkoxy, mono- and di-($C_1$–$C_6$alkyl)amino, and ($C_3$–$C_7$cycloalkyl)$C_0$–$C_4$alkyl, each of which is substituted with from 0 to 5 substituents independently chosen from halogen, hydroxy, amino, oxo, cyano, —COOH, $C_1$–$C_4$alkyl, $C_1$–$C_4$alkoxy, mono- and di($C_1$–$C_4$)alkylamino, $C_1$–$C_2$haloalkyl, $C_1$–$C_2$haloalkoxy $C_1$–$C_4$alkylcarboxamide, $C_1$–$C_4$alkylsufinyl, $C_1$–$C_4$alkylsufonyl, $C_1$–$C_4$alkylsufonate, $C_2$–$C_4$alkylester, and $C_1$–$C_4$alkoxycarbonyl, c) $C_1$–$C_4$alkylcarboxamide, $C_1$–$C_4$alkanoyl, $C_1$–$C_4$alkylsufinyl, $C_1$–$C_4$alkylsufonyl, $C_1$–$C_4$alkylsufonate, $C_2$–$C_4$alkylester, $C_1$–$C_4$alkoxycarbonyl, and heterocycloalkyl($C_0$–$C_4$alkyl), and d) (heterocycle)$C_0$–$C_4$alkyl, having 1 or 2 rings, 3 to 8 atoms in each ring, and 1 to 3 heteroatoms independently selected from N, O, and S, substituted with from 0 to 3 groups independently chosen from halogen, hydroxy, nitro, amino, $C_1$–$C_4$alkyl, $C_1$–$C_4$alkoxy, $C_1$–$C_2$ haloalkyl, $C_1$–$C_2$ haloalkoxy, and 5- to 7- membered heterocycloalkyl substituents.

In certain other embodiments the invention pertains to compounds and salts of Formula VIII in which $R^3$, $R^4$, $R^5$, and $R^6$ carry the values given for these variables in Formula VIII.

R is chosen from (i) halogen, hydroxy, $C_1$–$C_3$haloalkyl, and $C_1$–$C_3$haloalkoxy, (ii) $C_1$–$C_6$alkyl, $C_2$–$C_6$alkenyl, $C_2$–$C_6$alkynyl, $C_1$–$C_6$alkyl$_1$O—, $C_1$–$C_6$alkoxy, mono- or di-($C_1$–$C_6$alkylamino, or $C_3$–$C_7$cycloalkyl($C_0$–$C_4$alkyl), each of which is substituted with from 0 to 4 substituents independently chosen from halogen, hydroxy, amino, oxo, cyano, $C_1$–$C_4$alkyl, $C_1$–$C_4$alkoxy, $C_1$–$C_2$haloalkyl, $C_1$–$C_2$haloalkoxy, and mono- and di-($C_1$–$C_4$alkyl)amino, (iii) phenyl, and (iv) pyridinyl, pyrimidinyl, pyrazinyl, thienyl, imidazolyl, pyrazolyl, pyrrolyl, furanyl, oxazolyl, thiazolyl, isoxazolyl, pyrrolidinyl, morpholinyl, piperazinyl, and piperidinyl, wherein each of (iii) and (iv) is substituted with from 0 to 3 substituents independently chosen from hydroxy, halogen, amino, cyano, nitro, $C_1$–$C_6$alkyl, $C_1$–$C_6$alkoxy, mono- and di-$C_1$–$C_6$alkylamino, mono- and di-$C_1$–$C_6$alkylamino$C_1$–$C_6$alkyl, $C_1$–$C_6$haloalkyl, $C_1$–$C_6$haloalkoxy, $C_1$–$C_2$ alkylthio, and —NHC(=O)$C_1$–$C_2$alkyl.

$R^2$, in this embodiment, is $C_3$–$C_7$ cycloalkyl, ($C_3$–$C_7$cycloalkyl)$C_1$–$C_4$alkyl, pyridylmethyl, pyrimidinylmethyl, pyrazinylmethyl, thienylmethyl, quinazolinylmethyl, benzothiazolylmethyl, indolylmethyl, benzimidazolylmethyl, phenyl, benzyl, phenthyl, or indanyl; each of which is substituted with from 0 to 3 groups independently selected from halogen, hydroxy, $C_1$–$C_4$ alkyl, $C_1$–$C_4$ alkoxy, $C_1$–$C_4$alkylthio, —COOH, —NC(=O)$C_1$–$C_2$alkyl, $C_1$–$C_2$ haloalkyl, and $C_1$–$C_2$haloalkoxy; or $R^2$ is benzyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, hydroxy, cyano, amino, $C_1$–$C_2$alkyl, $C_1$–$C_2$alkoxy, $C_1$–$C_2$ haloalkyl, and $C_1$–$C_2$ haloalkoxy.

$Ar^2$ represents i) phenyl, ii) naphthyl, iii) pyridyl, pyrimidinyl, pyrazinyl, pyrazolyl, thienyl, quinazolinyl, benzothiazolyl, indolyl, or benzimidazolyl) phenyl fused to a 5 to 7 membered saturated or partially unsaturated ring that (a) has 0, 1 or 2 ring atoms independently chosen from N, O and S, with remaining ring atoms being carbon, wherein each of i), ii), iii), and iv) is substituted with from 0 to 5 groups independently selected from a) halogen, hydroxy, cyano, amino, —COOH, —CONH$_2$, $C_1$–$C_3$haloalkyl, and $C_1$–$C_3$haloalkoxy, b) $C_1$–$C_6$alkyl, $C_2$–$C_6$alkenyl, $C_2$–$C_6$alkynyl, $C_1$–$C_6$alkoxy, mono- and di-($C_1$–$C_6$alkyl) amino, and ($C_3$–$C_7$cycloalkyl)$C_0$–$C_4$alkyl, each of which is substituted with from 0 to 5 substituents independently chosen from halogen, hydroxy, amino, oxo, cyano, —COOH, $C_1$–$C_4$alkyl, $C_1$–$C_4$alkoxy, mono- and di-($C_1$–$C_4$) alkylamino, $C_1$–$C_2$haloalkyl, $C_1$–$C_2$haloalkoxy $C_1$–$C_4$alkylcarboxamide, $C_1$–$C_4$alkylsufinyl, $C_1$–$C_4$alkylsufonyl, $C_1$–$C_4$alkylsufonate, $C_2$–$C_4$alkylester, and $C_1$–$C_4$alkoxycarbonyl, and c) $C_1$–$C_4$alkylcarboxamide, $C_1$–$C_4$alkanoyl, $C_1$–$C_4$alkylsufinyl, $C_1$–$C_4$alkylsufonyl, $C_1$–$C_4$alkylsufonate, $C_2$–$C_4$alkylester, $C_1$–$C_4$alkoxycarbonyl, and d) (pyrrolidinyl)$C_0$–$C_4$alkyl, (morpholinyl)$C_0$–$C_4$alkyl, (thiomorpholinyl)$C_0$–$C_4$alkyl, (piperazinyl)$C_0$–$C_4$alkyl, and (piperidinyl)$C_0$–$C_4$alkyl, and (thiazolyl)$C_0$–$C_4$alkyl, (piperidyl)$C_0$–$C_4$alkyl, (morpholinyl)$C_0$–$C_4$alkyl, (pyrrolidinyl)$C_0$–$C_4$alkyl, (piperidinyl)$C_0$–$C_4$alkyl, and (piperazinyl)$C_0$–$C_4$alkyl, each of which is substituted with from 0 to 3 groups independently chosen from halogen, hydroxy, nitro, amino, $C_1$–$C_4$alkyl, $C_1$–$C_4$alkoxy, $C_1$–$C_2$ haloalkyl, $C_1$–$C_2$ haloalkoxy, pyrrolidinyl, morpholinyl, thiomorpholinyl, piperazinyl, and piperidinyl.

Still other embodiments of the invention pertain to compounds and salts of Formula IX:

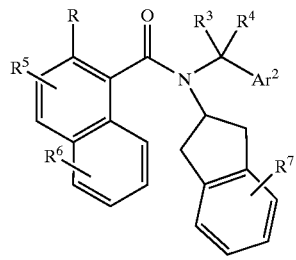

Formula IX

The variables $Ar^2$, R, $R^3$, $R^4$ $R^5$, and $R^6$ carry the definitions set forth above for Formula VIII.

$R^7$ represents from 0 to 3 substituents independently selected from halogen, hydroxy, $C_1$–$C_4$ alkyl, $C_1$–$C_4$ alkoxy, $C_1$–$C_2$ haloalkyl, $C_1$–$C_2$haloalkoxy, and mono- and di-($C_1$–$C_2$alkyl)amino.

In certain embodiments the invention includes compounds and salts of Formula IX in which $R^5$ and $R^6$ are independently chosen from halogen, cyano, nitro, amino, $C_1$–$C_2$alkyl, $C_1$–$C_2$alkoxy, $C_1$–$C_2$haloalkyl, $C_1$–$C_2$haloalkoxy, and mono- and di-($C_1$–$C_2$alkyl)amino.

The invention also pertains to compounds and salts of Formula IX in which R is chosen from (A) (i) halogen and hydroxy, and (ii) $C_1$–$C_6$alkyl and $C_1$–$C_6$alkoxy each of which is substituted with from 0 to 4 substituents independently chosen from halogen, hydroxy, amino, oxo, cyano, $C_1$–$C_4$alkyl, $C_1$–$C_4$alkoxy, $C_1$–$C_2$haloalkyl, $C_1$–$C_2$haloalkoxy, and mono- and di-($C_{1C1}$–$C_4$alkyl)amino, or in other embodiments (B) R is $C_1$–$C_2$alkyl or $C_1$–$C_2$alkoxy, or in still other embodiments (C) R is phenyl, thienyl, or pyridyl, each of which is substituted with from 0 to 3 substituents independently chosen from hydroxy, halogen, amino, cyano, nitro, $C_1$–$C_2$alkyl, $C_1$–$C_2$ alkoxy, $C_1$–$C_2$alkylamino, ($C_1$–$C_2$alkylamino)$C_1$–$C_2$alkyl, $C_1$–$C_2$haloalkyl, and $C_1$–$C_2$haloalkoxy.

The invention also includes compounds and salts of Formula IX in which R is defined as (A), (B), or (C) above and $Ar^2$ is phenyl substituted with from 0 to 5 groups independently selected from halogen, hydroxy, cyano, amino, —COOH, —CONH$_2$, $C_1$–$C_4$alkyl, $C_1$–$C_4$alkoxy, $C_1$–$C_2$haloalkyl, $C_1$–$C_2$haloalkoxy, $C_1$–$C_2$alkylthio, ($C_3$–$C_7$cycloalkyl)$C_0$–$C_2$alkyl, and 5- to 7-membered heterocycloalkyl groups containing 1, 2, or 3 heteroatoms independently selected from N, O, and S.

In other embodiments the invention includes compounds and salts of Formula IX in which R is defined as (A), (B), or (C) above in which $Ar^2$ is phenyl, pyridyl, pyrimidinyl, pyrazinyl, pyrazolyl, thienyl, quinazolinyl, benzothiazolyl, indolyl, or benzimidazolyl, each of which is substituted with from 0 to 5 groups independently selected from halogen, hydroxy, cyano, amino, —COOH, —CONH$_2$, $C_1$–$C_4$alkyl, $C_1$–$C_4$alkoxy, $C_1$–$C_2$haloalkyl, $C_1$–$C_2$haloalkoxy, $C_1$–$C_2$alkylthio, $C_3$–$C_7$cycloalkyl)$C_0$–$C_2$alkyl, pyrrolidinyl, morpholinyl, thiomorpholinyl, piperazinyl, and piperidinyl.

In still other embodiments the invention also includes compounds and salts of Formula IX in which R is defined as (A), (B), or (C) above in which $Ar^2$ is phenyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, hydroxy, cyano, amino, $C_1$–$C_2$alkyl, $C_1$–$C_2$alkoxy, $C_1$–$C_2$haloalkyl, and $C_1$–$C_2$haloalkoxy.

The invention includes a particular class of compounds of Formula IX in which $R^2$ is benzyl or phenethyl, each of which is substituted with from 0 to 3 groups independently selected from halogen, hydroxy, $C_1$–$C_4$ alkyl, $C_1$–$C_4$alkoxy, $C_1$–$C_4$alkylthio, $C_1$–$C_2$haloalkyl, and $C_1$–$C_2$haloalkoxy.

$R_5$ and $R_6$, in certain embodiments of this type, are independently chosen from halogen, cyano, nitro, amino, $C_1$–$C_2$alkyl, $C_1$–$C_2$alkoxy, mono- and di-($C_1$–$C_2$alkyl) amino, $C_1$–$C_2$haloalkyl, and $C_1$–$C_2$haloalkoxy.

R, in still other embodiments of this type, is chosen from (D) (i) halogen and hydroxy, and (ii) $C_1$–$C_6$alkyl and $C_1$–$C_6$alkoxy, each of which is substituted with from 0 to 4 substituents independently chosen from halogen, hydroxy, amino, oxo, cyano, $C_1$–$C_4$alkyl, $C_1$–$C_4$alkoxy, $C_1$–$C_2$haloalkyl, $C_1$–$C_2$haloalkoxy, and mono- and di-($C_1$–$C_4$alkyl)amino, (E) R is $C_1$–$C_2$alkyl or $C_1$–$C_2$alkoxy, and (F) R is phenyl, thienyl, or pyridyl, each of which is substituted with from 0 to 3 substituents independently chosen from hydroxy, halogen, amino, cyano, nitro, $C_1$–$C_2$alkyl, $C_1$–$C_2$ alkoxy, $C_1$–$C_2$alkylamino, ($C_1$–$C_2$alkylamino)$C_1$–$C_2$alkyl, $C_1$–$C_2$haloalkyl, and $C_1$–$C_2$haloalkoxy.

The invention also includes compounds and salts of Formula IX in which R is defined as (D), (E), or (F) above in which $Ar^2$ is phenyl, pyridyl, pyrimidinyl, pyrazinyl, pyrazolyl, thienyl, quinazolinyl, benzothiazolyl, indolyl, or benzimidazolyl, each of which is substituted with from 0 to 5 groups independently selected from halogen, hydroxy, cyano, amino, —COOH, —CONH$_2$, $C_1$–$C_4$alkyl, $C_1$–$C_4$alkoxy, $C_1$–$C_2$ haloalkyl, $C_1$–$C_2$ haloalkoxy, $C_1$–$C_2$ alkylthio, ($C_3$–$C_7$cycloalkyl)$C_0$–$C_2$alkyl, pyrrolidinyl, morpholinyl, thiomorpholinyl, piperazinyl, and piperidinyl.

The further pertains to compounds and salts of Formula IX in which R is defined as (D), (E), or (F) above in which $Ar^2$ is phenyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, hydroxy, cyano, amino, $C_1$–$C_2$alkyl, $C_1$–$C_2$alkoxy, $C_1$–$C_2$ haloalkyl, and $C_1$–$C_2$haloalkoxy.

In still other embodiments the invention pertains to compounds and salts of Formula IX in which R is defined as (D), (E), or (F) above in which $R^2$ is benzyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, hydroxy, cyano, amino, $C_1$–$C_2$alkyl, $C_1$–$C_2$alkoxy, $C_1$–$C_2$ haloalkyl, and $C_1$–$C_2$ haloalkoxy.

In certain embodiments of this type, $R_5$ and $R_6$ are independently chosen from halogen, cyano, nitro, amino, $C_1$–$C_2$alkyl, $C_1$–$C_2$alkoxy, mono- and di-($C_1$–$C_2$alkyl) amino, $C_1$–$C_2$haloalkyl, and $C_1$–$C_2$haloalkoxy.

The invention also pertains to compounds and salts of Formula IX in which R is defined as (D), (E), or (F) above, and the variables $Ar^2$, R, $R^3$, $R^4$ $R^5$, $R^6$ carry the definitions set forth above for Formula VIII.

In certain embodiments of this type $Ar^2$ is phenyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, hydroxy, cyano, amino, $C_1$–$C_2$alkyl, $C_1$–$C_2$alkoxy, $C_1$–$C_2$ haloalkyl, and $C_1$–$C_2$haloalkoxy.

The invention pertains to compounds and salts of Formula II in which $Ar^1$ is heteroaryl substituted substituted with from 0 to 3 substituents independently selected from halogen, amino, cyano, hydroxy, $C_1$–$C_4$alkyl, $C_1$–$C_4$alkoxy, $C_1$–$C_2$ haloalkyl, $C_1$–$C_2$ haloalkoxy, mono- and di-$C_1$–$C_4$alkylamino, $C_1$–$C_2$ alkylthio, —NHC(=O) $C_1$–$C_2$ alkyl. For example, the invention pertains to compounds and salts of Formula II in which $Ar^1$ is indolyl or indazolyl, each of which is substituted with from 0 to 3 substituents independently selected from halogen, amino, cyano, hydroxy, $C_1$–$C_4$alkyl, $C_1$–$C_4$alkoxy, $C_1$–$C_2$ haloalkyl, $C_1$–$C_2$ haloalkoxy, mono- and di-$C_1$–$C_4$alkylamino.

Thus the invention pertains to compounds and salts of Formula II in which Formulae X and XI (which fall within the scope of Formula II):

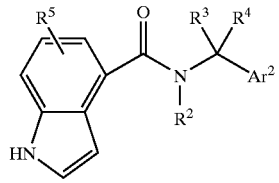

Formula X

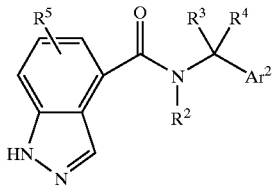

Formula XI where $R^5$ in Formulae X and XI represents from 0 to 3 substituents present on either ring of the bicyclic heteroaryl group independently selected from halogen, amino, cyano, hydroxy, $C_1$–$C_4$alkyl, $C_1$–$C_4$alkoxy, $C_1$–$C_2$ haloalkyl, $C_1$–$C_2$ haloalkoxy, mono- and di-$C_1$–$C_4$alkylamino, $C_1$–$C_2$ alkylthio, —NHC(=O) $C_1$–$C_2$ alkyl.

$R^3$ and $R^4$, in certain embodiments of this type are independently chosen from hydrogen, methyl, and ethyl.

$Ar^2$, for embodiments of this type, is (A) phenyl substituted with from 0 to 5 groups independently selected from halogen, hydroxy, cyano, amino, —COOH, —CONH$_2$, $C_1$–$C_4$alkyl, $C_1$–$C_4$alkoxy, $C_1$–$C_2$haloalkyl, $C_1$–$C_2$haloalkoxy, $C_1$–$C_2$alkylthio, ($C_3$–$C_7$cycloalkyl) $C_0$–$C_2$alkyl, and 5-to 7-membered heterocycloalkyl groups containing 1, 2, or 3 heteroatoms independently selected from N, O, and S; or (B) phenyl, pyridyl, pyrimidinyl, pyrazinyl, pyrazolyl, thienyl, quinazolinyl, benzothiazolyl, indolyl, or benzimidazolyl, each of which is substituted with from 0 to 5 groups independently selected from halogen, hydroxy, cyano, amino, $C_1$–$C_4$alkyl, $C_1$–$C_4$alkoxy, $C_1$–$C_2$ haloalkyl, $C_1$–$C_2$ haloalkoxy, $C_1$–$C_2$ alkylthio, ($C_3$–$C_7$cycloalkyl)$C_0$–$C_2$alkyl, pyrrolidinyl, morpholinyl, thiomorpholinyl, piperazinyl, and piperidinyl; or $Ar^2$ is (C) phenyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, hydroxy, cyano, amino, $C_1$–$C_2$alkyl, $C_1$–$C_2$alkoxy, $C_1$–$C_2$ haloalkyl, and $C_1$–$C_2$haloalkoxy.

In certain of these embodiments $Ar^2$ carrries the definition given in (A), (B), or (C) immediately above and $R^2$ is i) 2-indanyl substituted with from 0 to 2 substituents independently selected from chloro, fluoro, methyl and methoxy; or ii) benzyl, piperonyl, benzodioxanylmethyl, and benzofuranylmethyl, each of which is substituted with from 0 to 3 substituents independently selected from halogen, hydroxy, $C_1$–$C_2$ alkyl, $C_1$–$C_2$alkoxy, $C_1$–$C_2$haloalkyl, and $C_1$–$C_2$haloalkoxy.

In other embodiment of this type, $Ar^2$ carrries the definition given in (A), (B), or (C) immediately above and $R^2$ is 2-indanyl, substituted with from 0 to 2 substituents independently selected from chloro, fluoro, methyl and methoxy.

In still other embodiments within this class $Ar^2$ carrries the definition given in (A), (B), or (C) immediately above, and $R^2$ is benzyl substituted with from 0 to 3 substituents independently selected from halogen, hydroxy, $C_1$–$C_4$alkyl, $C_1$–$C_4$alkoxy, $C_1$–$C_4$alkylthio, —NC(=O)$C_1$–$C_2$alkyl, $C_{1-C2}$haloalkyl, $C_1$–$C_2$haloalkoxy, thienyl, and phenyl.

The invention further pertains to compounds and pharmaceutically acceptable salts of Formula II in which $Ar^1$ is tetrahydronapthyl.

For example the invention pertains to compounds and salts of Formula XII:

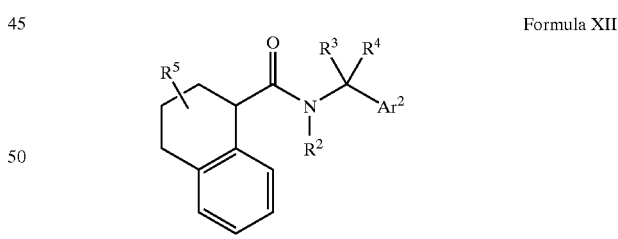

Formula XII wherein, the variables $R^2$, $R^3$, $R^4$, and $Ar^2$ carry the definitions set forth above for compounds of Formula II and $R^5$ in Formula XII represents from 0 to 3 substituents present on either ring of the bicyclic heteroaryl group independently selected from halogen, amino, cyano, hydroxy, $C_1$–$C_4$alkyl, $C_1$–$C_4$alkoxy, $C_1$–$C_2$ haloalkyl, $C_1$–$C_2$ haloalkoxy, mono- and di-$C_1$–$C_4$alkylamino, $C_1$–$C_2$ alkylthio, —NHC(=O) $C_1$–$C_2$ alkyl.

The invention particularly pertains to compounds and salts of Formula XIII and XIV:

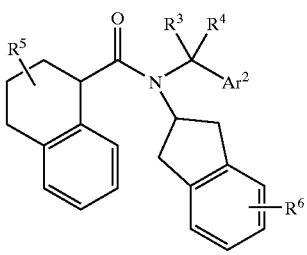

Formula XIII

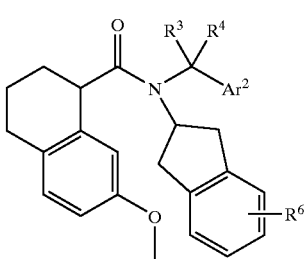

Formula XIV where R⁶ represents from 0 to 3 substituents present on either ring of the indanyl group independently selected from halogen, amino, $C_1$–$C_2$alkyl, and $C_1$–$C_2$alkoxy.

Specific embodiments of the invention include compounds of Formulae XIII and XIV in which R⁵ represents from 0 to 3 substituents present on either ring of indanyl group independently selected from halogen, $C_1$–$C_2$alkyl, and $C_1$–$C_2$alkoxy, R⁶, if present, is methyl, R³ and R⁴ are independently hydrogen, methyl, or ethyl, and Ar², for embodiments of this type, is (D) phenyl substituted with from 0 to 3 groups independently selected from halogen, hydroxy, cyano, amino, —COOH, —CONH₂, $C_1$–$C_4$alkyl, $C_1$–$C_4$alkoxy, $C_1$–$C_2$haloalkyl, and $C_1$–$C_2$haloalkoxy; or Ar² is (E) phenyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, $C_1$–$C_2$alkyl, $C_1$–$C_2$alkoxy, $C_1$–$C_2$ haloalkyl, and $C_1$–$C_2$haloalkoxy; or (F) Ar² is naphthyl or tetrahydronapthyl, each of which may be substituted with from 0 to 4 substituents independently chosen from halogen, hydroxy, amino, $C_1$–$C_4$alkyl, $C_1$–$C_4$alkoxy, $C_1$–$C_2$haloalkyl, and $C_1$–$C_2$haloalkoxy; or (G) Ar² is a group of the Formula:

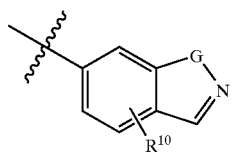

in which G is nitrogen or oxygen and R¹⁰ represents from 0 to 3 substituents present on either ring of two ring system independently selected from halogen, amino, $C_1$–$C_2$alkyl, and $C_1$–$C_2$alkoxy.

In other embodiments the invention pertains to compounds and salts of Formulae XIII and XIV in which R³ and R⁴ are combined to form an oxo group.

Representative substituted biaryl amides provided herein include, but are not limited to, those specifically described in Examples 1–10. It will be apparent that the specific compounds recited therein are representative only, and are not intended to limit the scope of the present invention. Further, as noted above, all compounds of the present invention may be present as a hydrate, free base or a pharmaceutically acceptable acid addition salt.

Certain substituted biaryl amides according to Formulae I, IA, II–XIV have one or more stereogenic centers. In certain embodiment thereof, such compounds may be enantiomers, and may have an enantiomeric excess of at least 55%. Within further embodiments thereof, such compounds have an enantiomeric excess of at least 60%, 70%, 80%, 85%, 90%, 95%, 98%, or 99%. Certain compounds having one or more stereogenic centers have a enantiomeric excess of at least 99%.

Certain substituted biaryl amides according to Formulae I, IA, and II–XIV have two or more stereogenic centers. In certain embodiments thereof, such compounds have a diastereomeric excess of at least 55%. In other embodiments thereof such compounds have a diastereomeric excess of 60%, 70%, 80%, 85%, 90%, 95%, or 98%. Certain compounds having two or more stereogenic centers have a diastereomeric excess of at least 99%.

Substituted biaryl amides provided herein detectably alter (modulate) C5a receptor activity and/or ligand binding, as determined using a standard in vitro C5 receptor-mediated chemotaxis assay (described in Example 14), radioligand binding (described in Example 19), or C5a receptor-mediated calcium mobilization assay (described in Example 21). Preferred compounds exhibit an $IC_{50}$ of about 500 nM or less in such a standard C5a receptor-mediated chemotaxis, radioligand binding, and/or calcium mobilization assay, more preferably an $IC_{50}$ of about 250 nM or less in such an assay, still more preferably an $IC_{50}$ of about 200, 150, 100, 50, 25, 10, or 5 nM or less in such an assay.

Initial characterization of compounds can be conveniently carried out using a C5a receptor binding assay or functional assay, such as set forth in the Examples, and may be expedited by applying such assays in a high throughput screening setting. Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6–9, columns 19–23, as well as for its discussion of complement and inflammation at columns 1–2. Those of skill in the art will recognize that such assays can be readily adapted to the use of cells or animals of different species as deemed appropriate.

In certain embodiments, preferred compounds have favorable pharmacological properties, including oral bioavailability (such that a sub-lethal or preferably a pharmaceutically acceptable oral dose, preferably less than 2 grams, more preferably of less than or equal to one gram, can provide a detectable in vivo effect such as a reduction of C5a-induced neutropenia), ability to inhibit leukocyte chemotaxis at nanomolar concentrations and preferably at sub-nanomolar concentrations, low toxicity (a preferred compound is non-toxic when a C5a receptor-modulatory amount is administered to a subject), minimal side effects (a preferred compound produces side effects comparable to placebo when a C5a receptor-modulatory amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred).

Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography B* 677:1–27. Compound half-life is inversely proportional to the frequency of dosage of a compound required to achieve an effective amount. In vitro half-lives of compounds may be predicted from assays of microsomal half-life as described by Kuhnz and Gieschen (1998) *Drug Metabolism and Disposition* 26:1120–27.

Toxicity and side effects may be assessed using any standard method. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). Toxicity may be also evaluated using the assay detecting an effect on cellular ATP production. Other assays that may be used include bacterial reverse mutation assays, such as an Ames test, as well as standard teratogenicity and tumorogenicity assays. Preferably, administration of compounds provided herein at certain doses (i.e., doses yielding effective in vivo concentrations) does not result in prolongation of heart QT intervals (i.e., as determined by electrocardiography in guinea pigs, minipigs or dogs). When administered daily for five or preferably ten days, such doses also do not cause liver enlargement resulting in an increase of liver to body weight ratio of more than 100%, preferably not more than 75%, and more preferably not more than 50% over matched controls in laboratory rodents (e.g., mice or rats). Such doses also preferably do not cause liver enlargement resulting in an increase of liver to body weight ratio of more than 50%, preferably not more than 25%, and more preferably not more than 10% over matched untreated controls in dogs or other non-rodent mammals.

Certain preferred compounds also do not promote substantial release of liver enzymes (e.g., ALT, LDH or AST) from hepatocytes in vivo. Preferably the above doses do not elevate serum levels of such enzymes by more than 100%, preferably not by more than 75%, and more preferably not by more than 50% over matched untreated controls in vivo in laboratory rodents. Similarly, concentrations (in culture media or other such solutions that are contacted and incubated with cells in vitro) equivalent to two-fold, preferably five-fold, and most preferably ten-fold the minimum in vivo therapeutic concentration do not cause detectable release of any of such liver enzymes from hepatocytes in vitro into culture medium above baseline levels seen in media from untreated cells.

In certain embodiments, preferred compounds exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 4 micromolar. The invention also includes highly specific C5a receptor modulatory compounds that exhibit 200-fold greater affinity for the C5a receptor that for other cellular receptors. Such receptors include neurotransmitter receptors such as alpha- or beta-adrenergic receptors, muscarinic receptors (particularly m1, m2 or m3 receptors), dopamine receptors, and metabotropic glutamate receptors; as well as histamine receptors and cytokine receptors (e.g., interleukin receptors, particularly IL-8 receptors). Such receptors may also include $GABA_A$ receptors, bioactive peptide receptors (other than C5a receptors and C3a receptors, including NPY or VIP receptors), neurokinin receptors, bradykinin receptors, and hormone receptors (e.g., CRF receptors, thyrotropin releasing hormone receptors or melanin-concentrating hormone receptors). Compounds that act with high specificity generally exhibit fewer undesirable side effects.

Within certain embodiments, modulators provided herein do not bind detectably to receptors that do not mediate inflammatory responses, such as GABA receptors, MCH receptors, NPY receptors, dopamine receptors, serotonin receptors and VR1 receptors, with high or even moderate affinity. In addition, or alternatively, certain preferred C5a receptor modulators exhibit an affinity for C5a receptor that is substantially higher than for receptors that do not mediate inflammatory responses (e.g., at least five times higher, at least ten times higher or at least 100 times higher). Assays for evaluating binding to receptors that do not mediate inflammatory responses include, for example, those described in U.S. Pat. No. 6,310,212, which is incorporated herein by reference for its disclosure of a $GABA_A$ receptor binding assays in Examples 14, columns 16–17, in U.S. patent application Ser. No. 10/152,189 which is incorporated herein by reference for its disclosure of an MCH receptor binding assay in Example 2, pages 104–105, in U.S. Pat. No. 6,362,186, which is incorporated herein by reference for its disclosure of CRF1 and NPY receptor binding assays in Examples 19, columns 45–46, in U.S. Pat. No. 6,355,644, which is incorporated herein by reference for its disclosure of a dopamine receptor binding assay at column 10, and in U.S. Pat. No. 6,482,611, which is incorporated herein by reference for its disclosure of VR1 receptor binding assays in Examples 4–5, column 14. It will be apparent that the C5a receptor modulators provided herein may, but need not, bind to one or more other receptors known to mediate inflammatory responses, such as C3a receptors and/or $A_3$ receptors.

Certain preferred compounds are C5a receptor antagonists that do not possess significant (e.g., greater than 5%) agonist activity in any of the C5a receptor-mediated functional assays discussed herein. Specifically, this undesired agonist activity can be evaluated, for example, in the GTP binding assay of Example 20, by measuring small molecule mediated GTP binding in the absence of the natural agonist, C5a. Similarly, in a calcium mobilization assay (e.g., that of Example 21) a small molecule compound can be directly assayed for the ability of the compound to stimulate calcium levels in the absence of the natural agonist, C5a. The preferred extent of C5a agonist activity exhibited by compounds provided herein is less than 10%, 5% or 2% of the response elicited by the natural agonist, C5a.

Additionally, preferred C5a receptor modulators do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity. Preferred C5a receptor modulators also do not exhibit cytotoxicity in vitro or in vivo, are not clastogenic (e.g., as determined using a mouse erythrocyte precursor cell micronucleus assay, an Ames micronucleus assay, a spiral micronucleus assay or the like) and do not induce sister chromatid exchange (e.g., in Chinese hamster ovary cells). Also preferred are C5a receptor modulators that inhibit the occurrence of C5a-induced oxidative burst (OB) in inflammatory cells (e.g., neutrophil) as can be conveniently determined using an in vitro neutrophil OB assay.

For detection purposes, compounds provided herein may be isotopically-labeled or radiolabeled. Accordingly, compounds recited in Formula I (or any other formula specifically recited herein) may have one or more atoms replaced by an atom of the same element having an atomic mass or mass number different from the atomic mass or mass number usually found in nature. Examples of isotopes that can be present in compounds provided herein include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. In addition, substitution with heavy isotopes such as deuterium (i.e., $^2$H) can afford certain therapeutic advantages resulting from greater metabolic stability, for example increased in vivo half-life or reduced dosage requirements and, hence, may be preferred in some circumstances.

Methods of Use

C5a modulators provided herein may be used as agonists or (preferably) antagonists of C5a receptors in a variety of contexts, both in vitro and in vivo. Within certain aspects, C5a antagonists may be used to inhibit the binding of C5a receptor ligand (e.g., C5a) to C5a receptor in vitro or in vivo. In general, such methods comprise the step of contacting a C5a receptor with a sufficient amount of one or more substituted biaryl amides as provided herein, in the presence of C5a receptor ligand in aqueous solution and under conditions otherwise suitable for binding of the ligand to C5a receptor. The C5a receptor may be present in suspension (e.g., in an isolated membrane or cell preparation), or in a cultured or isolated cell. Within certain embodiments, the C5a receptor is expressed by a cell present in a patient, and the aqueous solution is a body fluid. In general, the amount of C5a receptor modulator contacted with the receptor should yield a concentration in the aqueous solution sufficient to inhibit C5a binding to C5a receptor in vitro as measured, for example, using a radioligand binding assay as described in Example 19, a calcium mobilization assay as described in Example 21, or a chemotaxis assay as described in Example 14. Preferably the concentration is sufficient to inhibit chemotaxis of white blood cells in an in vitro chemotaxis assay, so that the levels of chemotaxis observed in a control assay (e.g., one to which a compound provided herein has not been added) are significantly higher (significance here measured as $p \leq 0.05$ using a conventional parametric statistical analysis method such as a student's T-test) than the levels observed in an assay to which a compound as described herein has been added.

Also provided herein are methods for modulating, preferably inhibiting, the signal-transducing activity of a C5a receptor. Such modulation may be achieved by contacting a C5a receptor (either in vitro or in vivo) with an effective amount of one or more C5a receptor modulators provided herein under conditions suitable for binding of the modulator(s) to the receptor. The receptor may be present in solution or suspension, in a cultured or isolated cell preparation or within a patient. Modulation of signal transducing activity may be assessed by detecting an effect on calcium ion conductance (also referred to as calcium mobilization or flux) or by detecting an effect on C5a receptor-mediated cellular chemotaxis. In general, an effective amount of C5a modulator(s) is an amount sufficient to yield a concentration (in an aqueous solution that is in contact with the receptor) that is sufficient to modulate C5a receptor signal transducing activity in vitro within a calcium mobilization assay as described in Example 21 or C5a receptor-mediated cellular chemotaxis within an assay as described in Example 14. C5a receptor modulator(s) provided herein are preferably administered to a patient (e.g., a human) orally or topically, and are present within at least one body fluid of the animal while modulating C5a receptor signal-transducing activity.

The present invention further provides methods for treating patients suffering from conditions responsive to C5a receptor modulation. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to C5a receptor modulation" if modulation of C5a receptor activity results reduction of inappropriate activity of a C5a receptor, regardless of the amount of C5a receptor ligand present locally and/or in alleviation of the condition or a symptom thereof. Patients may include primates (especially humans), domesticated companion animals (such as dogs, cats, horses) and livestock (such as cattle, pigs, sheep), with dosages as described herein.

Conditions that are responsive to C5a receptor modulation include the following:

Autoimmune disorders—e.g., rheumatoid arthritis, systemic lupus erythematosus (and associated glomerulonephritis), psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, and hyperacute rejection of transplanted organs.

Inflammatory disorders and related conditions—e.g., neutropenia, sepsis, septic shock, Alzheimer's disease, stroke, inflammation associated with severe burns, lung injury, and ischemia-reperfusion injury, osteoarthritis, as well as acute (adult) respiratory distress syndrome (ARDS), systemic inflammatory response syndrome (SIRS), and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease.

In a further aspect, C5a receptor modulators may be used to perfuse a donor organ prior to transplantation of the organ into a recipient patient. Such perfusion is preferably carried out using a solution (e.g., pharmaceutical composition) comprising a concentration of the modulator that is sufficient to inhibit C5a receptor-mediated effects in vitro and/or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Treatment methods provided herein include in general administration to a patient an effective amount of one or more compounds of the invention. Suitable patients include those patients suffering from or susceptible to (i.e., prophylactic treatment) a disorder or disease identified herein. Typical patients for treatment in accordance with the invention include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. The effective amount may be an amount sufficient to modulate C5a receptor activity and/ or an amount sufficient to reduce or alleviate the symptoms presented by the patient. Preferably, the amount administered is sufficient to yield a plasma concentration of the compound (or its active metabolite, if a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

As noted above, compounds and compositions provided herein are useful as inhibitors of C5a receptor-mediated chemotaxis (e.g., they may be used as standards in assays of such chemotaxis). Accordingly, methods are provided herein for inhibiting C5a receptor-mediated cellular chemotaxis, preferably leukocyte (e.g., neutrophil) chemotaxis. Such methods comprise contacting white blood cells (particularly primate white blood cells, especially human white blood cells) with one or more compounds provided herein. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound as described herein has been added.

Within separate aspects, the present invention provides a variety of non-pharmaceutical in vitro and in vivo uses for the compounds provided herein. For example, such compounds may be labeled and used as probes for the detection and localization of C5a receptor (in samples such as cell preparations or tissue sections, preparations or fractions thereof). Compounds may also be used as positive controls in assays for C5a receptor activity, as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

Pharmaceutical Preparations

The present invention also provides pharmaceutical compositions comprising one or more C5a receptor modulators provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an active compound prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, oral, nasal, rectal or parenteral administration. In certain embodiments, compositions in a form suitable for oral use are preferred. Such forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

Compositions intended for oral use may be prepared according to any method known to the art for the manufacture of pharmaceutical compositions and may contain one or more agents sweetening agents, flavoring agents, coloring agent, and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, such as glycerol, propylene glycol, sorbitol, or sucrose. Such formulations may also comprise one or more demulcents, preservatives, flavoring agents, and/or coloring agents.

Oily suspensions may be formulated by suspending the active ingredients in a vegetable oil (e.g., arachis oil, olive oil, sesame oil, or coconut oil) or in a mineral oil such as liquid paraffin. The oily suspensions may contain a thickening agent such as beeswax, hard paraffin, or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin), or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate), and condensation products of partial esters derived from fatty acids and hexitol with ethylene oxide (e.g., polyoxyethylene sorbitan monoleate). An emulsion may also comprise one or more sweetening and/or flavoring agents.

The pharmaceutical composition may be prepared as a sterile injectable aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectable compositions, and adjuvants such as local anesthetics, preservatives and/or buffering agents can be dissolved in the vehicle.

C5a receptor modulators may also be administered in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

C5a receptor modulators provided herein are generally administered in an amount that achieves a concentration in a body fluid (e.g., blood, plasma, serum, CSF, synovial fluid, lymph, cellular interstitial fluid, tears or urine) that is sufficient to detectably inhibit the binding of C5a to C5a receptor when assayed in vitro. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5–20 fold higher than intravenous doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions may be packaged for treating conditions responsive to C5a receptor modulation (e.g., rheumatoid arthritis, psoriasis, cardiovascular disease, reperfusion injury, bronchial asthma, Alzheimer's disease, stroke, myocardial infarction, atherosclerosis, ischemic heart disease or ischemia-reperfusion injury). Packaged pharmaceutical compositions may include a container holding a effective amount of at least one C5a receptor modulator as described herein and instructions (e.g., labeling) indicating that the contained composition is to be used for treating a condition responsive to C5a receptor modulation in the patient Preparation of Compounds Substituted biaryl amides provided herein may generally be prepared using standard synthetic methods. In general, starting materials are commercially available from suppliers such as Sigma-Aldrich Corp. (St. Louis, Mo.), or may be synthesized from commercially available precursors using established protocols. By way of example, a synthetic route similar to that shown the following Schemes may be used, together with synthetic methods known in the art of synthetic organic chemistry, or variations thereon as appreciated by those skilled in the art. Each variable in the following Schemes, such as an "R" or "Ar," refers to any group consistent with the description of the compounds provided herein. An individual skilled in the art may find modifications of one or several of the synthetic steps described herein without diverting significantly from the overall synthetic scheme.

The preparation of ortho biarylamides described herein may be carried out via a series of chemical transformations similar to those displayed graphically in Scheme I.

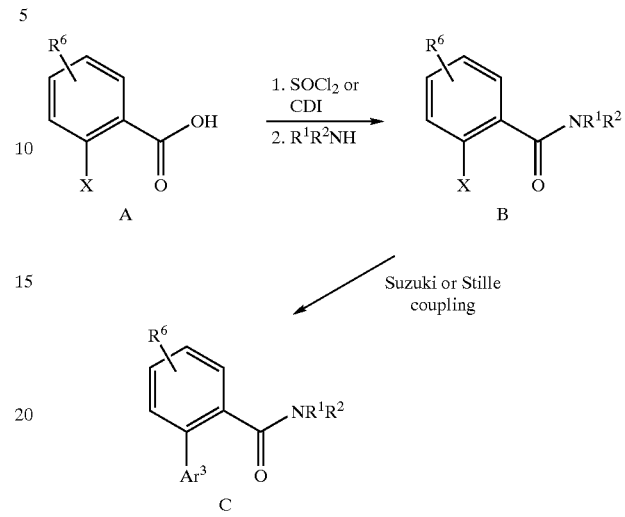

Scheme 1.
Preparation of Ortho Biarylamides

As shown, the synthetic route begins with a benzoic acid of general structure A possessing a group X at the ortho position. This X group may be iodine, bromine, chlorine, sulfonate ester or polyfluoroalkylsulfonate ester. The benzoic acid may also be substituted by up to four independently chosen substituents represented by the variables $R^6$. Examples of suitable substituents include, but are not limited to, chlorine, fluorine, cyano, $C_1$–$C_6$ straight or branched chain alkyl, $C_1$–$C_6$ straight or branched chain alkoxy, trifluoromethyl, trifluoromethoxy, nitro, amino, mono- and di-alkylamino, sulfonamido, mono- and di-alkylsulfonamido, alkylthio (e.g., methylthio), alkylsulfoxide, alkylsulfone, acetyl, acetoxy, alkoxycarbonyl (—C=OO(alkyl)), or dialkylaminocarbonyl (—C=ON (alkyl)$_2$). Additionally, two adjacent $R^6$ groups may be taken together with a chain of from 3 to 5 methylene carbons to form an alkyl ring of from five to seven carbons fused to the benzoic acid moiety. Additionally, two adjacent $R^6$ groups may be taken together with an alkyloxy chain, for example —OCH$_2$O— or —OCH$_2$CH$_2$O—, to form an oxygen-containing moiety (in this example methylenedioxy or ethylenedioxy, respectively) fused to the benzoic acid.

The benzoic acid is then activated by conversion to an acid chloride with thionyl chloride, oxalyl chloride or the like. Alternatively, it may be activated by treatment with carbonyldiimidazole or a similar agent. The activated benzoic acid is then treated with an appropriate secondary amine in the presence of base to provide a tertiary amide of general structure B.

Amide B is then converted to the biaryl structure C through the use of aryl coupling reactions know in the chemical literature. Examples of such reactions are the Stille reaction where an aryl trialkyltin reagent is coupled to an appropriate aryl in the presence of a catalyst such as palladium or nickel; or a Suzuki reaction where an arylboronic acid is coupled to an appropriate aryl in the presence of a nickel or palladium catalyst in the presence of base.

The group "$Ar^3$" of General structure C may be a phenyl, naphthyl or other aromatic group, and may be optionally substituted with up to five additional independently chosen substituents (e.g., hydrogen, halogen, cyano, $C_1$–$C_6$ straight or branched chain alkyl, $C_1$–$C_6$ straight or branched chain alkoxy, trifluoromethyl, trifluoromethoxy, nitro, amino, mono- or di-alkyl amino, sulfonamido, mono or dialkylsulfonamido, alkylthio (e.g., methylthio), alkylsulfoxide, alkylsulfone, acetyl, acetoxy, hydroxycarbonyl (—COOH), alkoxycarbonyl (—C=OO(alkyl)), aminocarbonyl (—CONH$_2$), monoalkylaminocarbonyl (—C=ONH(alkyl)), dialkylaminocarbonyl (—C=ON(alkyl)$_2$), methylenedioxy, or ethylenedioxy).

The Ar$^3$ of General Structure C may also represent a heteroaryl group such as 1- or 2-thienyl or 1- or 2- furanyl. Such a heteroaryl group which may be additionally substituted by up to three independently chosen substituents, such as halogen, cyano, C$_1$–C$_6$ straight or branched chain alkyl, C$_1$–C$_6$ straight or branched chain alkoxy, trifluoromethyl, trifluoromethoxy, mono- or di-alkyl amino, sulfonamido, mono- and di-alkylsulfonamido, alkylthio (e.g., methylthio), alkylsulfoxide, alkylsulfone, acetyl, acetoxy, hydroxycarbonyl, —COOH, alkoxycarbonyl, aminocarbonyl, monoalkylaminocarbonyl, or dialkylaminocarbonyl.

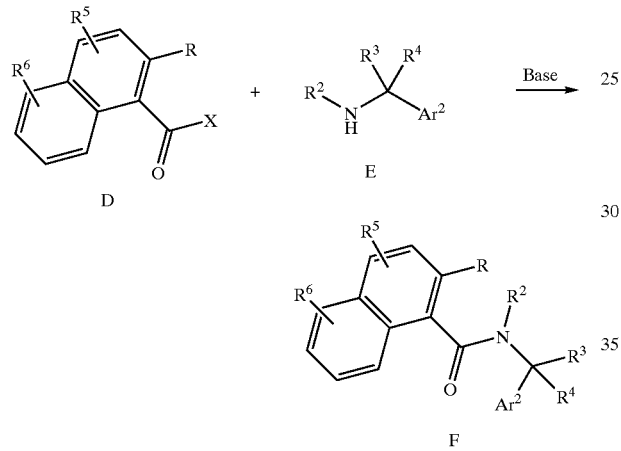

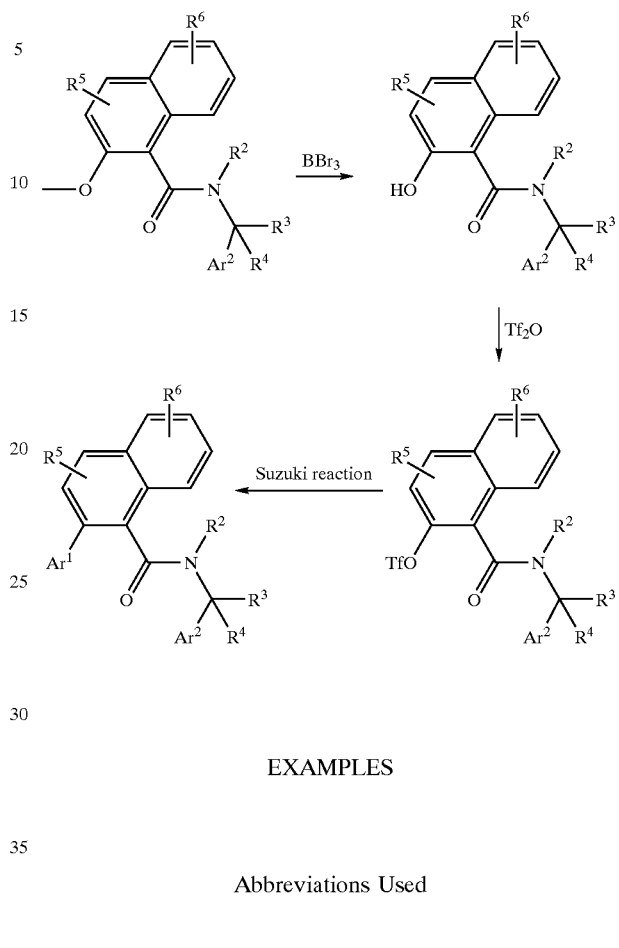

Within Scheme 2 the variable X is a halogen, preferably chlorine or bromine.

As shown in Scheme 2, an appropriately substituted 1-napthoyl halide (D) is condensed with an appropriately substituted amine (E) in the presence of a base, such as triethylamine or potassium carbonate or the like, to provide compounds of Formula F, Compounds of general formulas D and E can be prepared by one of several methods described in the chemical literature.

Certain compounds provided herein contain one or more stereogenic centers. In these situations, single enantiomers (i.e., optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The following Examples are offered by way of illustration and not by way of limitation. Unless otherwise specified all reagents and solvent are of standard commercial grade and are used without further purification, or are readily prepared from such materials by routine methods. Those skilled in the art of organic synthesis will recognize that starting materials and reaction conditions may be varied to achieve the desired end product.

EXAMPLES

Abbreviations Used

The following abbreviations are used in Examples 1 to 5.

PyBroP  Bromotris(pyrrolidino)phosphonium hexafluorophosphate

| | |
|---|---|
| DMA | dimethylacetamide |
| NMM | N-methylmorpholine |
| t-BuOH | tert-butanol |
| CDI | 1,1'-carbonyl diimidazole |
| DMF | dimethylformamide |
| SOCl$_2$ | thionyl chloride |
| Pd(PPh$_3$)$_4$ | tetrakis(triphenylphosphine) palladium (0) |
| Na$_2$SO$_4$ | sodium sulfate |
| CDCl$_3$ | deuterochloroform |
| THF | tetrahydrofuran |
| $^1$H NMR | proton nuclear magnetic resonance |
| SiO$_2$ | silica |
| SPE | solid phase extraction |
| LCMS | liquid chromatography/mass spectrometry |
| HPLC | high pressure liquid chromatography |
| MHz | megahertz |
| Hz | hertz |
| MS | mass spectrometry |
| m/z | mass/charge ratio |
| (M + 1) | mass + 1 |

Example 1

Preparation of 4'-Trifluoromethyl-biphenyl-2-carboxylic Acid Benzo[1,3]dioxol-5-ylmethyl-benzyl-amide

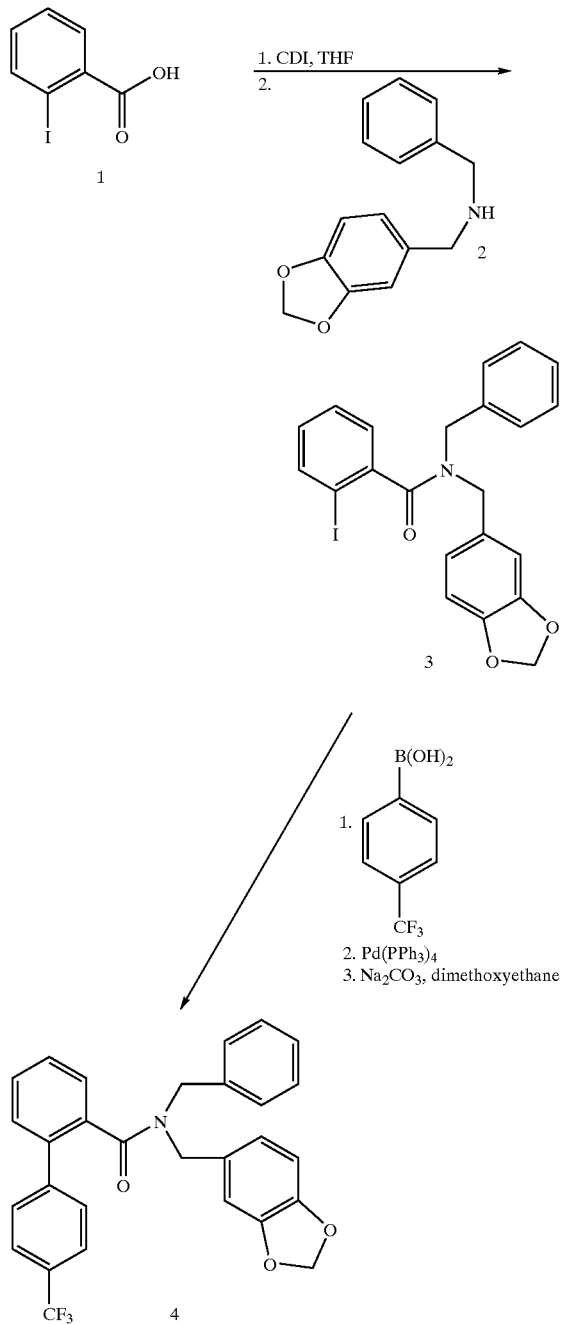

1,1'-carbonyldiimidazole (175 mg) is added to a solution of 2-iodobenzoic acid (248 mg, 1 mmol) (1) in tetrahydrofuran (THF, 5 ml). The resulting mixture is stirred overnight at room temperature. A solution of N-3,4-methylenedioxybenzyl-N-benzylamine (241 mg, 1 equivalent) (2) in THF (2 mL) is added and the resulting solution is stirred for 1 hour, quenched with water, and extracted with diethyl ether. The organic extracts are dried ($Na_2SO_4$) and concentrated. The residual material is taken up in dimethoxyethane (10 mL) and a catalytic amount (20 mg) of tetrakis(triphenylphosphine)palladium(0) is added. The resulting mixture is stirred under an argon atmosphere for 10 minutes and solid 4-trifluoromethyllphenylboronic acid (150 mg) is added in one portion. A second phase of 1N aqueous $Na_2SO_4$ is added and the mixture is warmed to 80° C. for 6 hours under an argon atmosphere. The solution is cooled, diluted with water and ethyl acetate and filtered through a pad of celite. The organic phase is dried over sodium sulfate and concentrated. Purification on silica eluting with 20% ethyl acetate in hexane provides the desired biphenylamide product (4). The proton NMR displays a doubled pattern commonly observed for amides which possess some rotational restriction about the amide nitrogen at room temperature. The ratio of the rotomers is approximately equal. $^1$H NMR (CDCl$_3$) 3.50 and 3.62 (two doublets, J=X Hz, 1H), 3.72 and 3.83 (two doublets, J=X Hz, 1H), 4.10 and 4.18 (two doublets, J=X Hz, 1H), 5.09 and 5.16 (two doublets, J=x Hz, 1H), 5.95 (d, J=X Hz, 2H, OCH$_2$O), 6.30 (m, 1.5 H), 6.46 (d, J=1 Hz, 0.5 Hz), 6.60 and 6.66 (two doublets, J=X Hz, 1H), 6.80 (bd, J=X Hz, 1H), 6.86 (m, 1H), 7.16–7.62 (m, 11 H).

Example 2

Preparation of 3-Methyl-biphenyl-2-carboxylic Acid Benzyl-indan-2-yl-amide

Step A.

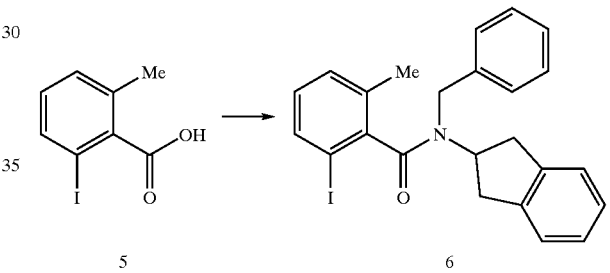

Thionyl chloride (1 ml) is added to a suspension of 2-Iodo-6-methyl benzoic acid (665 mg, 2.5 mmol) (5) in 10 ml of toluene. The mixture is stirred at 80° C. for 2 hours; the solvent and the remaining thionyl chloride are then evaporated. The residue is dissolved in 5 ml of anhydrous tetrahydrofuran and added to a solution of benzyl-indan-2-yl-amine (557 mg, 2.5 mmol) in 10 ml of tetrahydrofuran containing 506 mg of triethylamine at 0° C. The resulting mixture is stirred at room temperature overnight, diluted with 20 ml of ethyl acetate, washed with water and brine, and dried over sodium sulfate. Concentration and purification by silica gel chromatography affords compound 6. MS (+VE) m/z 467 (M+1).

Step B.

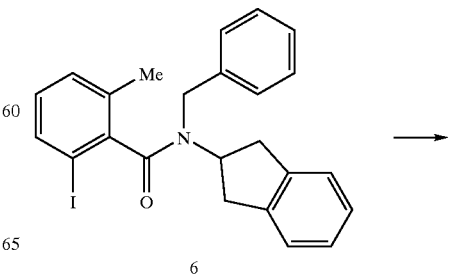

-continued

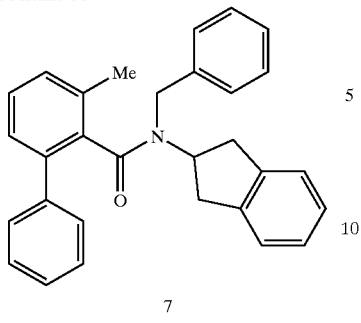

Aqueous sodium carbonate solution (1.0 ml of 2.0N) and a solution of phenyl boronic acid (40 mg, 0.325 mmol) in 0.3 ml ethanol is added to a solution of compound 6 (117 mg, 0,25 mmol) and Pd(PPh$_3$)$_4$ (13 mg, 0.015 mmol) in 2 ml of toluene under N$_2$. The resulting mixture is stirred at 80° C. overnight. The mixture is cooled to room temperature, diluted with 20 ml of ethyl acetate, washed with water and brine, dried, and concentrated. The crude product is purified by silica gel chromatography to give 97 mg of product 7. $^1$H NMR (400 MHz, CDCl$_3$) δ 7.40–7.60 (4H, m), 6.90–7.30 (11H, m), 6.75 (2H, m), 4.75 (1H, d, J=15.5 Hz), 4.39 (1H, m), 4.30 (1H, d, J=15.6 Hz), 2.80 (2H, m), 2.44 (3H, s), 2.28 (2H, m). MS (+VE) m/z 418 (M$^+$).

Example 3

Preparation of N-benzyl-N-(2-methyl-benzyl)-2-pyrrol-1-yl-benzamide

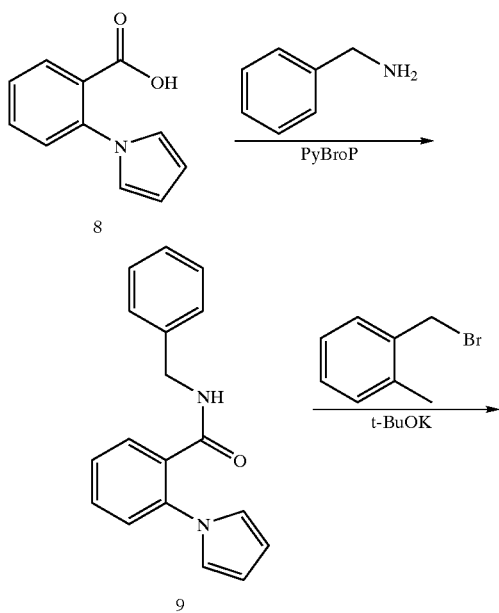

-continued

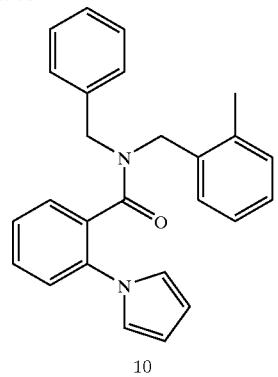

2-Pyrrol-1-yl-benzoic acid (3.7 mg; 1 equiv.) (8) is dissolved to 0.2 M in DMA containing triethylamine (5% v/v). A solution of benzylamine (0.2 M in toluene containing NMM (5% v/v); 0.10 ml; 1 equiv.) is added followed by a solution of PyBroP (0.2 M in THF; 0.12 ml; 1.2 equiv.). The resulting solution, containing intermediate (9), is shaken at room temperature for 3 hours. A solution of 2-methylbenzyl bromide (0.2 M in toluene; 0.15 ml; 1.5 equiv.) is then added followed by potassium tert-butoxide (0.5 M in THF/t-BuOH (1:1, v/v); 0.16 ml; 4 equiv.). The solution is heated to 50° C. for 3 hours, and then cooled to room temperature and treated with saturated ammonium chloride (0.35 ml). The reaction is extracted with isopropyl ether (0.5 ml), and the upper organic layer is deposited on a silica gel SPE cartridge (0.5 g SiO$_2$). The cartridge is eluted with 25% ethyl acetate in hexanes (4 ml), and the eluted solution is concentrated under reduced pressure, to provide the desired product (10). LCMS: target mass 381.20 (M+H)$^+$; observed mass 381.15 (M+H)$^+$; 92% spectrum purity.

Example 4

Preparation of N-indan-2-yl-N-(3-methyl-benzyl)-2-pyrrol-1-yl-benzamide

2-Pyrrol-1-yl-benzoic acid (3.7 mg; 1 equiv.) (8) is dissolved to 0.2 M in DMA containing triethylamine (5% v/v). A solution of indan-2-ylamine (0.2 M in toluene containing NMM (5% v/v); 0.10 ml; 1 equiv.) is added followed by a solution of PyBroP (0.2 M in THF; 0.12 ml; 1.2 equiv.). The resulting solution is shaken at room temperature for 3 hours. The solution is then treated with potassium tert-butoxide (0.5 M in THF/t-BuOH (1:1, v/v); 0.15 ml; 3.75 equiv.) and 3-methylbenzyl bromide (0.2 M in Toluene; 0.125 ml; 1.25 equiv.). The reaction is shaken at room temperature for 20 minutes, and then retreated with 3-methylbenzyl bromide (0.2 M in Toluene; 0.05 ml; 0.5 equiv.) and potassium tert-butoxide (0.5 M in THF/t-BuOH (1:1, v/v); 0.025 ml; 1.25 equiv.). The reaction is shaken again at room temperature for 20 minutes and retreated with 3-methylbenzyl bromide (0.2 M in toluene; 0.05 ml; 0.5 equiv.) and potassium tert-butoxide (0.5 M in THF/t-BuOH (1:1, v/v); 0.025 ml; 1.25 equiv.). The reaction is then heated to 50° C. for 2 hours, then cooled to room temperature, and treated with saturated ammonium chloride (0.5 ml). The reaction is extracted with isopropyl ether (0.5 ml), and the upper organic layer is deposited on a silica gel SPE cartridge (0.5 g SiO$_2$). The cartridge is eluted with 25% ethyl acetate in hexanes (4 ml), and the eluted solution is concentrated under reduced pressure, to yield the title compound (11). LCMS:

target mass 407.21 (M+H)+; observed mass 407.25 (M+H)+; 92% spectrum purity.

Example 5

Preparation of 2-methoxy-naphthalene-1-carboxylic Acid Benzyl-indan-2-yl-amide

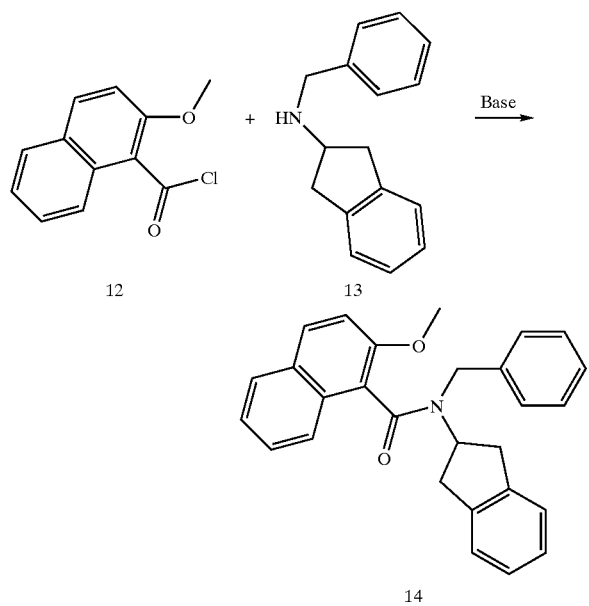

2-Methoxynapthoic acid (202 mg, 1 mmol) is dissolved in thionyl chloride (1 ml). The resulting solution is refluxed for 2 hours. The thionyl chloride is evaporated on a rotary evaporator, the residue taken up in toluene (5 ml), and reconcentrated. The resulting 2-methoxynapthoyl chloride (12) is dissolved in dry tetrahydrofuran (5 ml) containing triethylamine (278 microliters, 2 mmol) and dimethylaminopyridine (DMAP, 20 mg). A solution of N-benzyl-N-indan-2-ylamine (179 mg, 0.8 mmol) (13) is added to the 2-methoxynapthoyl chloride solution and the resulting solution is stirred overnight. A solution of sodium bicarbonate (3N, 5 ml) is added and the mixture extracted with ethyl acetate (3×20 ml). The organic extracts are then washed with water and brine, dried over sodium sulfate, and concentrated. The crude product is purified by silica gel chromatography to provide the desired compound (14) as an oil. LC-MS 408 (M+1), $^1$H NMR (CDCl$_3$) 7.87 (d, J=2 Hz, 1H), 7.72–7.82 (m, 2H), 7.52 (t, J=2 Hz, 1H), 7.45 (d, 2Hz, 1H), 6.96–7.40 (m, 10H), 5.22 (d, J=4 Hz, 1H), 4.65 (d, J=4 Hz, 1H), 4.6 (t, J=2 Hz, 1H), 4.04 (s, 3H, OMe), 2.95–3.08 (m, 2H), 2.86 (dd, J=4, 2 Hz, 1H), 2.68 (J=4, 2 Hz, 1H) ppm. A minor amide rotational isomer with the methoxy group at 3.87 ppm is also observable.

Example 6

Preparation of 2-(5-methyl-thiophen-2-yl)-naphthalene-1-carboxylic Acid Indan-2-yl-(2-fluoro-benzyl)-amide

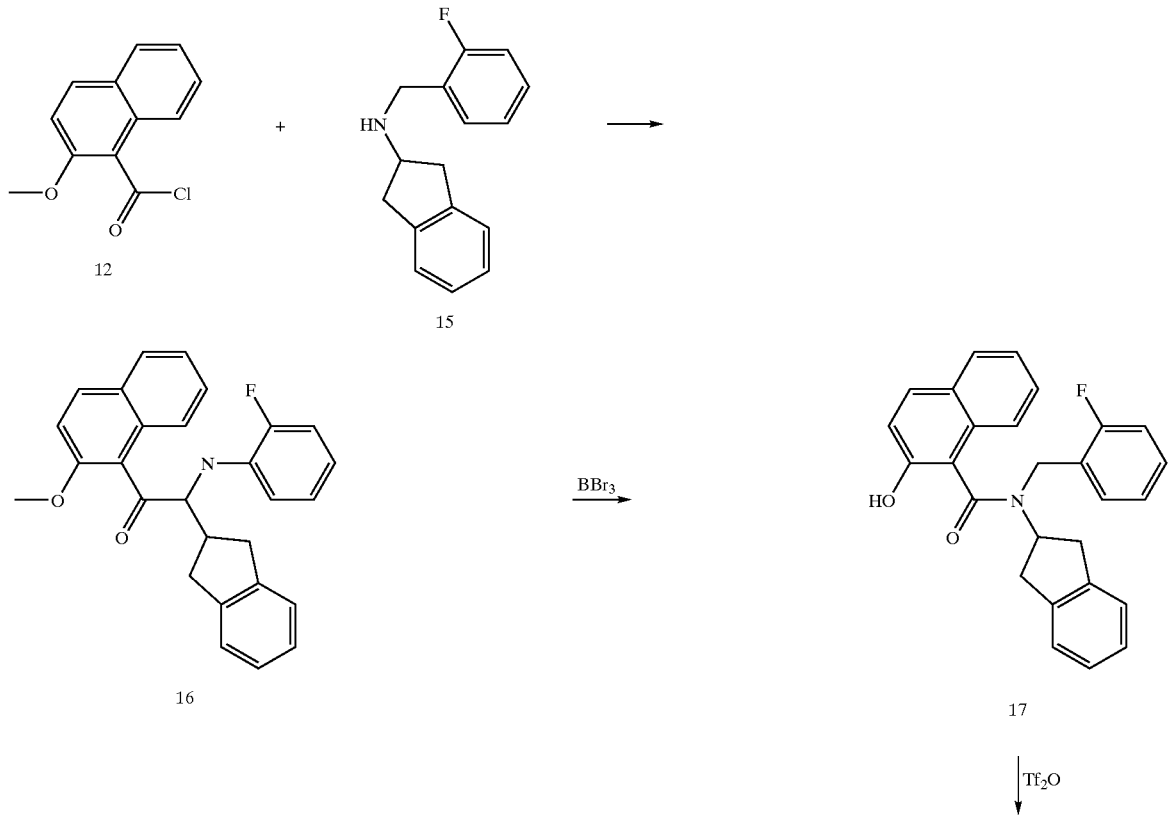

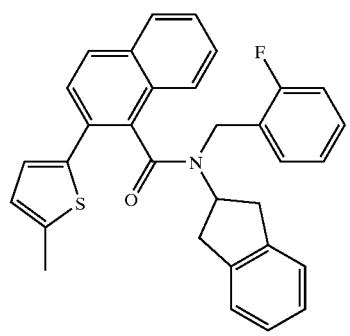

20

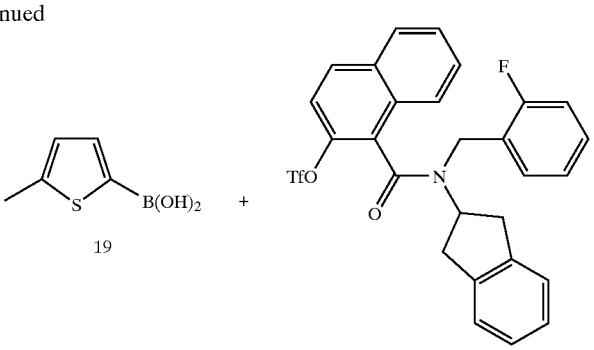

18

Step A. Synthesis of 2-methoxy-naphthalene-1-carboxylic Acid Indan-2-yl-(2-fluoro-benzyl)-amide

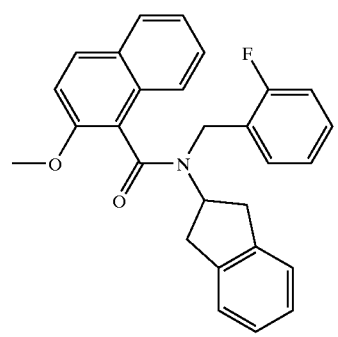

The above compound (16) is prepared in by the method described in Example 5.

Step B. Synthesis of 2-Hydroxy-naphthalene-1-carboxylic Acid Indan-2-yl-(2-fluoro-benzyl)-amide

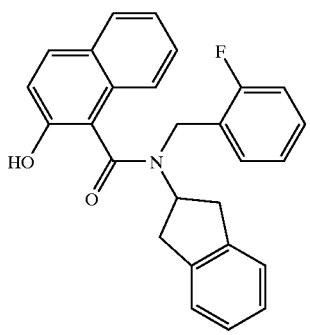

Boron tribromide (1N in dichloromethane, 1 mL) is added at −78° C. under nitrogen to a solution of 2-methoxy-naphthalene-1-carboxylic acid indan-2-yl-(2-fluoro-benzyl)-amide (16) (421 mg; 1 mmol) in anhydrous dichloromethane (5 mL). The mixture is then stirred at room temperature overnight. After cooling to 0° C., water is added to quench the reaction. The organic phase is separated, dried over anhydrous sodium sulfate, and concentrated. The residue is purified by column chromatography to provide the title compound (17) as a white solid (365 mg, 90%). LC-MS [MH+] 412; $^1$H NMR (300 MHz, CDCl3) δ 8.66 (s, 1H); 7.73 (t, J=7.2 Hz, 2H), 7.53–7.48 (m, 1H), 7.42–7.32 (, m, 2H), 7.20 (m, 2H), 7.09–6.98 (m, 5H), 6.81 (d, J=9.0 Hz, 1H), 4.74 (m, 2H), 3.16 (m, 1H), 2.98–2.20 (m, 2H), 2.36 (s, 2H).

Step C. Synthesis of Trifluoro-methanesulfonic Acid 1-[Indan-2-yl-(2-fluoro-benzyl)-carbamoyl]-napthalen-2-yl Ester Trifluoromethanesulfonic acid anhydrous (0.27 mL, 1.6 mmol) is added dropwise in 10 minutes to a solution of 2-hydroxy-naphthalene-1-carboxylic acid indan-2-yl-(2-fluoro-benzyl)-amide (17) (323 mg, 0.8 mmol) in anhydrous pyridine (5 mL) at 0° C. under nitrogen. The mixture is stirred at room temperature overnight and concentrated under reduced pressure. The residue (18) is dried in vacuo and used for the next step without further purification.

Step D. Synthesis of 2-(5-methyl-thiophen-2-yl)-naphthalene-1-carboxylic Acid Indan-2-yl-(2-fluoro-benzyl)-amide A mixture of the trifluoromethanesulfonic acid 1-[indan-2-yl-(2-fluoro-benzyl)-carbamoyl]-naphthalen-2-yl ester (18), 5-methyl-2-thiophene boronic acid (19) (142 mg, 1 mmol) and Pd(PPh)$_4$ ( 50 mg) in 2 mL of 1 N sodium carbonate and toluene (v/v=1/1) in seal tube under nitrogen was heated at 90° C. for 16 hours. After cooling to room temperature, the organic phase is separated and the aqueous phase extracted with ethyl acetate. The combined organic phases are washed with 1N HCl, saturated sodium bicarbonate and brine, dried over anhydrous sodium sulfate, and concentrated. The residue is purified by silica gel column chromatography to yield the desired product (20) (72 mg, 19% in two steps). LC-MS [MH+] 492.

Example 7

Synthesis of 1,5-Dimethyl-1H-indole-4-carboxylic Acid Indan-2-yl-(4-methyl-benzyl)-amide

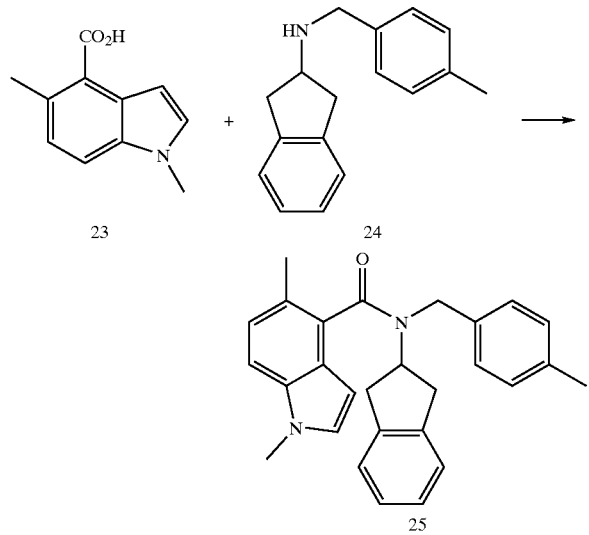

Step A. Synthesis of 4-bromo-5-methylindole

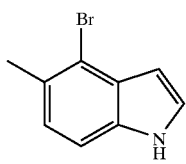

Fuming nitric acid (>90% yellow fuming $HNO_3$) is slowly added to a solution of 2-bromo-m-xylene (20 g, 150 mmol) in acetic acid (100 ml) cooled in an ice bath (above freezing point). The resulting mixture is allowed to warm to room temperature, stirred for 1 hour, and heated at 80° C. for 2 hours or until the reaction is shown to be complete by GC/MS analysis following micro-scale base work-up. The reaction mixture is cooled to room temperature and poured into ice/water with stirring. The resulting yellow precipitates are collected by suction filtration and air dried to obtain 2,6-dimethyl-3-nitrobromobenzene.

Bredereck's reagent (tert-butoxybis(dimethylamino) methane—16 g, 91 mmol) is added at room temperature to a solution of 2,6-dimethyl-3-nitrobromobenzene (20 g, 87 mmol) in anhydrous DMF (120 ml). The reaction mixture is heated at 120–125° C. under $N_2$ for 5 hours or until starting material is mostly consumed according to TLC. The reaction mixture is allowed to cool to room temperature, poured into water (300 ml), and extracted with dichloromethane (100 ml×3). The combined extracts are dried over anhydrous sodium sulfate, filtered, and concentrated to obtain a mixture of enamines as a dark brown oil. This material is carried on to the next step without purification. The crude mixture is dissolved in acetic acid/water (250 ml of 4:1), cooled to 0° C. and treated with zinc dust (57 g, 870 mmol) added slowly in portions. After complete addition, the reaction mixture is heated at 110° C. for 4 h. Zinc is removed by filtration through a celite pad and the filtrate is extracted with dichloromethane (100 ml×3). The combined extracts are dried over anhydrous sodium sulfate, concentrated and purified by flash chromatography on silica get (EtOAc/Hexane 1:20) to obtain 4-bromo-5-methylindole (5.3 g) (21) as a light purple oil.

Step B. Preparation of 4-bromo-1,5-dimethyl-1H-indole

A solution of 4-bromo-5-methylindole (3.55 g, 16.9 mmol) (21) in 10 ml of anhydrous DMF is added to a suspension of sodium hydride (1.01 g, 60% in mineral oil, 25.3 mmol, 1.5 eq.) in 10 ml of DMF under nitrogen at 0° C. The resulting mixture is stirred at 0° C. for 30 minutes, and then warmed to room temperature. After stirring at room temperature for an additional 2 hours, the reaction mixture is cooled to 0° C. Iodomethane (2.40 g, 18.6 mmol, 1.1 eq.) is added dropwise, the mixture is stirred at 0° C. for 2 hours, and then is warmed to 50° C. and stirred for an additional 2 hours. The reaction mixture is poured into 100 ml of ice-water, extracted with ethyl acetate (30 ml×3), washed with water and brine dried over anhydrous sodium sulfate. The solvent is evaporated and the product (22) is taken to dryness under high vacuum to give 3.75 g of pure compound. $^1H$ NMR (400 MHz, $CDCl_3$) δ 7.17 (1H, d, J=8.4 Hz), 7.08 (1H, d, J=8.4 Hz), 7.05 (1H, 4, J=3.2 Hz), 650 (1H, dd, J=0.4, 2.8 Hz), 3.77 (3H, 3), 2.51 (3H, s); MS (+VE) m/z 224 ($M^+$).

Step C. Preparation of 1,5-Dimethyl-1H-indole-4-carboxylic Acid

N-BuLi (1.6 M in hexane, 3.45 ml, 5.5 mmol, 1.1 eq.) is added under nitrogen to a solution of 4-bromo-1,5-dimethylindole (1.12 g, 5 mmol) (22) in 20 ml anhydrous tetrahydrofuran cooled to −78° C. The resulting solution is stirred at −78° C. for 30 minutes and then quenched by introducing anhydrous carbon dioxide gas. The reaction mixture is raised to room temperature slowly, 20 ml of water is added into the flask and the tetrahydrofuran is evaporated at reduced pressure. The resulting aqueous solution is adjusted to pH 5–6 with 1.0 N hydrochloric acid. The product is extracted with ethyl acetate (25 ml×3), washed with water and brine, dried over anhydrous sodium sulfate, concentrated, and taken to dryness under high vacuum to give 927 mg of 1,5-Dimethyl-1H-indole-4-carboxylic acid (23). $^1H$ NMR (400 MHz, $CDCl_3$) δ 7.40 (1H, d, J=8.4 Hz), 7.15 (1H, d, J=3.2 Hz), 7.12 (1H, d, J=8.0Hz), 7.02 (1H, dd, J=0.8, 3.2 Hz), 3.81 (3H, s), 2.75 3H, s). MS (+VE) m/z 190 ($M^+$+1).

Step D. Preparation of 1,5-Dimethyl-1H-indole-4-carboxylic Acid Indan-2-yl-(4-methyl-benzyl)-amide EDCI (2 equivalents), HOBT (1 equivalent), and 2.0 equivalents of triethylamine are added to a solution of 1,5-Dimethyl-1H-indole-4-carboxylic acid (23) (189 mg, 1.0 mmol) and (4-tolyl)-indan-2-ylamine (237 mg, 1.0 mmol, 1.0 eq.) (24) in 10 ml of anhydrous 1,2-dichloroethane. The resulting solution is stirred at room temperature for 5 hours and heated at reflux overnight. The reaction mixture is diluted with dichloromethane (20 ml), extracted with saturated sodium bicarbonate solution (10 ml×2), water (10 ml×2), and brine (10 ml). The organic layer is dried over anhydrous sodium sulfate, filtered and evaporated at reduced pressure, and purified by reverse-phase preparative HPLC to obtain 1,5-dimethyl-1H-indole-4-carboxylic acid indan-2-yl-(4-methyl-benzyl)-amide (25).

Example 7A

Preparation of 1,5-Dimethyl-1H-indole-4-carboxylic Acid (4-Dimethylamino-benzyl)-(4-isopropyl-phenyl)-amide This compound (26) may be prepared by the procedure described in the preceding example using 4-carboxy-1,5- dimethylindole and (4-isopropylphenyl)-(4'-dimethylamino) benzylamine as starting materials.

Example 8

Preparation of 5-isopropyl-1-methyl-1H-indazole-4-carboxylic Acid Indan-2-yl-(4-methyl-benzyl)-amide

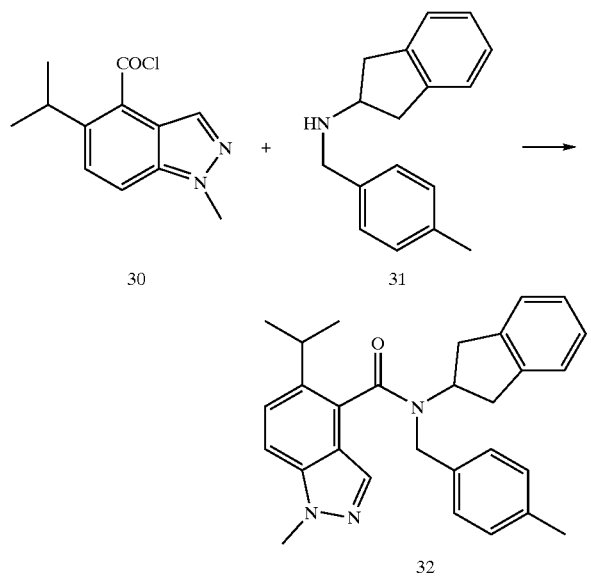

Step A. Preparation of 4-Bromo-5-isopropyl-1-methylindole (28)

A solution of 4-bromo-5-isopropylindazole (27) (488 mg, 2.04 mmol) in 5 ml of anhydrous DMF is added to a suspension of sodium hydride (122 mg, 60% in mineral oil, 3.06 mmol, 1.5 eq.) in 5 ml of DMF under nitrogen at 0° C. The resulting mixture is stirred at 0° C. for 30 minutes, then warmed to room temperature. After stirring at room temperature for an additional 2 hours, the reaction mixture is cooled to 0° C., and iodomethane (318 mg, 2.24 mmol, 1.1 eq.) is added dropwise, the mixture is stirred at 0° C. for 2 hours, then warmed to room temperature, and stirred overnight. The reaction mixture is poured into 30 ml of ice-water, extracted with ethyl acetate (30 ml×3), washed with water and brine, and dried over anhydrous sodium sulfate. The solvent is evaporated and the product is purified via flash chromatography to give 340 mg of 4-bromo-5-isopropyl-1-methylindazole $^1$H NMR (400 MHz, CDCl$_3$) 7.95 (1H, s), 7.31 (2H, S), 4.05 (3H, S), 3.55 (1H, m), 1.27 (6H, d, J=6.8Hz). MS (+VE) m/z 253(M$^+$). 165 mg of 4-bromo-5-isopropyl-2-methylindazole (28). $^1$H NMR (400 MHz, CDCl$_3$) δ 7.82 (1H, s), 7.59 (1H, d, J=9.2 Hz), 7.21 (1H, d, J=8.8 Hz), 4.16 (3H, s), 3.50 (1H, m), 1.21 (6H, d, J=6.8 Hz). MS (+VE) m/z 253(M$^+$).

Step B. Preparation of 5-Isopropyl-1-methyl-1H-indazole-4-carboxylic Acid

BuLi (1.6 M in hexane, 925 ul, 1.47 mmol, 1.1 eq.) is added under nitrogen to a solution of 4-bromo-5-isopropyl-1-methylindazole (340 mg, 1.34 mmol) (28) in 10 ml anhydrous tetrahydrofuran cooled to −78° C. The resulting solution is stirred at −78° C. for 30 minutes. The anion is quenched by introducing anhydrous carbon dioxide gas, the flask is raised to room temperature slowly. Water (20 ml) is added to the flask, the tetrahydrofuran is evaporated, and the aqueous solution is adjusted to pH 5–6 with 1.0 N hydrochloric acid. The product is extracted with ethyl acetate (15 ml×3), washed with water and brine, dried over anhydrous sodium sulfate, concentrated, and taken to dryness under high vacuum to give 270 mg of pure product (29). MS (+VE) m/z 219 (M$^+$+1).

Step C. Preparation of -Isopropyl-1-methyl-1H-indazole-4-carbonyl Chloride 2.0 N oxalychloride-dichloromethane solution (3.1 ml, 6.2 mmol, 5 eq.) is added to a solution of 5-isopropyl-1-methyl-1H-indazole carboxylic acid (270 mg, 1.24 mmol) in a mixture of 5 ml of cyclohexane and 5 ml of anhydrous THF containing one drop of DMF. The resulting solution is stirred at room temperature overnight. The solvents are evaporated; 10 ml of toluene is added, and the mixture is evaporated to dryness again to give 5-isopropyl-1-methyl-1H-indazole-4-carbonyl chloride (30) as brown foam.

Step D. Preparation of 5-Isopropyl-1-methyl-1H-indazole-4-carboxylic Acid Indan-2-yl-(4-methyl-benzyl)-amide 5-Isopropyl-1-methyl-1H-indazole-4-carbonyl chloride (0.618 mmol, 1.0 eq) (30) in 5 ml of THF is added to a solution of (4-tolyl)-indan-2-yl-amine (147 mg, 0.618 mmol) (31) in 5 ml of tetrahydrofuran containing 250 mg of triethylamine at 0° C. The resulting mixture is stirred at room temperature overnight, diluted with 20 ml of ethyl acetate, washed with water and brine, and dried over sodium sulfate. Concentration and purification by silica gel chromatography affords 168 mg of 5-isopropyl-1-methyl-1H-indazole-4-carboxylic acid indan-2-yl-(4-methyl-benzyl)-amide (32). $^1$H NMR (400 MHz, CDCl$_3$) 7.89 (1H, s), 7.42~6.92 (10H, m), 4.95 (1H, d, J=15.2 Hz), 4.66 (1H, d, J=15.2 Hz), 4.551 (1H, m), 4.05 (3H, s), 3.26~2.73 (5H, m), 2.36 (3H, s), 1.34 (6H, dd, J=1.6, 6.8Hz). MS (+VE) m/z 438 (M$^+$+1).

Example 8A

Preparation of 5-Isopropyl-1-methyl-1H-indazole-4-carboxylic Acid (4-di-methylamino-benzyl)-(4-isopropyl-phenyl)-amide 5-Isopropyl-1-methyl-1H-indazole-4-carbonyl chloride (0.618 mmol, 1.0 eq.) in 5 ml of THF is added to a solution of (4-isopropylphenyl)-(4'-dimethylamino)benzylamine (165 mg, 0.618 mmol) in 5 ml of tetrahydrofuran containing 250 mg of triethylamine at 0° C. The resulting mixture is stirred at room temperature overnight, diluted with 20 ml of ethyl acetate, washed with water and brine, and dried over sodium sulfate. Concentration and purification by silica gel chromatography affords 157 mg of 5-isopropyl-1-methyl-1H-indazole-4-carboxylic acid (4-dimethylamino-benzyl)-(4-isopropyl-phenyl)-amide (32A). $^1$H NMR (400 MHz, CDCl$_3$) 7.83 (1H, s), 7.27~7.08 (4H, m), 6.79~6.67 (6H, m), 5.38 (1H, D, J=14 Hz), 4.78 (1H, d, J=14 Hz), 3.95 (3H, s), 3.11 (1H, m), 2.95 (6H, s), 2.64 (1H, m)1.24 (6H, d, J=6.4 Hz), 1.02 (6H, d, J=6.8Hz). MS (+VE) m/z 469 (M$^+$+1).

Example 9

Synthesis of 5-Isopropyl-1-methyl-1H-benzoimidazole-4-carboxylic Acid (4-dimethylamino-benzyl)-(4-isopropyl-phenyl)-amide

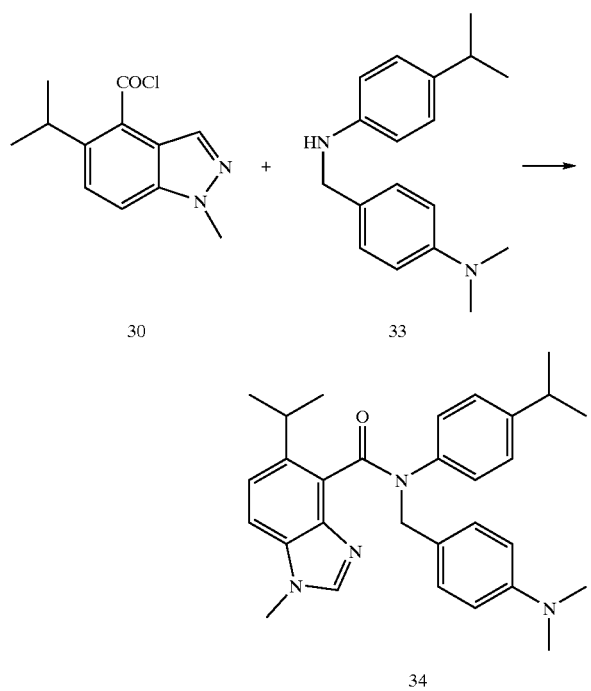

Acylchloride 0.618 mmol, 1.0 eq.) in 5 ml of THF (30) is added to the solution of (4-isopropylphenyl)-(4'-dimethylamino)benzylamine (33) (165 mg, 0.618 mmol) in 5 ml of tetrahydrofuran containing 250 mg of triethylamine at 0° C. The resulting mixture is stirred at room temperature overnight, diluted with 20 ml of ethyl acetate, washed with water and brine, and dried over sodium sulfate. Concentration and purification by silica gel chromatography affords 157 mg of amide compound (34) (54% of yield). $^1$H NMR (400 MHz, CDCl$_3$) 7.83 (1H, s), 7.27~7.08 (4H, m), 6.79~6.67 (6H, m), 5.38 (1H, D, J=14 Hz), 4.78 (1H, d, J=14 Hz), 3.95 (3H, s), 3.11 (1H, m), 2.95 (6H, s), 2.64 (1H, m)1.24 (6H, d, J=6.4 Hz), 1.02 (6H, d, J=6.8Hz). MS (+VE) m/z 469 (M$^+$+1).

Example 10

Additional Compounds

Additional substituted biarylamides are shown in Tables I–III. The compounds shown in Table I are prepared via the method provided in Scheme 1 and further illustrated in Examples 1 and 2. The compounds shown in Table II are prepared via the methods provided in Examples 3 and 4. The compounds in Table III are prepared via the method provided in Scheme 2 and further illustrated in Examples 5 and 6. Compounds that have an asterisk in the column labeled "Ca$^{2+}$ Mob.", were tested in the standard assay of C5a receptor mediated calcium mobilization given in Example 18 and found to exhibit a Ki of less than 1 µM.

All compounds in Table II were tested in the radioligand binding assay (Example 17) and found to inhibit C5a binding to the human C5a receptor 95% or more.

The LC/MS data presented in Tables I, II, and III were obtained using the following instrumentation and methods. MS spectroscopy data is Electrospray MS, obtained in positive ion mode, with a 15V Cone voltage, using a WATERS ZMD 2000 Mass Spec Detector, equipped with a WATERS 600 pump, WATERS 2487 Dual Wavelength Detector, GILSON 215 Autosampler, and a GILSON 841 Microinjector. MassLynx version 3.4 software was used for data collection and analysis.

Sample, 2–20 microliters, was injected onto a 33×4.6 mm YMC ProPack C18; 5 micron column, and eluted using a 2-phase linear gradient at a 4 mL/minute flow rate. Sample was detected at 220 and 254 nm. The elution conditions were as follows: Mobile Phase A- 95/5/0.1 Water/Methanol/TFA, Mobile Phase B- 5/95/0.1 Water/Methanol/TFA.

| Gradient time(min) | % B |
| --- | --- |
| 0 | 10 |
| 2.0 | 100 |
| 3.5 | 100 |
| 3.51 | 10 |

The total run time for the gradient was 4.0 minutes

TABLE I

| CMP # | STRUCTURE | Ca2+ Mob. | IUPAC Name |
| --- | --- | --- | --- |
| 34 | 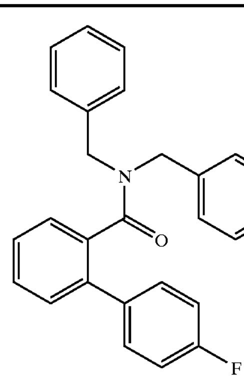 | * | N,N-dibenzyl-4'-fluoro-1,1'-biphenyl-2-carboxamide |

TABLE I-continued

| CMP # | STRUCTURE | Ca2+ Mob. | IUPAC Name |
|---|---|---|---|
| 35 | 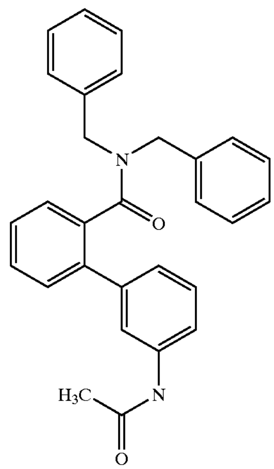 | * | 3'-(acetylamino)-N,N-dibenzyl-1,1'-biphenyl-2-carboxamide |
| 36 | 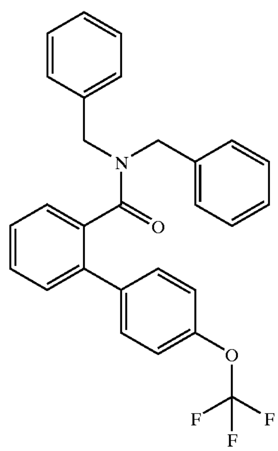 | * | N,N-dibenzyl-4'-(trifluoromethoxy)-1,1'-biphenyl-2-carboxamide |
| 37 | 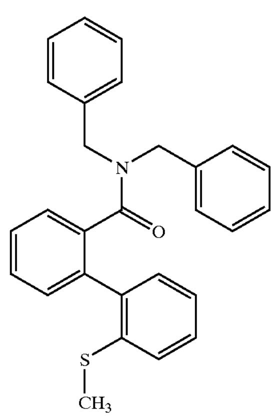 | * | N,N-dibenzyl-2'-(methylthio)-1,1'-biphenyl-2-carboxamide |

TABLE I-continued

| CMP # | STRUCTURE | Ca2+ Mob. | IUPAC Name |
|---|---|---|---|
| 38 | 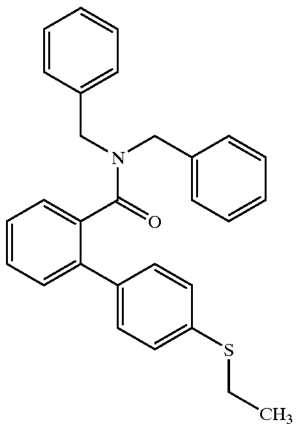 | * | N,N-dibenzyl-4'-(ethylthio)-1,1'-biphenyl-2-carboxamide |
| 39 | 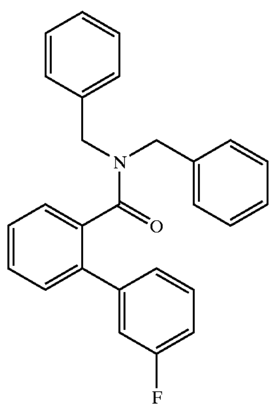 | * | N,N-dibenzyl-3'-fluoro-1,1'-biphenyl-2-carboxamide |
| 40 | 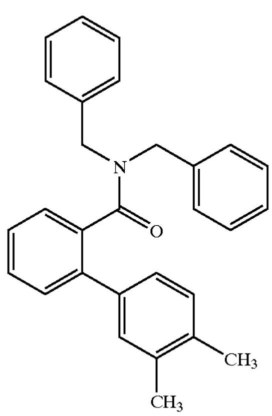 | * | N,N-dibenzyl-3',4'-dimethyl-1,1'-biphenyl-2-carboxamide |

TABLE I-continued

| CMP # | STRUCTURE | Ca2+ Mob. | IUPAC Name |
|---|---|---|---|
| 41 | 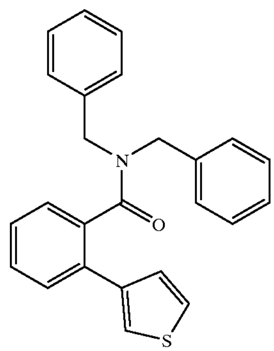 | * | N,N-dibenzyl-2-thien-3-ylbenzamide |
| 42 | 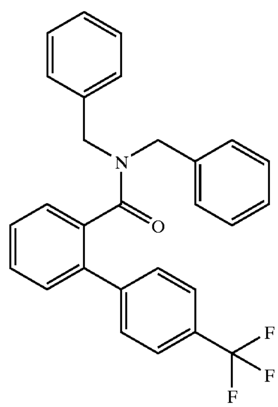 | * | N,N-dibenzyl-4'-(trifluoromethyl)-1,1'-biphenyl-2-carboxamide |
| 43 | 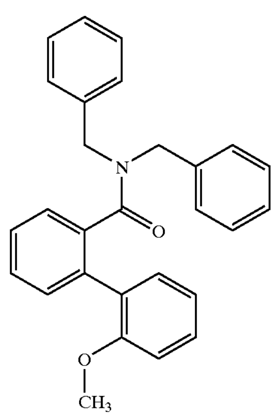 | * | N,N-dibenzyl-2'-methoxy-1,1'-biphenyl-2-carboxamide |

TABLE I-continued

| CMP # | STRUCTURE | Ca2+ Mob. | IUPAC Name |
|---|---|---|---|
| 44 | 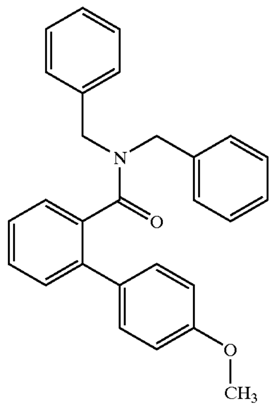 | * | N,N-dibenzyl-4'-methoxy-1,1'-biphenyl-2-carboxamide |
| 45 | 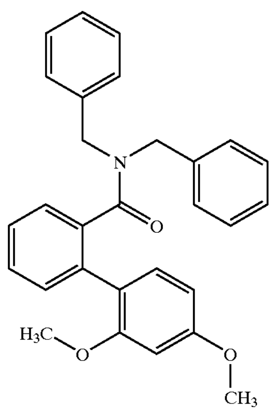 | * | N,N-dibenzyl-2',4'-dimethoxy-1,1'-biphenyl-2-carboxamide |
| 46 | 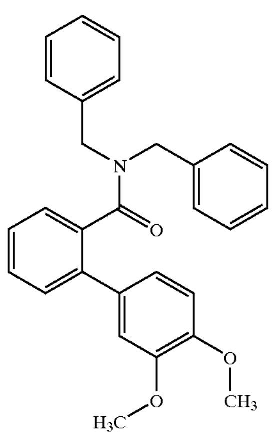 | * | N,N-dibenzyl-3',4'-dimethoxy-1,1'-biphenyl-2-carboxamide |

TABLE I-continued

| CMP # | STRUCTURE | Ca2+ Mob. | IUPAC Name |
|---|---|---|---|
| 47 | 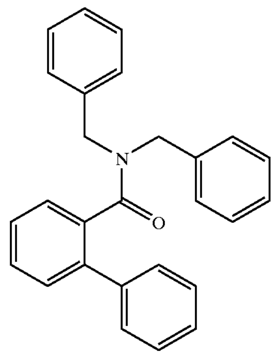 | * | N,N-dibenzyl-1,1'-biphenyl-2-carboxamide |
| 48 | 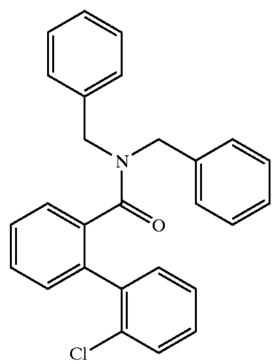 | * | N,N-dibenzyl-2'-chloro-1,1'-biphenyl-2-carboxamide |
| 49 | 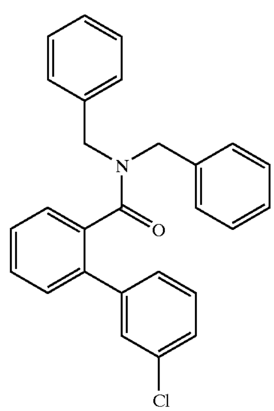 | * | N,N-dibenzyl-3'-chloro-1,1'-biphenyl-2-carboxamide |
| 50 | 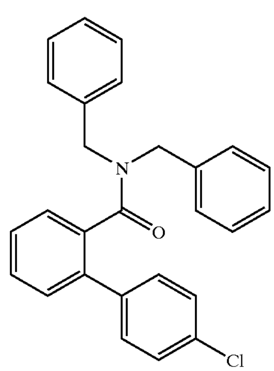 | * | N,N-dibenzyl-4'-chloro-1,1'-biphenyl-2-carboxamide |

TABLE I-continued

| CMP # | STRUCTURE | Ca2+ Mob. | IUPAC Name |
|---|---|---|---|
| 51 | 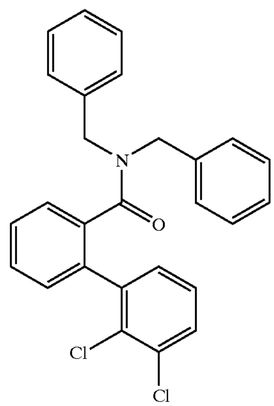 | * | N,N-dibenzyl-2',3'-dichloro-1,1'-biphenyl-2-carboxamide |
| 52 | 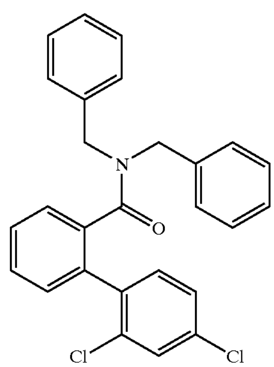 | * | N,N-dibenzyl-2',4'-dichloro-1,1'-biphenyl-2-carboxamide |
| 53 | 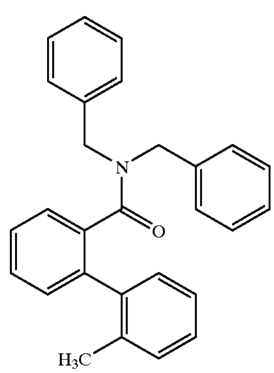 | * | N,N-dibenzyl-2'-methyl-1,1'-biphenyl-2-carboxamide |
| 54 | 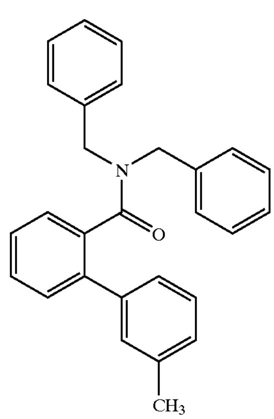 | * | N,N-dibenzyl-3'-methyl-1,1'-biphenyl-2-carboxamide |

TABLE I-continued
| CMP # | STRUCTURE | Ca2+ Mob. | IUPAC Name |
|---|---|---|---|
| 55 | 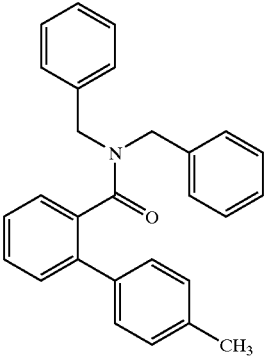 | * | N,N-dibenzyl-4'-methyl-1,1'-biphenyl-2-carboxamide |
| 56 | 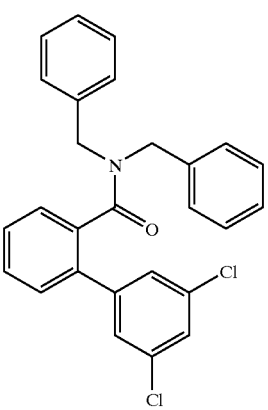 | * | N,N-dibenzyl-3',5'-dichloro-1,1'-biphenyl-2-carboxamide |
| 57 | 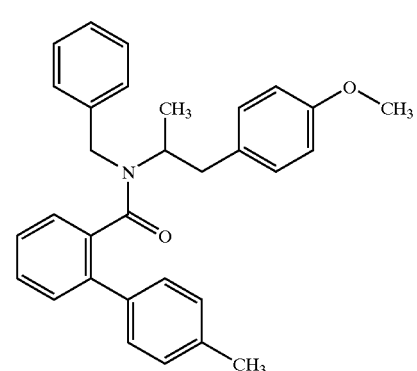 |  | N-benzyl-N-[2-(4-methoxyphenyl)-1-methylethyl]-4'-methyl-1,1'-biphenyl-2-carboxamide |
| 58 | 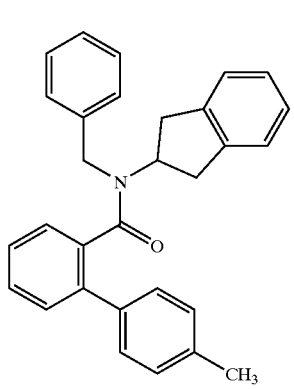 | * | N-benzyl-N-(indan-2-yl)-4'-methyl-1,1'-biphenyl-2-carboxamide |

TABLE I-continued

| CMP # | STRUCTURE | Ca2+ Mob. | IUPAC Name |
|---|---|---|---|
| 59 | 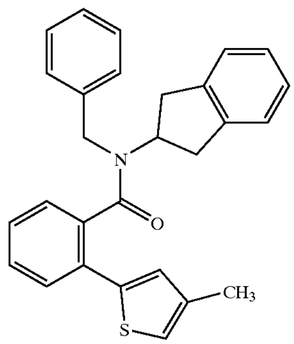 | * | N-benzyl-N-(indan-2-yl)-2-(4-methylthien-2-yl)benzamide |
| 60 | 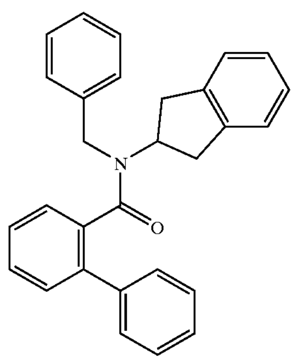 | * | N-benzyl-N-(indan-2-yl)-1,1'-biphenyl-2-carboxamide |
| 61 | 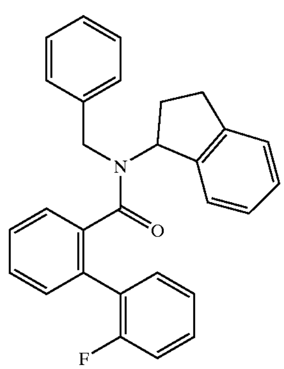 | * | N-benzyl-N-(indan-1-yl)-2'-fluoro-1,1'-biphenyl-2-carboxamide |
| 62 | 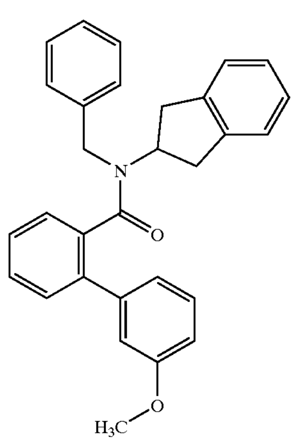 | * | N-benzyl-N-(indan-2-yl)-3'-methoxy-1,1'-biphenyl-2-carboxamide |

TABLE I-continued

| CMP # | STRUCTURE | Ca2+ Mob. | IUPAC Name |
|---|---|---|---|
| 63 | 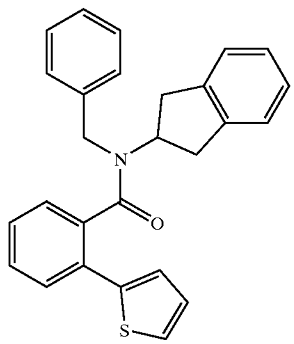 | * | N-benzyl-N-(indan-2-yl)-2-thien-2-ylbenzamide |
| 64 | 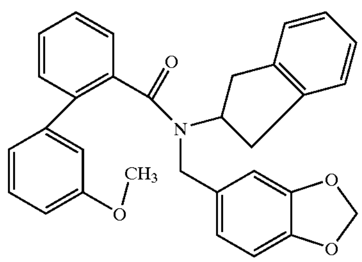 | * | N-(1,3-benzodioxol-5-ylmethyl)-N-(indan-2-yl)-3'-methoxy-1,1'-biphenyl-2-carboxamide |
| 65 | 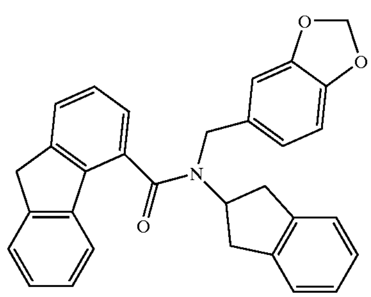 | * | N-(1,3-benzodioxol-5-ylmethyl)-N-(indan-2-yl)-9H-fluorene-4-carboxamide |
| 66 | 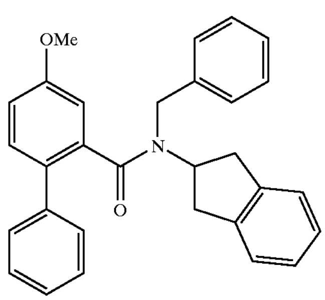 | * | N-benzyl-N-(indan-2-yl)-4-methoxy-1,1'-biphenyl-2-carboxamide |
| 67 | 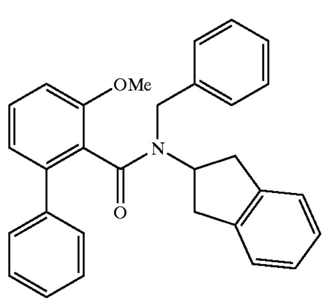 | * | N-benzyl-N-(indan-2-yl)-3-methoxy-1,1'-biphenyl-2-carboxamide |

TABLE I-continued

| CMP # | STRUCTURE | Ca2+ Mob. | IUPAC Name |
|---|---|---|---|
| 68 | 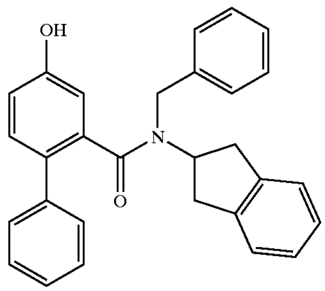 | * | N-benzyl-N-(indan-2-yl)-4-hydroxy-1,1'-biphenyl-2-carboxamide |
| 69 | 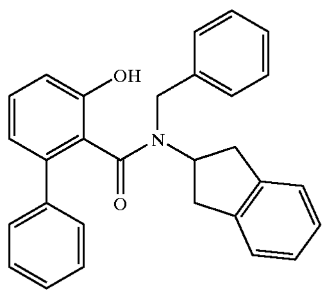 | * | N-benzyl-N-(indan-2-yl)-3-hydroxy-1,1'-biphenyl-2-carboxamide |
| 70 | 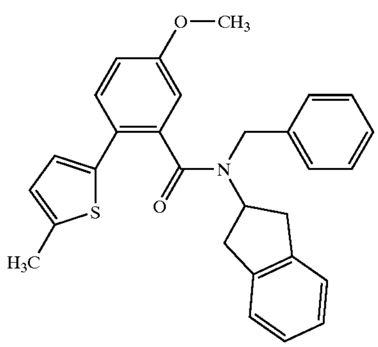 | * | N-benzyl-N-(indan-2-yl)-5-methoxy-2-(5-methylthien-2-yl)benzamide |
| 71 | 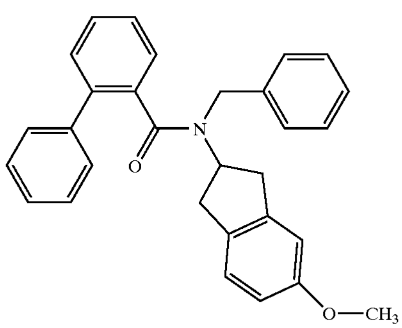 | * | N-benzyl-N-(5-methoxy-indan-2-yl)-1,1'-biphenyl-2-carboxamide |

TABLE I-continued

| CMP # | STRUCTURE | Ca2+ Mob. | IUPAC Name |
|---|---|---|---|
| 72 | 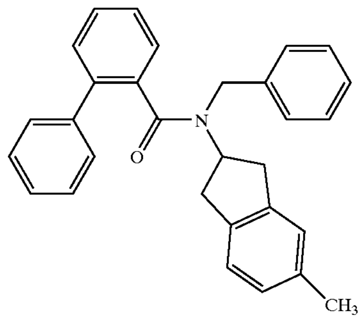 | * | N-benzyl-N-(5-methyl-indan-2-yl)-1,1'-biphenyl-2-carboxamide |
| 73 | 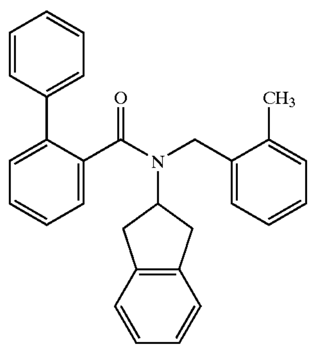 | * | N-(indan-2-yl)-N-(2-methylbenzyl)-1,1'-biphenyl-2-carboxamide |
| 74 | 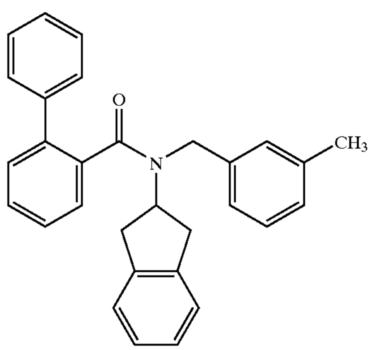 | * | N-(indan-2-yl)-N-(3-methylbenzyl)-1,1'-biphenyl-2-carboxamide |
| 75 | 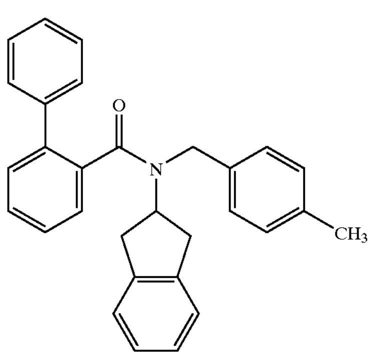 | * | N-(indan-2-yl)-N-(4-methylbenzyl)-1,1'-biphenyl-2-carboxamide |

TABLE I-continued

| CMP # | STRUCTURE | Ca2+ Mob. | IUPAC Name |
|---|---|---|---|
| 76 | 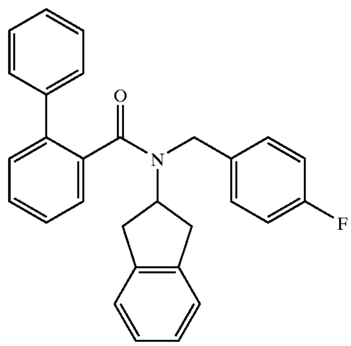 | * | N-(indan-2-yl)-N-(4-fluorobenzyl)-1,1'-biphenyl-2-carboxamide |
| 77 | 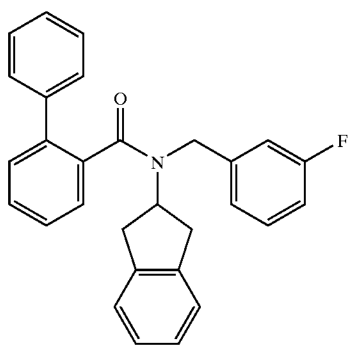 | * | N-(indan-2-yl)-N-(3-fluorobenzyl)-1,1'-biphenyl-2-carboxamide |
| 78 | 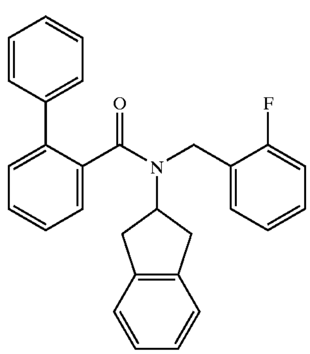 | * | N-(indan-2-yl)-N-(2-fluorobenzyl)-1,1'-biphenyl-2-carboxamide |
| 79 | 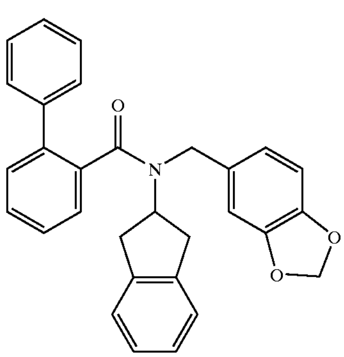 | * | N-(1,3-benzodioxol-5-ylmethyl)-N-(indan-2-yl)-1,1'-biphenyl-2-carboxamide |

TABLE I-continued

| CMP # | STRUCTURE | Ca2+ Mob. | IUPAC Name |
|---|---|---|---|
| 80 | 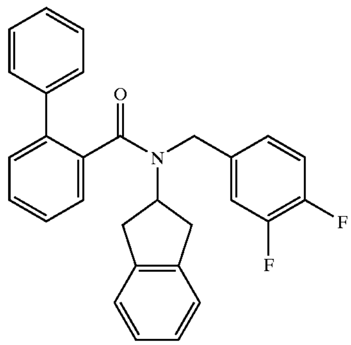 | * | N-(3,4-difluorobenzyl)-N-(indan-2-yl)-1,1'-biphenyl-2-carboxamide |
| 81 | 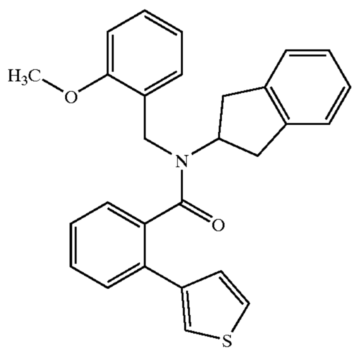 | * | N-(indan-2-yl)-N-(2-methoxybenzyl)-2-thien-3-ylbenzamide |
| 82 | 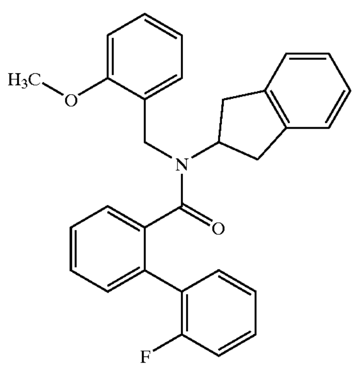 | * | N-(indan-2-yl)-2'-fluoro-N-(2-methoxybenzyl)-1,1'-biphenyl-2-carboxamide |
| 83 | 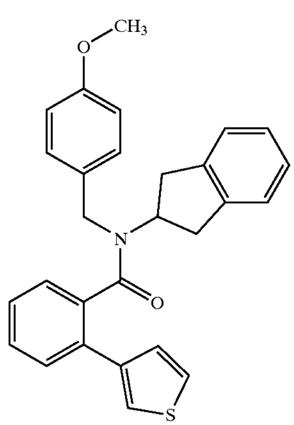 | * | N-(indan-2-yl)-N-(4-methoxybenzyl)-2-thien-3-ylbenzamide |

TABLE I-continued
| CMP # | STRUCTURE | Ca2+ Mob. | IUPAC Name |
|---|---|---|---|
| 84 | 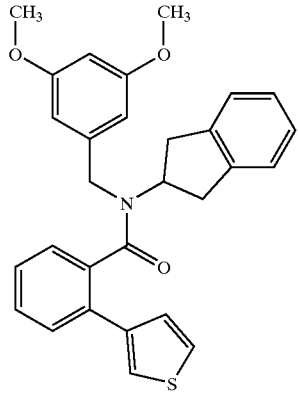 | * | N-(indan-2-yl)-N-(3,5-dimethoxybenzyl)-2-thien-3-ylbenzamide |
| 85 | 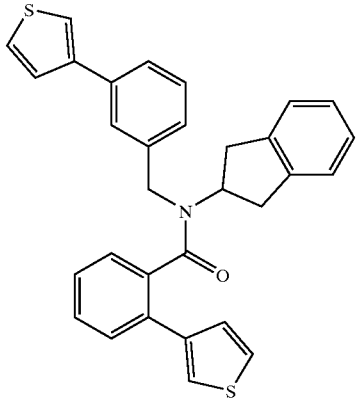 | * | N-(indan-2-yl)-2-thien-3-yl-N-(3-thien-3-ylbenzyl)benzamide |
| 86 | 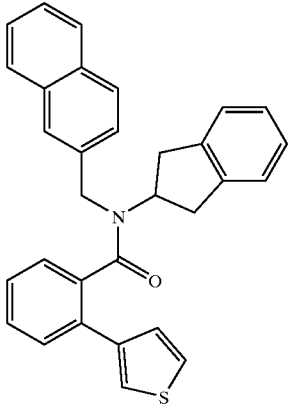 | * | N-(indan-2-yl)-N-(2-naphthylmethyl)-2-thien-3-ylbenzamide |

TABLE I-continued
| CMP # | STRUCTURE | Ca2+ Mob. | IUPAC Name |
|---|---|---|---|
| 87 | 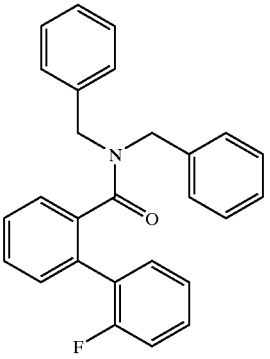 | * | N,N-dibenzyl-2'-fluoro-1,1'-biphenyl-2-carboxamide |
| 88 | 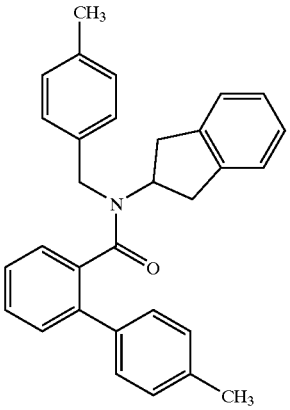 | * | N-(indan-2-yl)-4'-methyl-N-(4-methylbenzyl)-1,1'-biphenyl-2-carboxamide |
| 89 | 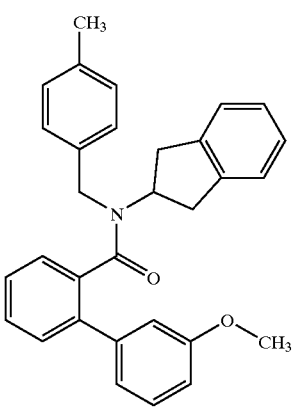 | * | N-(indan-2-yl)-3'-methoxy-N-(4-methylbenzyl)-1,1'-biphenyl-2-carboxamide |

TABLE I-continued
| CMP # | STRUCTURE | Ca2+ Mob. | IUPAC Name |
|---|---|---|---|
| 90 | 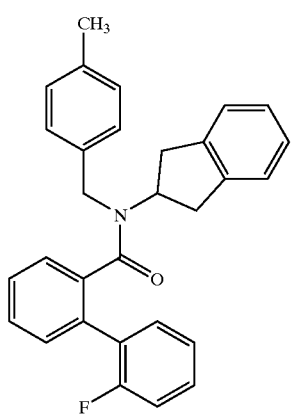 | * | N-(indan-2-yl)-2'-fluoro-N-(4-methylbenzyl)-1,1'-biphenyl-2-carboxamide |
| 91 | 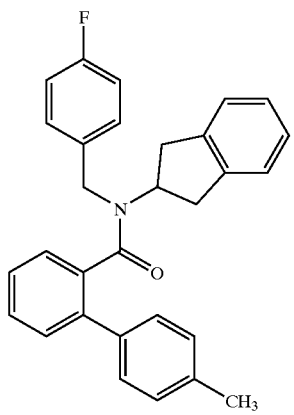 | * | N-(indan-2-yl)-N-(4-fluorobenzyl)-4'-methyl-1,1'-biphenyl-2-carboxamide |
| 92 | 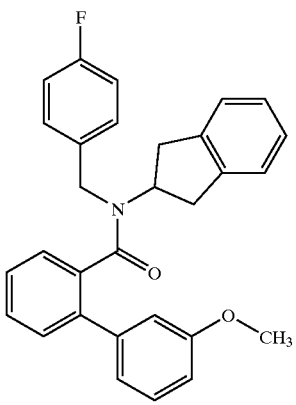 | * | N-(indan-2-yl)-N-(4-fluorobenzyl)-3'-methoxy-1,1'-biphenyl-2-carboxamide |

TABLE I-continued
| CMP # | STRUCTURE | Ca2+ Mob. | IUPAC Name |
|---|---|---|---|
| 93 | 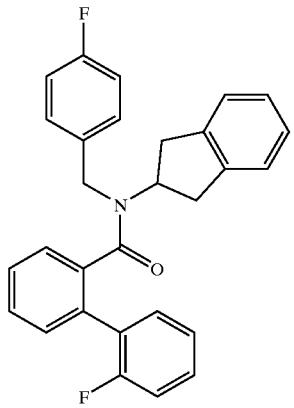 | * | N-(indan-2-yl)-2'-fluoro-N-(4-fluorobenzyl)-1,1'-biphenyl-2-carboxamide |
| 94 | 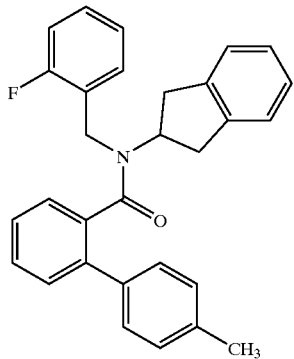 | * | N-(indan-2-yl)-N-(2-fluorobenzyl)-4'-methyl-1,1'-biphenyl-2-carboxamide |
| 95 | 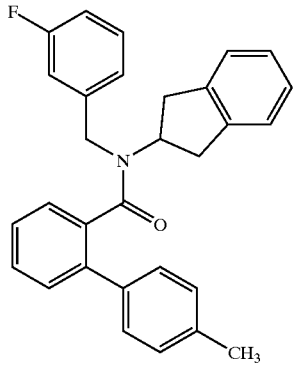 | * | N-(indan-2-yl)-N-(3-fluorobenzyl)-4'-methyl-1,1'-biphenyl-2-carboxamide |
| 96 | 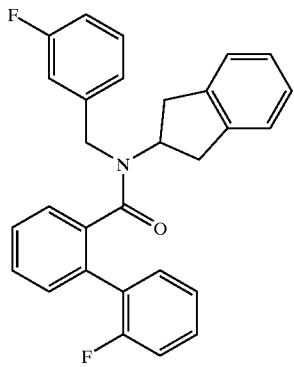 | * | N-(indan-2-yl)-2'-fluoro-N-(3-fluorobenzyl)-1,1'-biphenyl-2-carboxamide |

TABLE I-continued

| CMP # | STRUCTURE | Ca2+ Mob. | IUPAC Name |
|---|---|---|---|
| 97 | 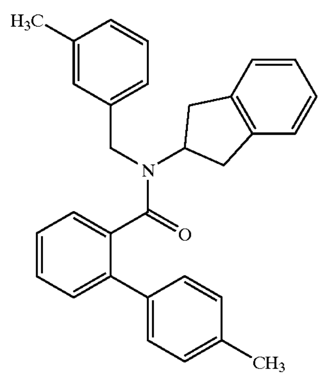 | * | N-(indan-2-yl)-4'-methyl-N-(3-methylbenzyl)-1,1'-biphenyl-2-carboxamide |
| 98 | 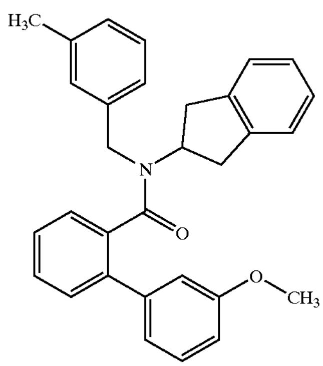 | * | N-(indan-2-yl)-3'-methoxy-N-(3-methylbenzyl)-1,1'-biphenyl-2-carboxamide |
| 99 | 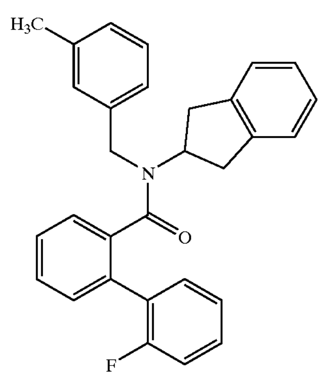 | * | N-(indan-2-yl)-2'-fluoro-N-(3-methylbenzyl)-1,1'-biphenyl-2-carboxamide |
| 100 | 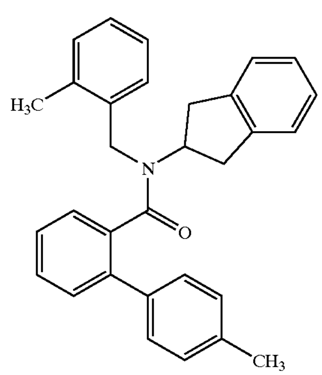 | * | N-(indan-2-yl)-4'-methyl-N-(2-methylbenzyl)-1,1'-biphenyl-2-carboxamide |

TABLE I-continued
| CMP # | STRUCTURE | Ca2+ Mob. | IUPAC Name |
|---|---|---|---|
| 101 | 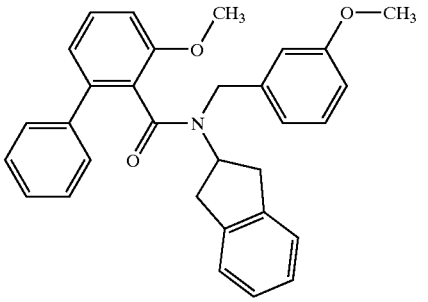 | * | N-(indan-2-yl)-3-methoxy-N-(3-methoxybenzyl)-1,1'-biphenyl-2-carboxamide |
| 102 | 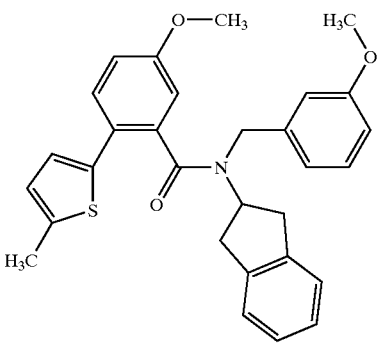 | * | N-(indan-2-yl)-5-methoxy-N-(3-methoxybenzyl)-2-(5-methylthien-2-yl)benzamide |
| 103 | 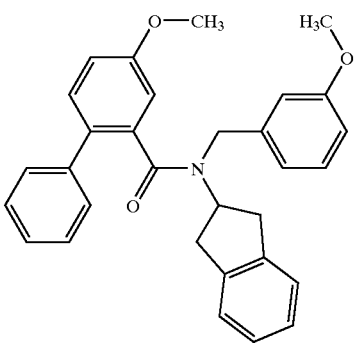 | * | N-(indan-2-yl)-4-methoxy-N-(3-methoxybenzyl)-1,1'-biphenyl-2-carboxamide |
| 104 | 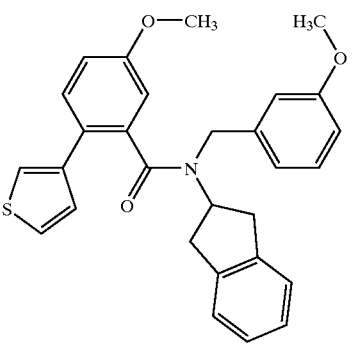 | * | N-(indan-2-yl)-5-methoxy-N-(3-methoxybenzyl)-2-thien-3-ylbenzamide |

TABLE I-continued
| CMP # | STRUCTURE | Ca2+ Mob. | IUPAC Name |
|---|---|---|---|
| 105 | 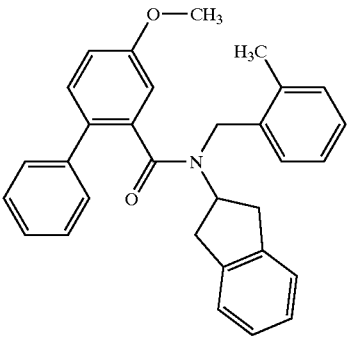 | * | N-(indan-2-yl)-4-methoxy-N-(2-methylbenzyl)-1,1'-biphenyl-2-carboxamide |
| 106 | 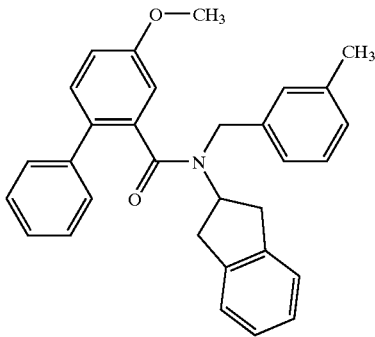 | * | N-(indan-2-yl)-4-methoxy-N-(3-methylbenzyl)-1,1'-biphenyl-2-carboxamide |
| 107 | 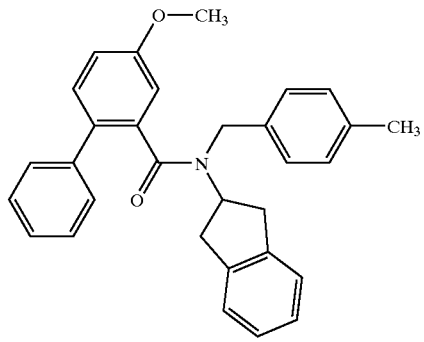 | * | N-(indan-2-yl)-4-methoxy-N-(4-methylbenzyl)-1,1'-biphenyl-2-carboxamide |
| 108 | 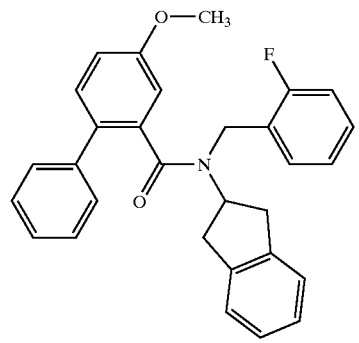 | * | N-(indan-2-yl)-N-(2-fluorobenzyl)-4-methoxy-1,1'-biphenyl-2-carboxamide |

TABLE I-continued

| CMP # | STRUCTURE | Ca2+ Mob. | IUPAC Name |
|---|---|---|---|
| 109 | 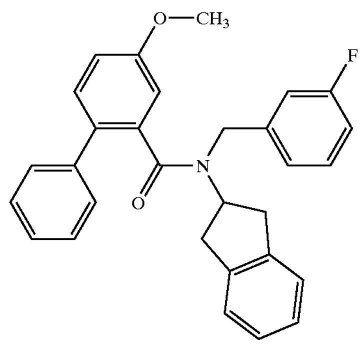 | * | N-(indan-2-yl)-N-(3-fluorobenzyl)-4-methoxy-1,1'-biphenyl-2-carboxamide |
| 110 | 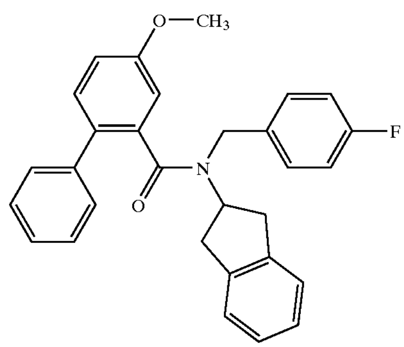 | * | N-(indan-2-yl)-N-(4-fluorobenzyl)-4-methoxy-1,1'-biphenyl-2-carboxamide |
| 111 | 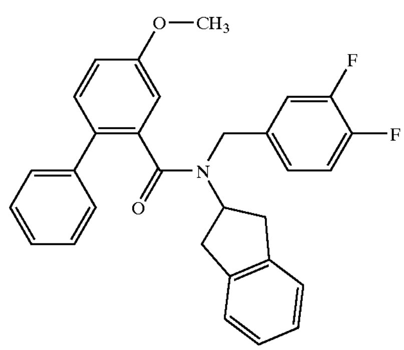 | * | N-(3,4-difluorobenzyl)-N-(indan-2-yl)-4-methoxy-1,1'-biphenyl-2-carboxamide |
| 112 | 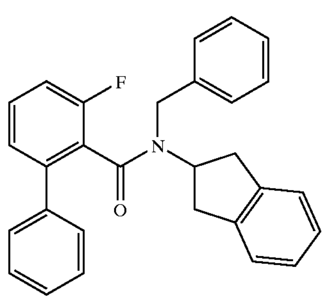 | * | N-benzyl-N-(indan-2-yl)-3-fluoro-1,1'-biphenyl-2-carboxamide |

TABLE I-continued

| CMP # | STRUCTURE | Ca2+ Mob. | IUPAC Name |
|---|---|---|---|
| 113 | 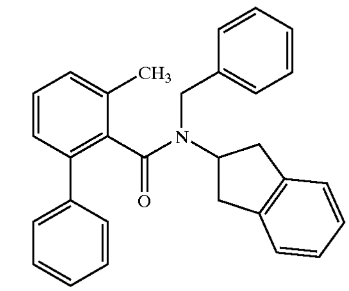 | * | N-benzyl-N-(indan-2-yl)-3-methyl-1,1'-biphenyl-2-carboxamide |
| 114 | 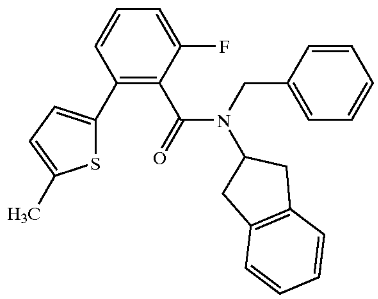 | * | N-benzyl-N-(indan-2-yl)-2-fluoro-6-(5-methylthien-2-yl)benzamide |
| 115 | 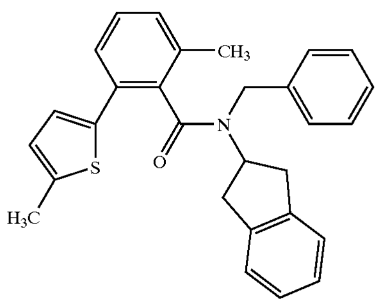 | * | N-benzyl-N-(indan-2-yl)-2-methyl-6-(5-methylthien-2-yl)benzamide |
| 116 | 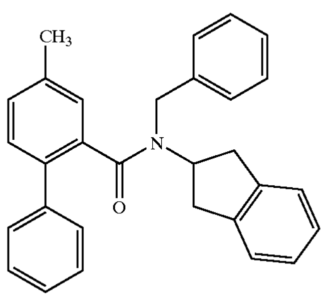 | * | N-benzyl-N-(indan-2-yl)-4-methyl-1,1'-biphenyl-2-carboxamide |
| 117 | 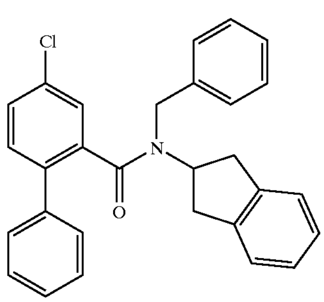 | * | N-benzyl-4-chloro-N-(indan-2-yl)-1,1'-biphenyl-2-carboxamide |

TABLE I-continued

| CMP # | STRUCTURE | Ca2+ Mob. | IUPAC Name |
|---|---|---|---|
| 118 | 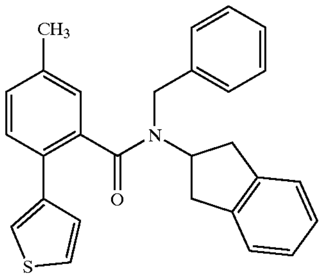 | * | N-benzyl-N-(indan-2-yl)-5-methyl-2-thien-3-ylbenzamide |
| 119 | 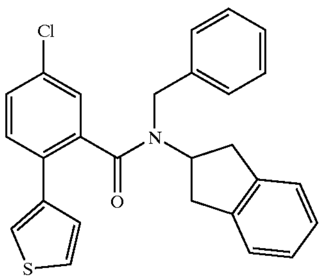 | * | N-benzyl-5-chloro-N-(indan-2-yl)-2-thien-3-ylbenzamide |
| 120 | 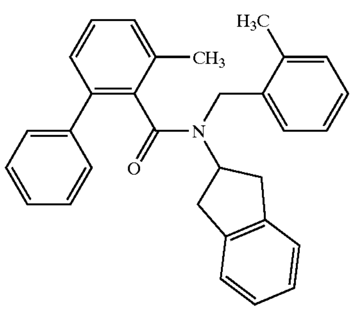 | * | N-(indan-2-yl)-3-methyl-N-(2-methylbenzyl)-1,1'-biphenyl-2-carboxamide |
| 121 | 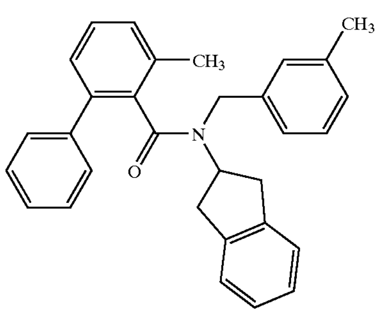 | * | N-(indan-2-yl)-3-methyl-N-(3-methylbenzyl)-1,1'-biphenyl-2-carboxamide |
| 122 | 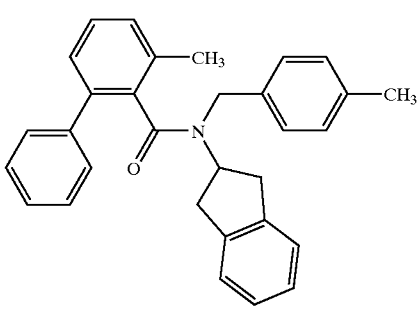 | * | N-(indan-2-yl)-3-methyl-N-(4-methylbenzyl)-1,1'-biphenyl-2-carboxamide |

TABLE I-continued

| CMP # | STRUCTURE | Ca2+ Mob. | IUPAC Name |
|---|---|---|---|
| 123 | 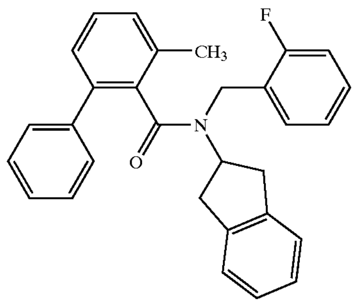 | * | N-(indan-2-yl)-N-(2-fluorobenzyl)-3-methyl-1,1'-biphenyl-2-carboxamide |
| 124 | 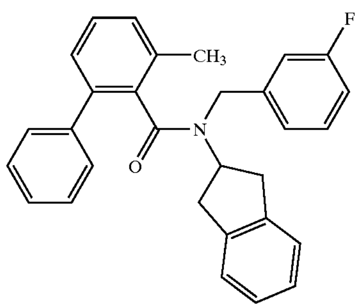 | * | N-(indan-2-yl)-N-(3-fluorobenzyl)-3-methyl-1,1'-biphenyl-2-carboxamide |
| 125 | 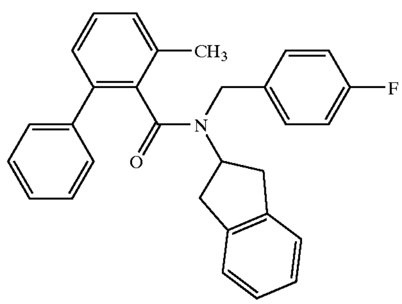 | * | N-(indan-2-yl)-N-(4-fluorobenzyl)-3-methyl-1,1'-biphenyl-2-carboxamide |
| 126 | 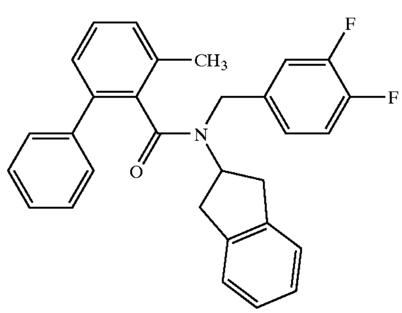 | * | N-(3,4-difluorobenzyl)-N-(indan-2-yl)-3-methyl-1,1'-biphenyl-2-carboxamide |
| 127 | 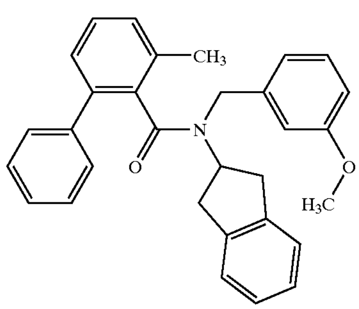 | * | N-(indan-2-yl)-N-(3-methoxybenzyl)-3-methyl-1,1'-biphenyl-2-carboxamide |

TABLE I-continued

| CMP # | STRUCTURE | Ca2+ Mob. | IUPAC Name |
|---|---|---|---|
| 128 | 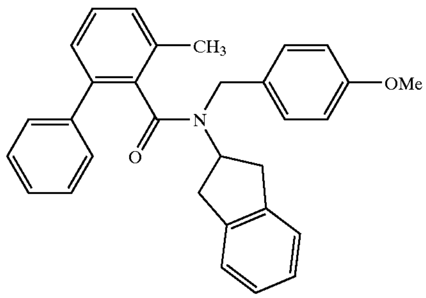 | * | N-(indan-2-yl)-N-(4-methoxybenzyl)-3-methyl-1,1'-biphenyl-2-carboxamide |
| 129 | 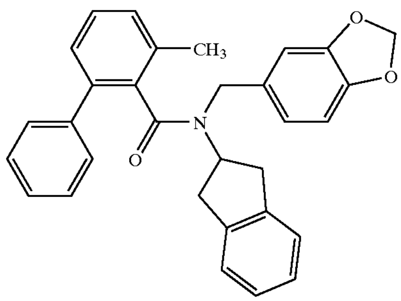 | * | N-(1,3-benzodioxol-5-ylmethyl)-N-(indan-2-yl)-3-methyl-1,1'-biphenyl-2-carboxamide |
| 130 | 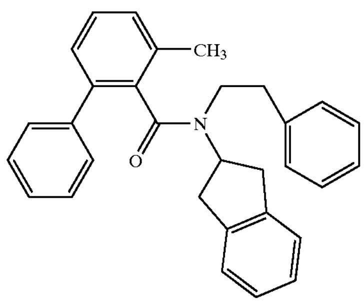 | * | N-(indan-2-yl)-3-methyl-N-(2-phenylethyl)-1,1'-biphenyl-2-carboxamide |
| 131 | 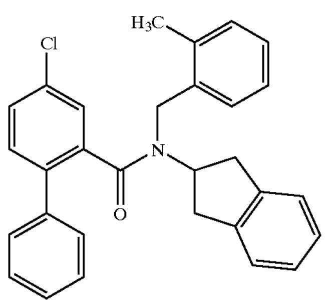 | * | 4-chloro-N-(indan-2-yl)-N-(2-methylbenzyl)-1,1'-biphenyl-2-carboxamide |
| 132 | 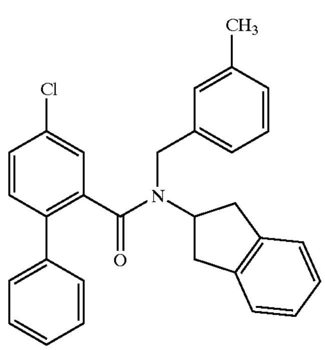 | * | 4-chloro-N-(indan-2-yl)-N-(3-methylbenzyl)-1,1'-biphenyl-2-carboxamide |

TABLE I-continued

| CMP # | STRUCTURE | Ca2+ Mob. | IUPAC Name |
|---|---|---|---|
| 133 | 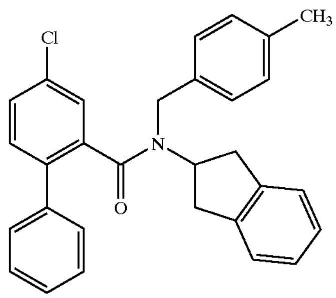 | | 4-chloro-N-(indan-2-yl)-N-(4-methylbenzyl)-1,1'-biphenyl-2-carboxamide |
| 134 | 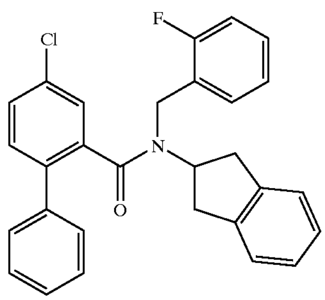 | * | 4-chloro-N-(indan-2-yl)-N-(2-fluorobenzyl)-1,1'-biphenyl-2-carboxamide |
| 135 | 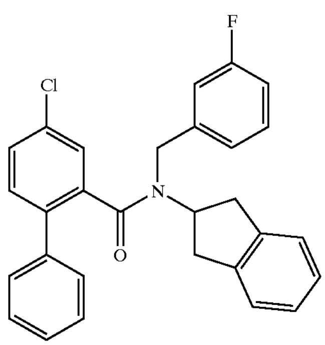 | * | 4-chloro-N-(indan-2-yl)-N-(3-fluorobenzyl)-1,1'-biphenyl-2-carboxamide |
| 136 | 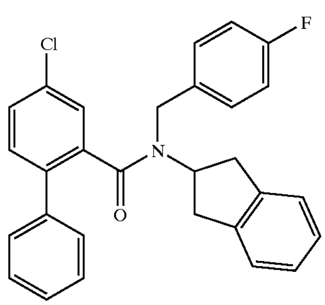 | * | 4-chloro-N-(indan-2-yl)-N-(4-fluorobenzyl)-1,1'-biphenyl-2-carboxamide |

TABLE I-continued

| CMP # | STRUCTURE | Ca2+ Mob. | IUPAC Name |
|---|---|---|---|
| 137 | 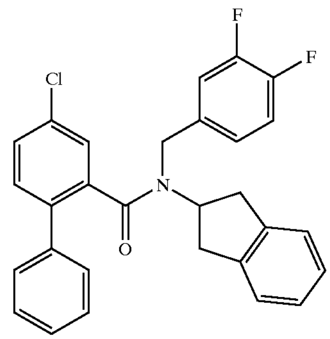 | * | 4-chloro-N-(3,4-difluorobenzyl)-N-(indan-2-yl)-1,1'-biphenyl-2-carboxamide |
| 138 | 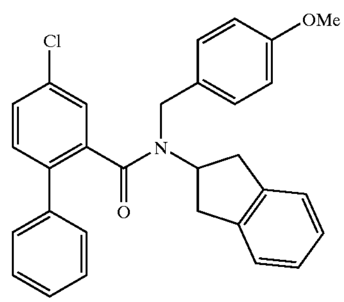 | * | 4-chloro-N-(indan-2-yl)-N-(4-methoxybenzyl)-1,1'-biphenyl-2-carboxamide |
| 139 | 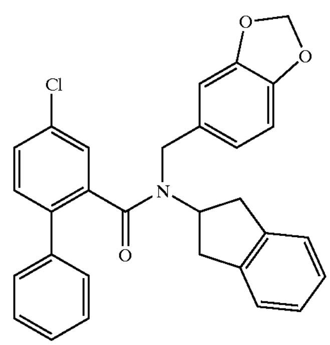 | * | N-(1,3-benzodioxol-5-ylmethyl)-4-chloro-N-(indan-2-yl)-1,1'-biphenyl-2-carboxamide |
| 140 | 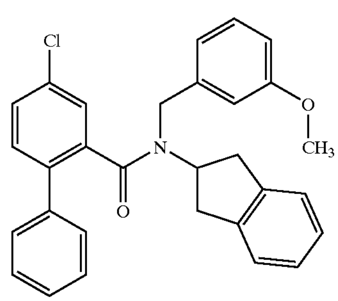 | * | 4-chloro-N-(indan-2-yl)-N-(3-methoxybenzyl)-1,1'-biphenyl-2-carboxamide |
| 141 | 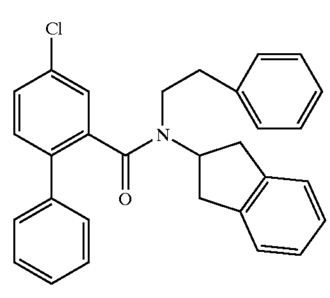 | * | 4-chloro-N-(indan-2-yl)-N-(2-phenylethyl)-1,1'-biphenyl-2-carboxamide |

TABLE I-continued

| CMP # | STRUCTURE | Ca2+ Mob. | IUPAC Name |
|---|---|---|---|
| 142 | 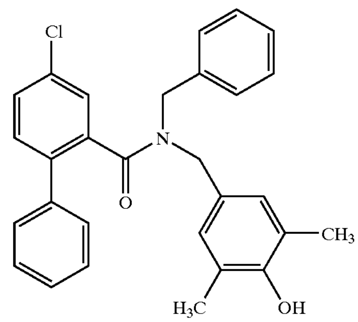 | * | N-benzyl-4-chloro-N-(4-hydroxy-3,5-dimethylbenzyl)-1,1'-biphenyl-2-carboxamide |
| 143 | 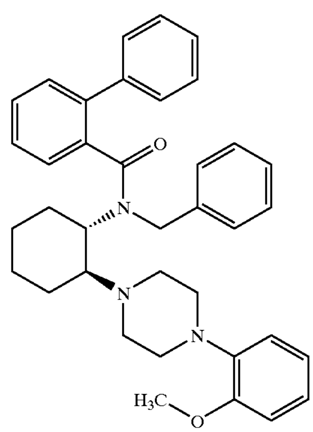 | Chiral | N-benzyl-N-{(1S,2S)-2-[4-(2-methoxyphenyl)piperazin-1-yl]-cyclohexyl}-1,1'-biphenyl-2-carboxamide |
| 144 | 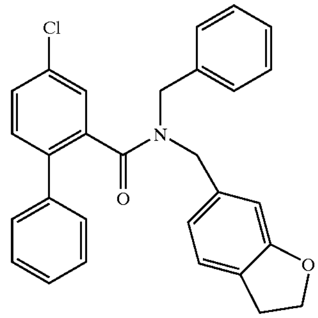 | * | N-benzyl-4-chloro-N-(2,3-dihydro-1-benzofuran-6-ylmethyl)-1,1'-biphenyl-2-carboxamide |
| 145 | 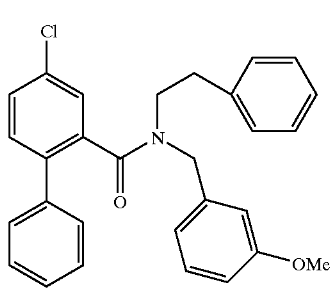 | * | 4-chloro-N-(3-methoxybenzyl)-N-(2-phenylethyl)-1,1'-biphenyl-2-carboxamide |

TABLE I-continued

| CMP # | STRUCTURE | Ca2+ Mob. | IUPAC Name |
|---|---|---|---|
| 146 | 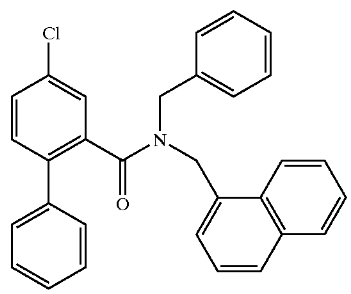 | * | N-benzyl-4-chloro-N-(1-naphthylmethyl)-1,1'-biphenyl-2-carboxamide |
| 147 | 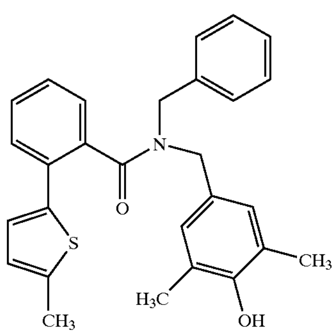 | * | N-benzyl-N-(4-hydroxy-3,5-dimethylbenzyl)-2-(5-methylthien-2-yl)benzamide |
| 148 | 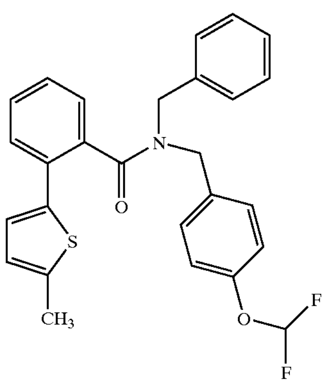 | * | N-benzyl-N-[4-(difluoromethoxy)benzyl]-2-(5-methylthien-2-yl)benzamide |
| 149 | 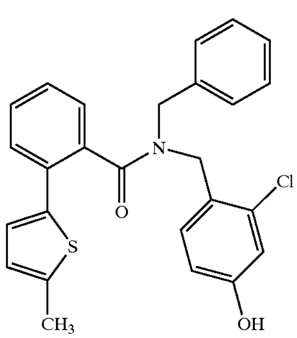 | * | N-benzyl-N-(2-chloro-4-hydroxybenzyl)-2-(5-methylthien-2-yl)benzamide |

TABLE I-continued

| CMP # | STRUCTURE | Ca2+ Mob. | IUPAC Name |
|---|---|---|---|
| 150 | 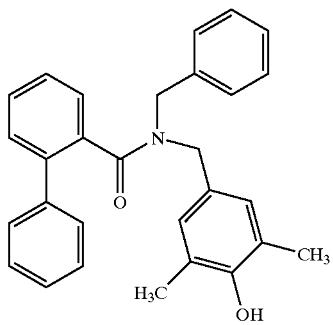 | * | N-benzyl-N-(4-hydroxy-3,5-dimethylbenzyl)-1,1'-biphenyl-2-carboxamide |
| 151 | 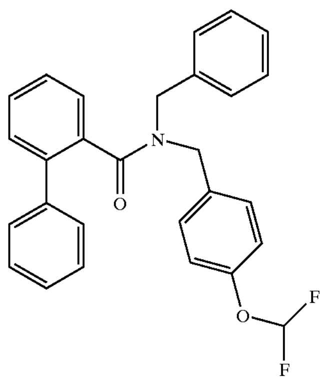 | * | N-benzyl-N-[4-(difluoromethoxy)benzyl]-1,1'-biphenyl-2-carboxamide |
| 152 | 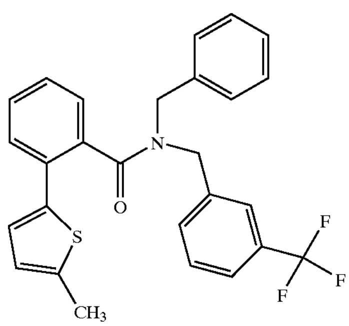 | | N-benzyl-2-(5-methylthien-2-yl)-N-[3-(trifluoromethyl)benzyl]benzamide |

TABLE II

| CMP# | STRUCTURE | IUPAC Name | LC (min.) | MW | LCMS |
|---|---|---|---|---|---|
| 153 | 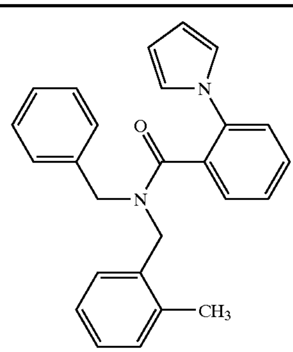 | N-benzyl-N-(2-methylbenzyl)-2-(1H-pyrrol-1-yl)benzamide | 2.27 | 380.49 | 380.19 |

TABLE II-continued
| CMP# | STRUCTURE | IUPAC Name | LC (min.) | MW | LCMS |
|---|---|---|---|---|---|
| 154 | 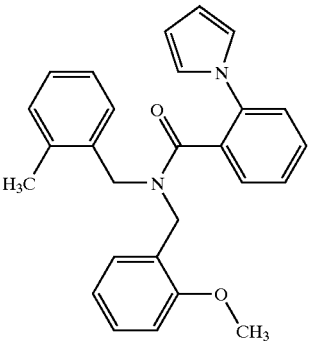 | N-(2-methoxybenzyl)-N-(2-methylbenzyl)-2-(1H-pyrrol-1-yl)benzamide | 2.27 | 410.51 | 410.20 |
| 155 | 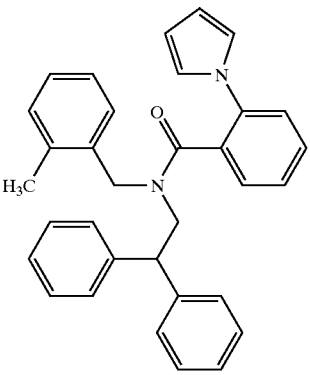 | N-(2,2-diphenylethyl)-N-(2-methylbenzyl)-2-(1H-pyrrol-1-yl)benzamide | 2.38 | 470.61 | 470.24 |
| 156 | 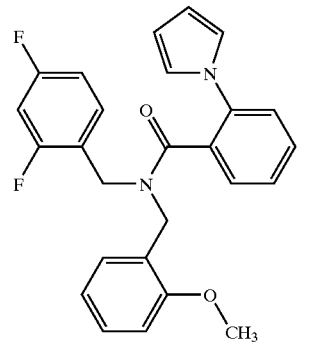 | N-(2,4-difluorobenzyl)-N-(2-methoxybenzyl)-2-(1H-pyrrol-1-yl)benzamide | 2.26 | 432.47 | 432.16 |
| 157 | 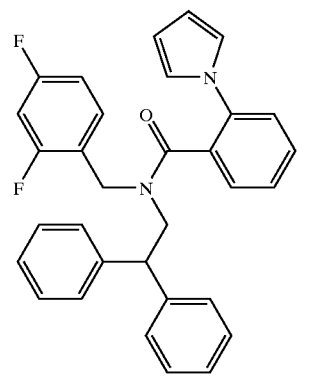 | N-(2,4-difluorobenzyl)-N-(2,2-diphenylethyl)-2-(1H-pyrrol-1-yl)benzannde | 2.36 | 492.57 | 492.20 |

TABLE II-continued

| CMP# | STRUCTURE | IUPAC Name | LC (min.) | MW | LCMS |
|---|---|---|---|---|---|
| 158 | 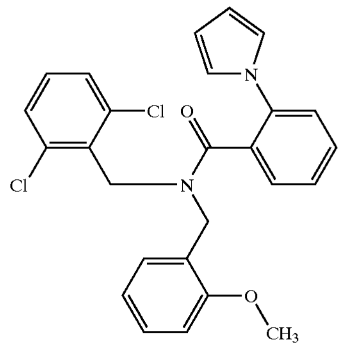 | N-(2,6-dichlorobenzyl)-N-(2-methoxybenzyl)-2-(1H-pyrrol-1-yl)benzamide | 2.28 | 465.38 | 464.11 |
| 159 | 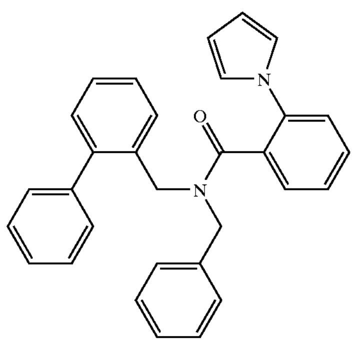 | N-benzyl-N-(1,1'-biphenyl-2-ylmethyl)-2-(1H-pyrrol-1-yl)benzamide | 2.34 | 442.56 | 442.20 |
| 160 | 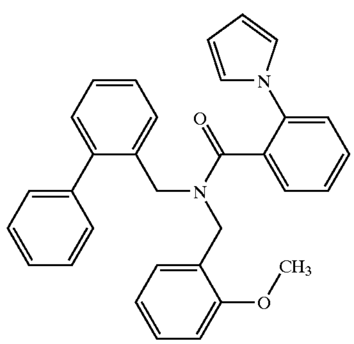 | N-(1,1'-biphenyl-2-ylmethyl)-N-(2-methoxybenzyl)-2-(1H-pyrrol-1-yl)benzamide | 2.35 | 472.59 | 472.22 |
| 161 | 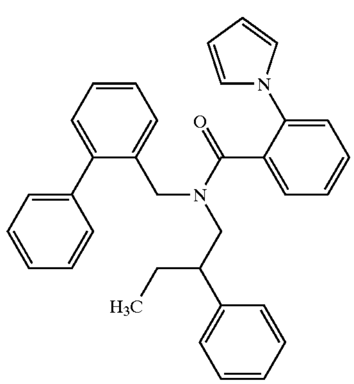 | N-(1,1'-biphenyl-2-ylmethyl)-N-(2-phenylbutyl)-2-(1H-pyrrol-1-yl)benzamide | 2.46 | 484.64 | 484.25 |

TABLE II-continued

| CMP# | STRUCTURE | IUPAC Name | LC (min.) | MW | LCMS |
|------|-----------|------------|-----------|-----|------|
| 162 | 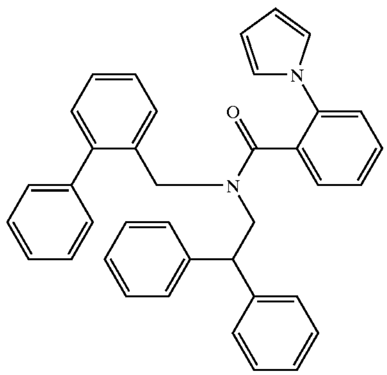 | N-(1,1'-biphenyl-2-ylmethyl)-N-(2,2-diphenylethyl)-2-(1H-pyrrol-1-yl)benzamide | 2.45 | 532.68 | 532.25 |
| 163 | 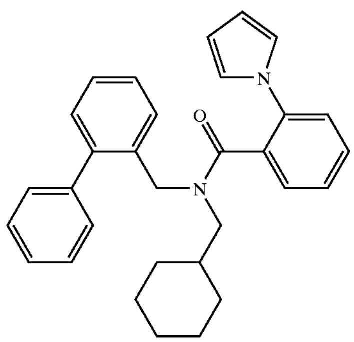 | N-(1,1'-biphenyl-2-ylmethyl)-N-(cyclohexylmethyl)-2-(1H-pyrrol-1-yl)benzamide | 2.01 | 448.61 | 448.25 |
| 164 | 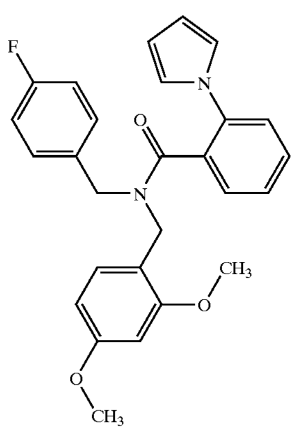 | N-(2,4-dimethoxybenzyl)-N-(4-fluorobenzyl)-2-(1H-pyrrol-1-yl)benzamide | 1.3 | 444.50 | 444.18 |
| 165 | 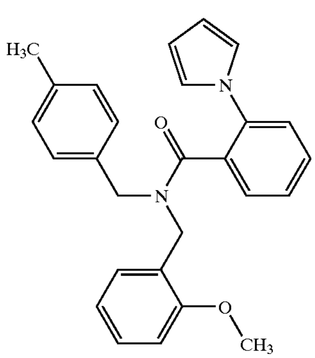 | N-(2-methoxybenzyl)-N-(4-methylbenzyl)-2-(1H-pyrrol-1-yl)benzamide | 1.34 | 410.51 | 410.20 |

TABLE II-continued
| CMP# | STRUCTURE | IUPAC Name | LC (min.) | MW | LCMS |
|---|---|---|---|---|---|
| 166 | 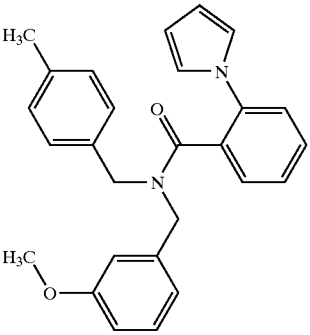 | N-(3-methoxybenzyl)-N-(4-methylbenzyl)-2-(1H-pyrrol-1-yl)benzamide | 1.33 | 410.51 | 410.20 |
| 167 | 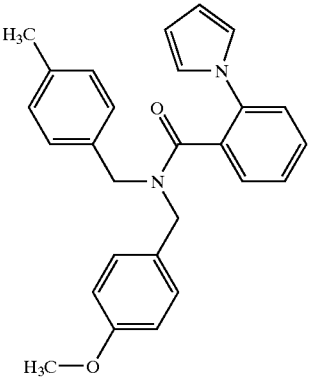 | N-(4-methoxybenzyl)-N-(4-methylbenzyl)-2-(1H-pyrrol-1-yl)benzamide | 1.33 | 410.51 | 410.20 |
| 168 | 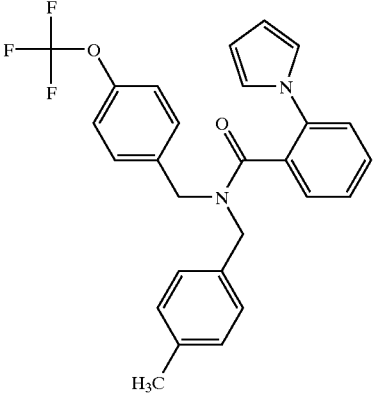 | N-(4-methylbenzyl)-2-(1H-pyrrol-1-yl)-N-[4-(trifluoromethoxy)benzyl]benzamide | 1.37 | 464.49 | 464.17 |
| 169 | 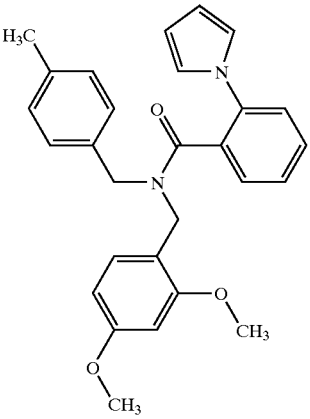 | N-(2,4-dimethoxybenzyl)-N-(4-methylbenzyl)-2-(1H-pyrrol-1-yl)benzamide | 1.33 | 440.54 | 440.21 |

TABLE II-continued

| CMP# | STRUCTURE | IUPAC Name | LC (min.) | MW | LCMS |
|---|---|---|---|---|---|
| 170 | 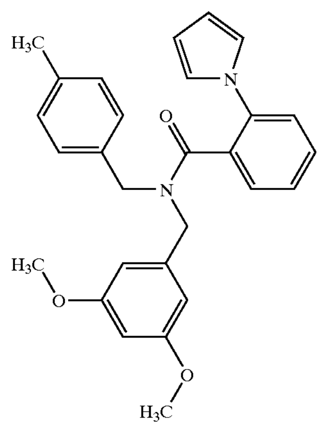 | N-(3,5-dimethoxybenzyl)-N-(4-methylbenzyl)-2-(1H-pyrrol-1-yl)benzamide | 1.33 | 440.54 | 440.21 |
| 171 | 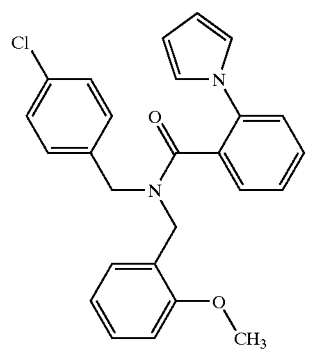 | N-(4-chlorobenzyl)-N-(2-methoxybenzyl)-2-(1H-pyrrol-1-yl)benzamide | 1.34 | 430.93 | 430.14 |
| 172 | 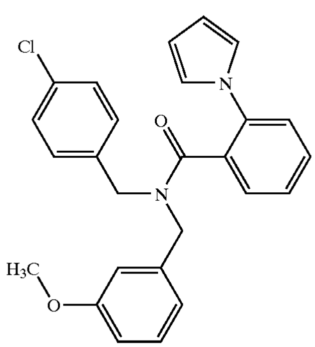 | N-(4-chlorobenzyl)-N-(3-methoxybenzyl)-2-(1H-pyrrol-1-yl)benzamide | 1.33 | 430.93 | 430.14 |
| 173 | 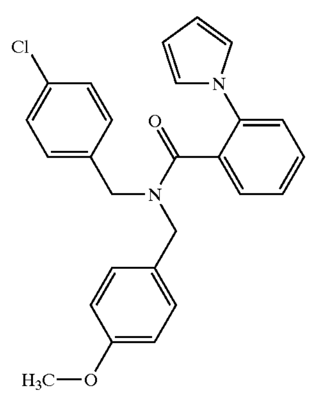 | N-(4-chlorobenzyl)-N-(4-methoxybenzyl)-2-(1H-pyrrol-1-yl)benzamide | 1.34 | 430.93 | 430.14 |

TABLE II-continued

| CMP# | STRUCTURE | IUPAC Name | LC (min.) | MW | LCMS |
|---|---|---|---|---|---|
| 174 | 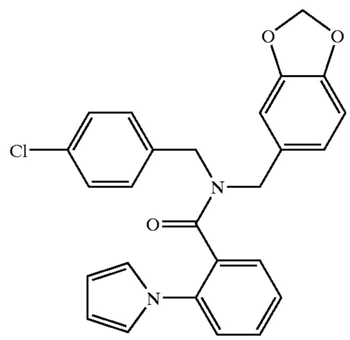 | N-(1,3-benzodioxol-5-ylmethyl)-N-(4-chlorobenzyl)-2-(1H-pyrrol-1-yl)benzamide | 1.33 | 444.92 | 444.12 |
| 175 | 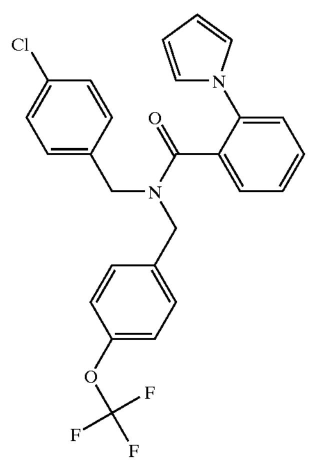 | N-(4-chlorobenzyl)-2-(1H-pyrrol-1-yl)-N-[4-(trifluoromethoxy)benzyl]benzamide | 1.37 | 484.90 | 484.12 |
| 176 | 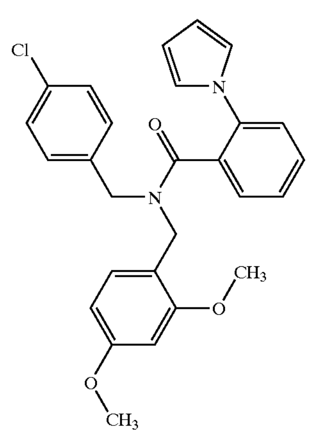 | N-(4-chlorobenzyl)-N-(2,4-dimethoxybenzyl)-2-(1H-pyrrol-1-yl)benzamide | 1.33 | 460.96 | 460.16 |

TABLE II-continued

| CMP# | STRUCTURE | IUPAC Name | LC (min.) | MW | LCMS |
|---|---|---|---|---|---|
| 177 | 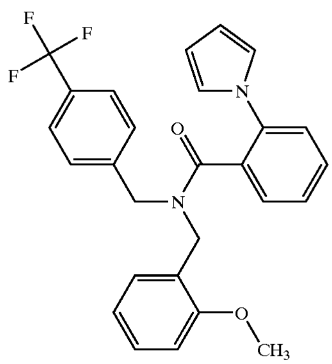 | N-(2-methoxybenzyl)-2-(1H-pyrrol-1-yl)-N-[4-(trifluoromethyl)benzyl]benzamide | 1.33 | 464.49 | 464.17 |
| 178 | 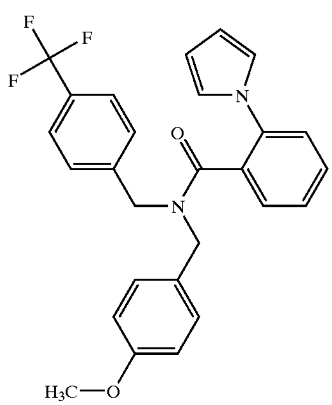 | N-(4-methoxybenzyl)-2-(1H-pyrrol-1-yl)-N-[4-(trifluoromethyl)benzyl]benzamide | 1.33 | 464.49 | 464.17 |
| 179 | 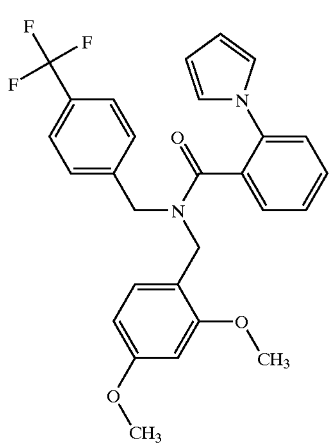 | N-(2,4-dimethoxybenzyl)-2-(1H-pyrrol-1-yl)-N-[4-(trifluoromethyl)benzyl]benzamide | 1.33 | 494.51 | 494.18 |

TABLE II-continued

| CMP# | STRUCTURE | IUPAC Name | LC (min.) | MW | LCMS |
|---|---|---|---|---|---|
| 180 | 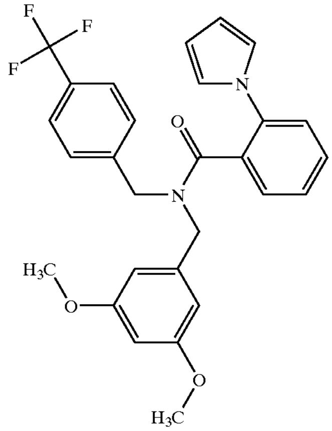 | N-(3,5-dimethoxybenzyl)-2-(1H-pyrrol-1-yl)-N-[4-(trifluoromethyl)benzyl]benzamide | 1.32 | 494.51 | 494.18 |
| 181 | 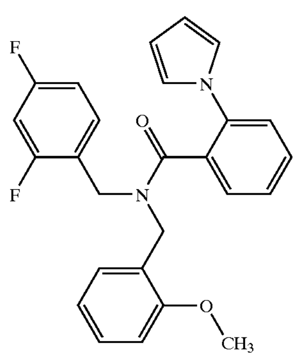 | N-(2-methoxybenzyl)-2-(1H-pyrrol-1-yl)-N-[2,4-(difluoro)benzyl]benzamide | 1.3 | 432.47 | 432.16 |
| 182 | 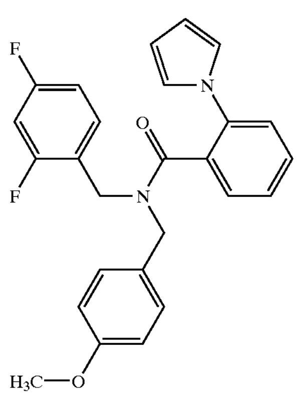 | N-(2,4-difluorobenzyl)-N-(4-methoxybenzyl)-2-(1H-pyrrol-1-yl)benzamide | 1.3 | 432.47 | 432.16 |

TABLE II-continued
| CMP# | STRUCTURE | IUPAC Name | LC (min.) | MW | LCMS |
|------|-----------|------------|-----------|-----|------|
| 183 | 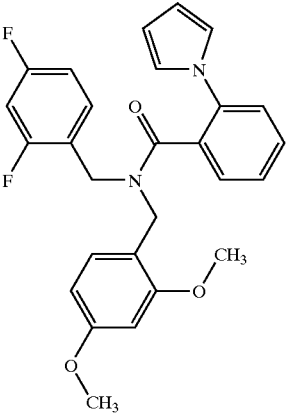 | N-(2,4-difluorobenzyl)-N-(2,4-dimethoxybenzyl)-2-(1H-pyrrol-1-yl)benzamide | 1.3 | 462.49 | 462.18 |
| 184 | 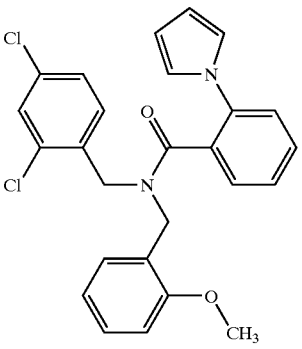 | N-(2,4-dichlorobenzyl)-N-(2-methoxybenzyl)-2-(1H-pyrrol-1-yl)benzamide | 1.38 | 465.38 | 464.11 |
| 185 | 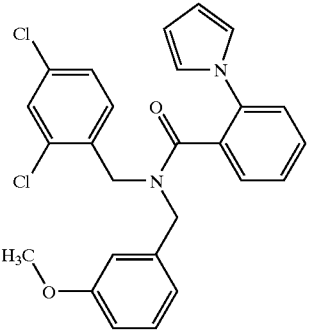 | N-(2,4-dichlorobenzyl)-N-(3-methoxybenzyl)-2-(1H-pyrrol-1-yl)benzamide | 1.37 | 465.38 | 464.11 |
| 186 | 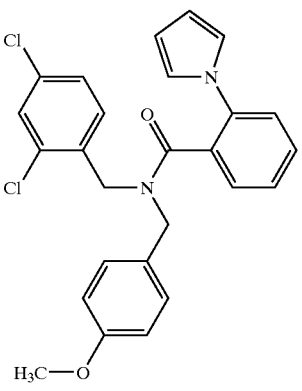 | N-(2,4-dichlorobenzyl)-N-(4-methoxybenzyl)-2-(1H-pyrrol-1-yl)benzamide | 1.37 | 465.38 | 464.11 |

TABLE II-continued

| CMP# | STRUCTURE | IUPAC Name | LC (min.) | MW | LCMS |
|---|---|---|---|---|---|
| 187 | 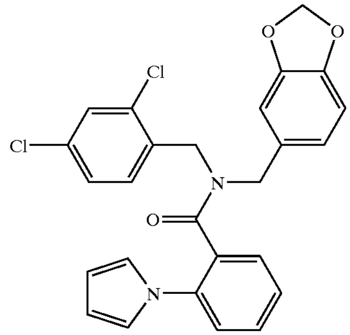 | N-(1,3-benzodioxol-5-ylmethyl)-N-(2,4-dichlorobenzyl)-2-(1H-pyrrol-1-yl)benzamide | 1.35 | 479.36 | 478.09 |
| 188 | 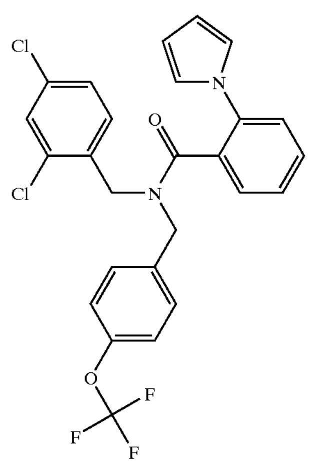 | N-(2,4-dichlorobenzyl)-2-(1H-pyrrol-1-yl)-N-[4-(trifluoromethoxy)benzyl]benzamide | 1.4 | 519.35 | 518.08 |
| 189 | 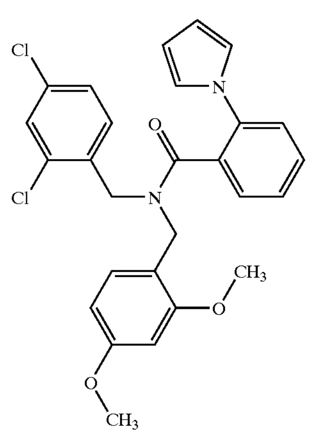 | N-(2,4-dichlorobenzyl)-N-(2,4-dimethoxybenzyl)-2-(1H-pyrrol-1-yl)benzamide | 1.36 | 495.40 | 494.12 |

TABLE II-continued

| CMP# | STRUCTURE | IUPAC Name | LC (min.) | MW | LCMS |
|---|---|---|---|---|---|
| 190 | 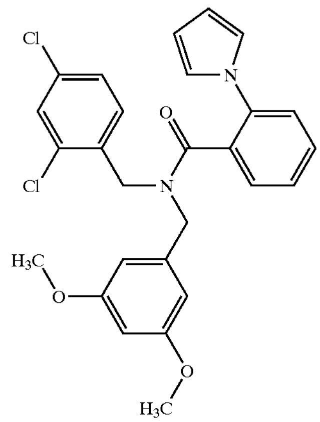 | N-(2,4-dichlorobenzyl)-N-(3,5-dimethoxybenzyl)-2-(1H-pyrrol-1-yl)benzamide | 1.37 | 495.40 | 494.12 |
| 191 | 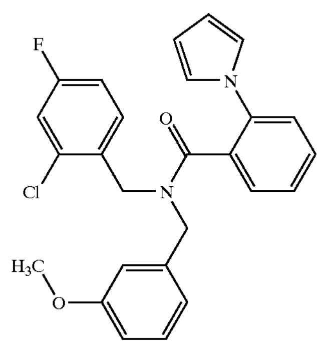 | N-(2-chloro-4-fluorobenzyl)-N-(3-methoxybenzyl)-2-(1H-pyrrol-1-yl)benzamide | 1.33 | 448.92 | 448.14 |
| 192 | 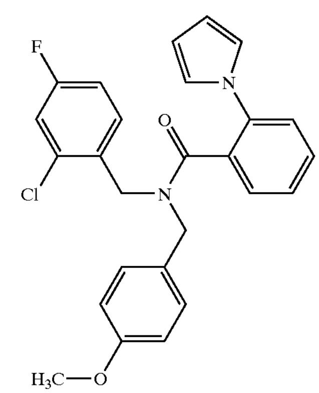 | N-(2-chloro-4-fluorobenzyl)-N-(4-methoxybenzyl)-2-(1H-pyrrol-1-yl)benzamide | 1.14 | 448.92 | 448.14 |
| 193 | 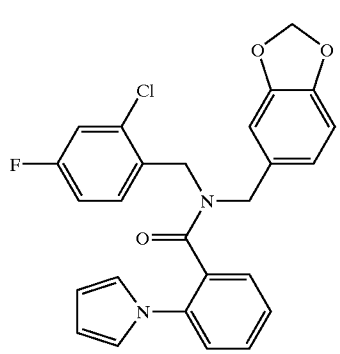 | N-(1,3-benzodioxol-5-ylmethyl)-N-(2-chloro-4-fluorobenzyl)-2-(1H-pyrrol-1-yl)benzamide | 1.32 | 462.91 | 462.11 |

TABLE II-continued

| CMP# | STRUCTURE | IUPAC Name | LC (min.) | MW | LCMS |
|------|-----------|------------|-----------|-----|------|
| 194 | 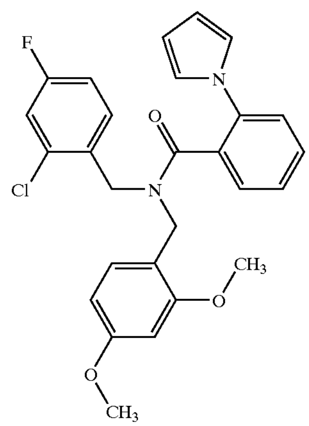 | N-(2-chloro-4-fluorobenzyl)-N-(2,4-dimethoxybenzyl)-2-(1H-pyrrol-1-yl)benzamide | 1.33 | 478.95 | 478.15 |
| 195 | 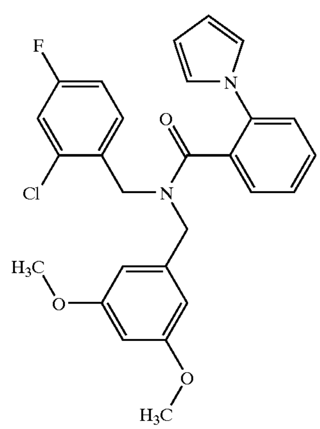 | N-(2-chloro-4-fluorobenzyl)-N-(3,5-dimethoxybenzyl)-2-(1H-pyrrol-1-yl)benzamide | 1.32 | 478.95 | 478.15 |
| 196 | 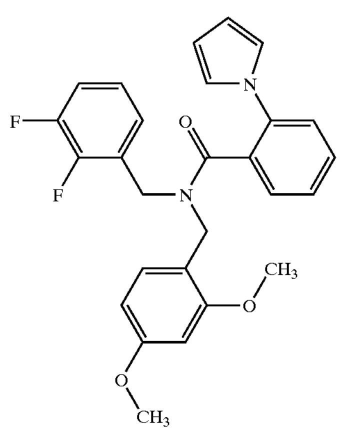 | N-(2,3-difluorobenzyl)-N-(2,4-dimethoxybenzyl)-2-(1H-pyrrol-1-yl)benzamide | 1.32 | 462.49 | 462.18 |

TABLE II-continued

| CMP# | STRUCTURE | IUPAC Name | LC (min.) | MW | LCMS |
|---|---|---|---|---|---|
| 197 | 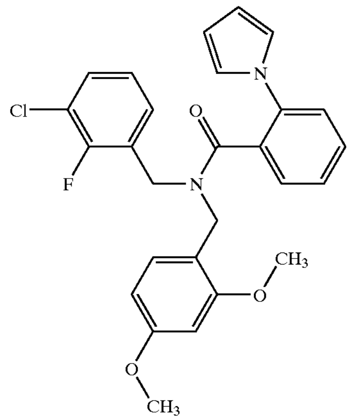 | N-(3-chloro-2-fluorobenzyl)-N-(2,4-dimethoxybenzyl)-2-(1H-pyrrol-1-yl)benzamide | 1.35 | 478.95 | 478.15 |
| 198 | 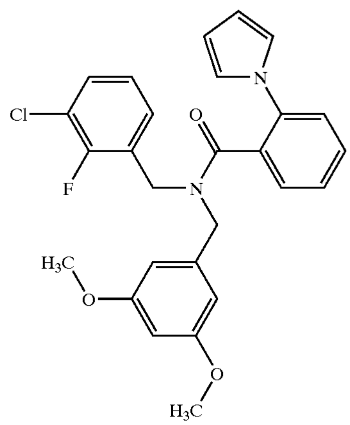 | N-(3-chloro-2-fluorobenzyl)-N-(3,5-dimethoxybenzyl)-2-(1H-pyrrol-1-yl)benzamide | 1.35 | 478.95 | 478.15 |
| 199 | 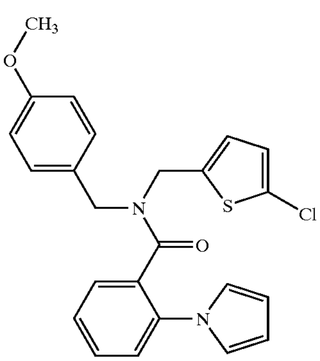 | N-[(5-chlorothien-2-yl)methyl]-N-(4-methoxybenzyl)-2-(1H-pyrrol-1-yl)benzamide | 1.34 | 436.96 | 436.10 |
| 200 | 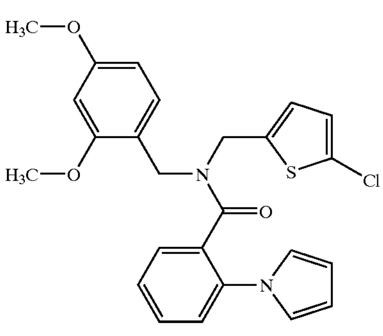 | N-[(5-chlorothien-2-yl)methyl]-N-(2,4-dimethoxybenzyl)-2-(1H-pyrrol-1-yl)benzamide | 1.34 | 466.99 | 466.11 |

TABLE II-continued

| CMP# | STRUCTURE | IUPAC Name | LC (min.) | MW | LCMS |
|---|---|---|---|---|---|
| 201 | 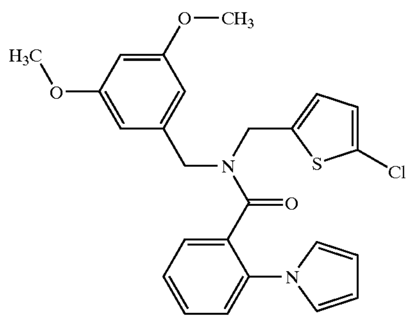 | N-[(5-chlorothien-2-yl)methyl]-N-(3,5-dimethoxybenzyl)-2-(1H-pyrrol-1-yl)benzamide | 1.34 | 466.99 | 466.11 |
| 202 | 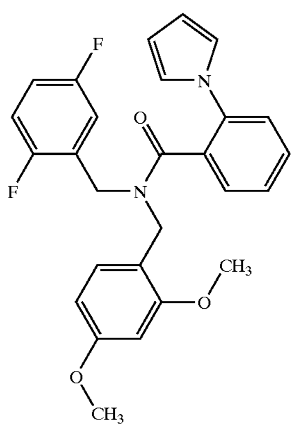 | N-(2,5-difluorobenzyl)-N-(2,4-dimethoxybenzyl)-2-(1H-pyrrol-1-yl)benzamide | 1.31 | 462.49 | 462.18 |
| 203 | 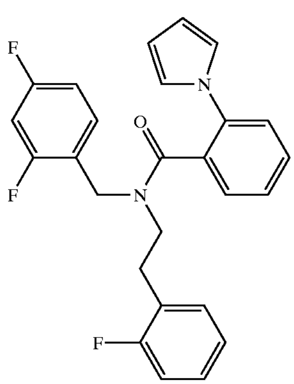 | N-(2,4-difluorobenzyl)-N-[2-(2-fluorophenyl)ethyl]-2-(1H-pyrrol-1-yl)benzamide | 1.34 | 434.46 | 434.16 |
| 204 | 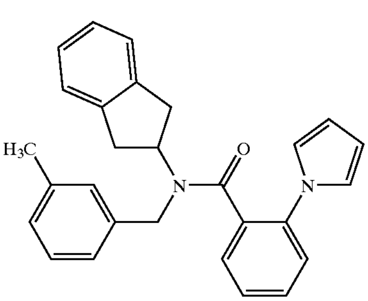 | N-(indan-2-yl)-N-(3-methylbenzyl)-2-(1H-pyrrol-1-yl)benzamide | 1.19 | 406.53 | 406.20 |

TABLE II-continued
| CMP# | STRUCTURE | IUPAC Name | LC (min.) | MW | LCMS |
|---|---|---|---|---|---|
| 205 | 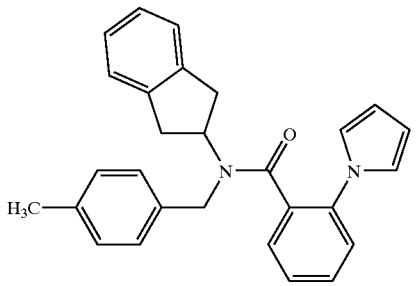 | N-(indan-2-yl)-N-(4-methylbenzyl)-2-(1H-pyrrol-1-yl)benzamide | 1.34 | 406.53 | 406.20 |
| 206 | 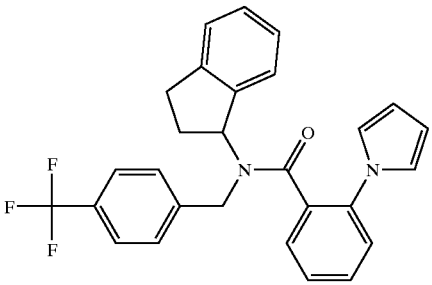 | N-(indan-1-yl)-2-(1H-pyrrol-1-yl)-N-[4-(trifluoromethyl)benzyl]benzamide | 1.33 | 460.50 | 460.18 |
| 207 | 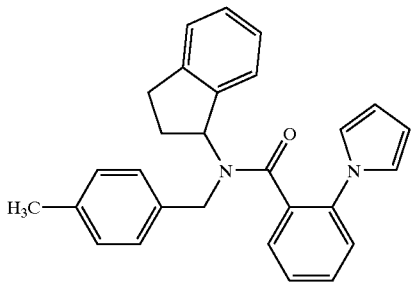 | N-(2,3-dihydro-1H-inden-1-yl)-N-(4-methylbenzyl)-2-(1H-pyrrol-1-yl)benzamide | 1.35 | 406.53 | 406.20 |
| 208 | 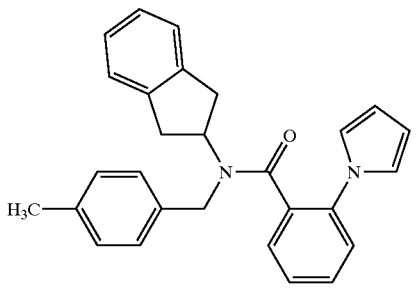 | N-Indan-2-yl-N-(4-methyl-benzyl)-2-pyrrol-1-yl-benzamide | 1.32 | 406.53 | 406.20 |
| 209 | 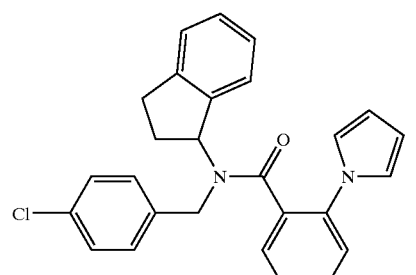 | N-(4-chlorobenzyl)-N-(2,3-dihydro-1H-inden-1-yl)-2-(1H-pyrrol-1-yl)benzamide | 1.35 | 426.95 | 426.15 |

TABLE II-continued

| CMP# | STRUCTURE | IUPAC Name | LC (min.) | MW | LCMS |
|---|---|---|---|---|---|
| 210 | 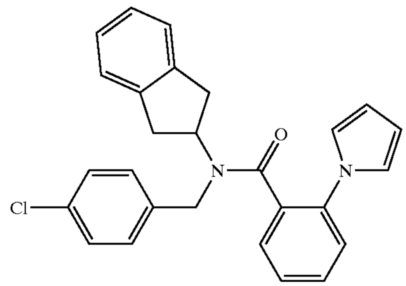 | N-(4-chlorobenzyl)-N-(indan-2-yl)-2-(1H-pyrrol-1-yl)benzamide | 1.34 | 426.95 | 426.15 |
| 211 | 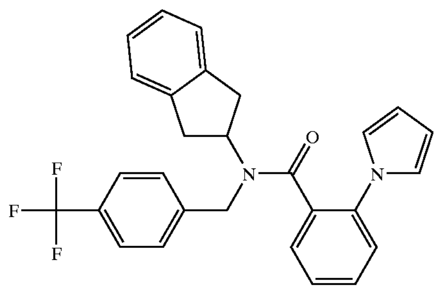 | N-(indan-2-yl)-2-(1H-pyrrol-1-yl)-N-[4-(trifluoromethyl)benzyl]benzamide | 1.31 | 460.50 | 460.18 |
| 212 | 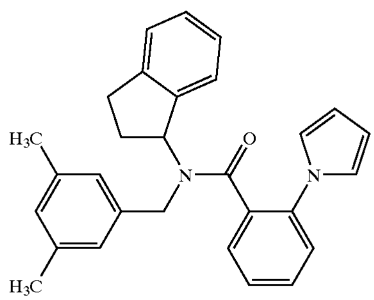 | N-(2,3-dihydro-1H-inden-1-yl)-N-(3,5-dimethylbenzyl)-2-(1H-pyrrol-1-yl)benzamide | 1.38 | 420.55 | 420.22 |
| 213 | 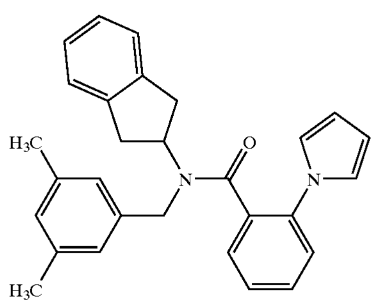 | N-(indan-2-yl)-N-(3,5-dimethylbenzyl)-2-(1H-pyrrol-1-yl)benzamide | 1.18 | 420.55 | 420.22 |
| 214 | 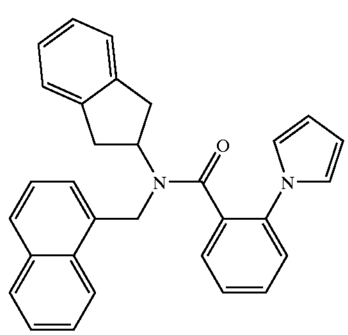 | N-(indan-2-yl)-N-(1-naphthylmethyl)-2-(1H-pyrrol-1-yl)benzamide | 1.36 | 442.56 | 442.20 |

TABLE II-continued

| CMP# | STRUCTURE | IUPAC Name | LC (min.) | MW | LCMS |
|---|---|---|---|---|---|
| 215 | 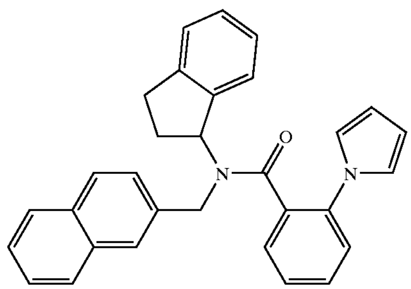 | N-(2,3-dihydro-1H-inden-1-yl)-N-(2-naphthylmethyl)-2-(1H-pyrrol-1-yl)benzamide | 1.36 | 442.56 | 442.20 |
| 216 | 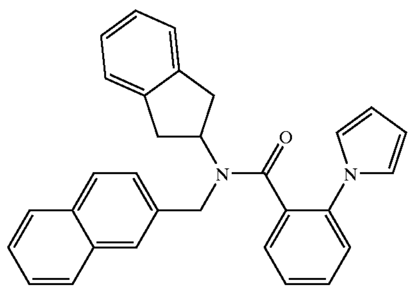 | N-(indan-2-yl)-N-(2-naphthylmethyl)-2-(1H-pyrrol-1-yl)benzamide | 1.36 | 442.56 | 442.20 |

TABLE III

| CMP # | STRUCTURE | IUPAC NAME | Ca2+ Mob. | LC-MS | NMR |
|---|---|---|---|---|---|
| 217 | 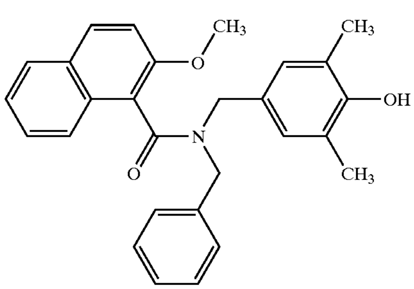 | N-benzyl-N-(4-hydroxy-3,5-dimethylbenzyl)-2-methoxy-1-naphthamide | * | 423 | $^1$H-NMR (δ, CDCl$_3$): 7.85(dd, J=9, 5Hz, 1H), 7.74–7.9(m, 2H), 7.47(d, J=7Hz, 1H), 7.06–7.42(m, 9H), 7.04(s, 1H), 6.60(s, 1H), 4.93(d, J=15Hz, 1H), 4.70(d, J=15Hz, 1H), 4.03–4.18(m, 2H), 3.98(s, 3H, OMe), 2.28(s, 3H, Me), 2.11(s, 3H, Me). |
| 218 | 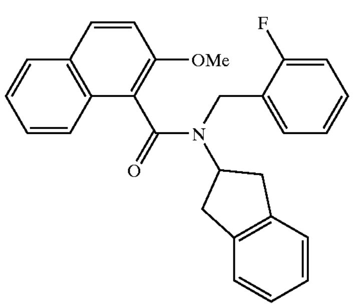 | 2-Methoxy-naphthalene-1-carboxylic acid(2-fluoro-benzyl)-indan-2-yl-amide | | | |

TABLE III-continued

| CMP # | STRUCTURE | IUPAC NAME | Ca2+ Mob. | LC-MS | NMR |
|---|---|---|---|---|---|
| 219 | 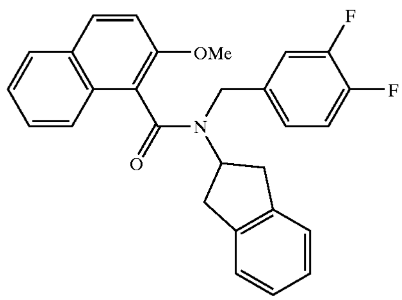 | 2-Methoxy-naphthalene-1-carboxylic acid(3,4-difluoro-benzyl)-indan-2-yl-amide | | 444 | 1H-NMR (δ, CDCl3): 7.88(1H, d, J=9Hz), 7.81(d, J=8Hz, 1H), 7.71(d, J=8Hz, 1H), 7.52(t, J=7Hz, 1H), 7.54–6.99(m, 9H), 5.30(d, J=16Hz, 1H), 4.59(t, J=8Hz, 1H), 7.40(d, J=16Hz, 1H), 4.06(s, 3H, OMe), 3.00(dd, J=8Hz, 1H), 2.87(d, J=8Hz, 2H), 2.74(d, J=8Hz, 1H). |
| 220 | 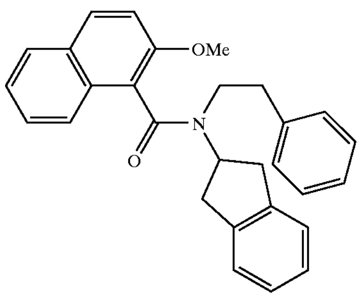 | 2-Methoxy-naphthalene-1-carboxylic acid indan-2-yl-phenethyl-amide | * | | |
| 221 | 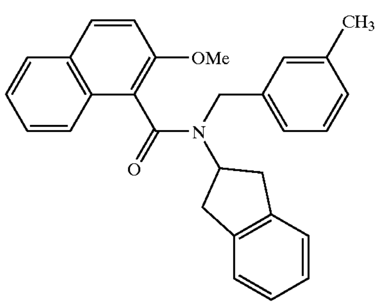 | 2-Methoxy-naphthalene-1-carboxylic acid(3-methyl-benzyl)-indan-2-yl-amide | * | 422 | 1H-NMR (δ, CDCl3): 7.85(1H, d, J=9Hz), 7.81–7.70(m, 2H), 7.50(t, J=7Hz, 1H), 7.45–6.80(m, 10H), 5.19(d, J=16Hz, 1H), 4.55–4.65t(m, 2H), 4.04(s, 3H, OMe), 2.92–3.05(m, 2H), 2.86(dd, J=16, 8Hz, 1H), 2.65(dd, J=16, 8Hz, 1H), 2.38(s, 3H, Me). |
| 222 | 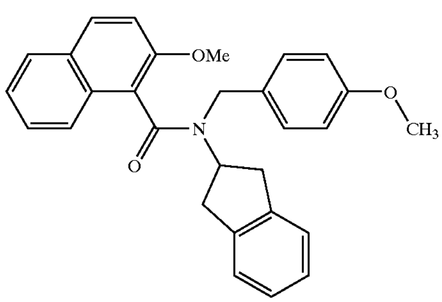 | 2-Methoxy-naphthalene-1-carboxylic acid(4-methoxy-benzyl)-indan-2-yl-amide | | | |
| 223 | 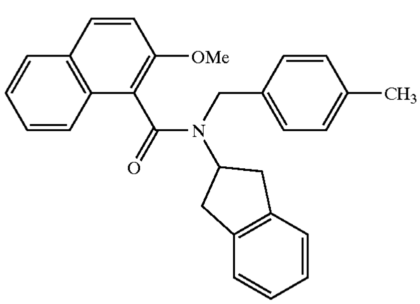 | 2-Methoxy-naphthalene-1-carboxylic acid(4-methyl-benzyl)-indan-2-yl-amide | * | 422 | |

TABLE III-continued

| CMP # | STRUCTURE | IUPAC NAME | Ca2+ Mob. | LC-MS | NMR |
|---|---|---|---|---|---|
| 224 | 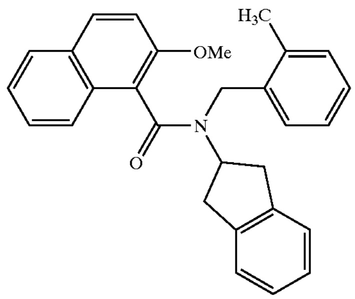 | 2-Methoxy-naphthalene-1-carboxylic acid(2-methyl-benzyl)-indan-2-yl-amide | * | | |
| 225 | 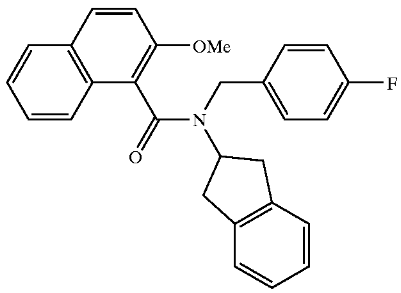 | 2-Methoxy-naphthalene-1-carboxylic acid(4-fluoro-benzyl)-indan-2-yl-amide | | 426. | |
| 226 | 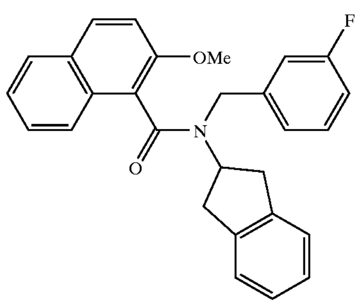 | 2-Methoxy-naphthalene-1-carboxylic acid(3-fluoro-benzyl)-indan-2-yl-amide | | 426 | 1H-NMR (δ, CDCl3): 7.88(d, J=9Hz, 1H), 7.81(d, J=8Hz, 1H), 7.75(d, J=8Hz, 1H), 7.52(t, J=7Hz, 1H), 7.39(t, J=8Hz, 1H), 7.25–7.33(m, 4H), 6.94–7.15(m, 5H), 5.34(d, J=16Hz, 1H), 4.61(t, J=16Hz, 1H), 4.50(d, J=16Hz, 1H), 4.07(s, 3H, OMe), 3.02(dd, J=16, 8Hz, 1H), 2.89(dd, J=8, 4Hz, 1H), 2.72(dd, J=16, 8Hz, 1H). |
| 227 | 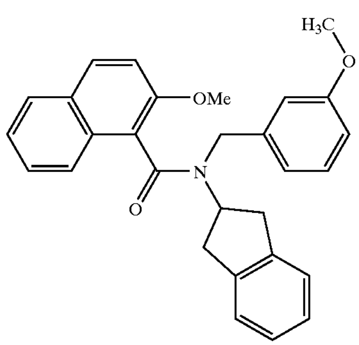 | 2-Methoxy-naphthalene-1-carboxylic acid(3-methoxy-benzyl)-indan-2-yl-amide | | 438 | |
| 228 | 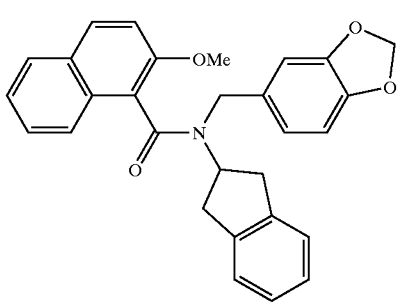 | 2-Methoxy-naphthalene-1-carboxylic acid benzo[1,3]dioxol-5-ylmethyl-indan-2-yl-amide | * | 452 | 1H-NMR (δ, CDCl3): 7.68–8.12(m, 4H), 7.01–7.56(m, 8H), 6.78(d, J=4Hz, 1H), 5.97(dd, J=9, 1HZ, 1H), 5.19(d, J=16Hz, 1H), 4.57(t, J=8Hz, 1H), 4.50(d, J=16Hz, 1H), 4.04(s, #H, OMe), 2.95–3.07(m, 2H), 2.86(dd, J=16, 8Hz, 1H), 2.69(dd, J=16, 8Hz, 1H). |

TABLE III-continued

| CMP # | STRUCTURE | IUPAC NAME | Ca2+ Mob. | LC-MS | NMR |
|---|---|---|---|---|---|
| 229 | 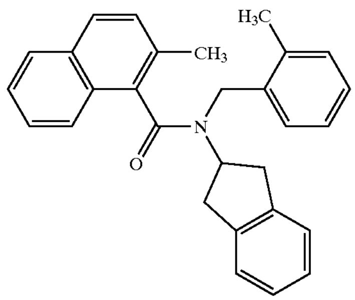 | 2-Methyl-naphthalene-1-carboxylic acid(2-methyl-benzyl)-indan-2-yl-amide | | 406 | |
| 230 | 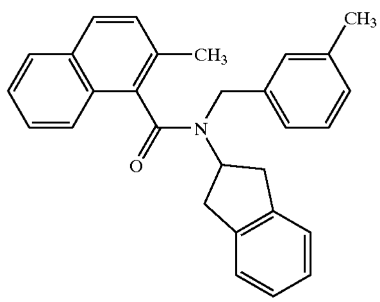 | 2-Methyl-naphthalene-1-carboxylic acid(3-methyl-benzyl)-indan-2-yl-amide | * | 406. | |
| 231 | 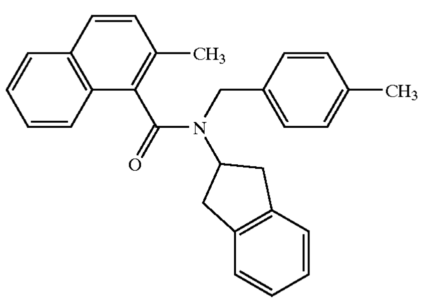 | 2-Methyl-naphthalene-1-carboxylic acid(4-methyl-benzyl)-indan-2-yl-amide | | 406 | |
| 232 | 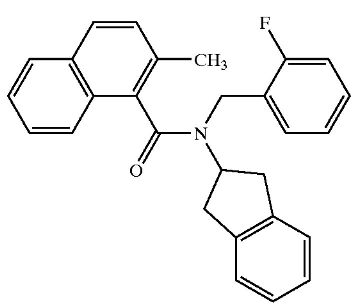 | 2-Methyl-naphthalene-1-carboxylic acid(2-fluoro-benzyl)-indan-2-yl-amide | | 426 | 1H-NMR (δ, CDCl3): 7.87(d, J=9Hz, 1H), 7.70–7.83(m, 3H), 7.53(t, J=7Hz, 1H), 7.13–7.41(m, 5H), 6.96–7.05(m, 4H), 5.31(d, J=15Hz, 1H), 4.72(d, J=15Hz, 1H), 4.61(t, J=9Hzx, 1H), 4.06(d, J=1Hz, 3H, OMe), 3.07(dd, J=16, 9Hx, 1H) 2.94(dd, J=16, 9Hz, 1H), 2.85(dd, J=16, 8Hz, 1h), 2.66(DD, j=16, 8Hz, 1H). |
| 233 | 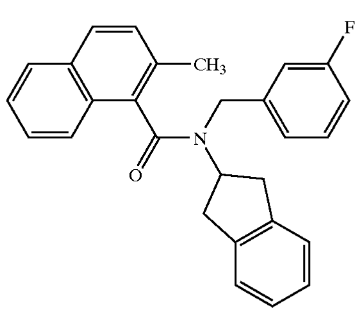 | 2-Methyl-naphthalene-1-carboxylic acid(3-fluoro-benzyl)-indan-2-yl-amide | | | |

TABLE III-continued

| CMP # | STRUCTURE | IUPAC NAME | Ca2+ Mob. | LC-MS | NMR |
|---|---|---|---|---|---|
| 234 | 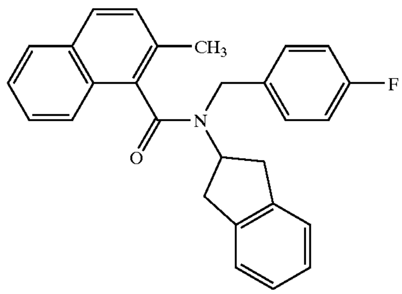 | 2-Methyl-naphthalene-1-carboxylic acid(4-fluoro-benzyl)-indan-2-yl-amide | | 410 | 1H-NMR (δ, CDCl3): 7.85–7.73(m, 3H), 7.44–7.55(m, 2H), 7.33–7.40(m, 2H), 7.01–7.25(m, 6H), 6.83–6.86(m, 1H), 4.99(d, J=15Hz, 1H), 4.70(d, J=15Hz, 1H), 4.48(t, J=7Hz, 1H), 2.96–3.02(dd, J=16, 7Hz, 2H), 2.90(dd, J=16, 8Hz, 1H), 2.70(dd, J=16, 8Hz, 1H), 2.56(S, 3h, Me). |
| 235 | 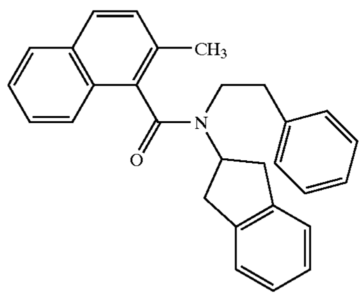 | 2-Methyl-naphthalene-1-carboxylic acid indan-2-yl-phenethyl-amide | * | 422 | 1H-NMR (δ, CDCl3): 7.86(d, J=10Hx, 1H), 7.79(d, J=8Hz, 1H), 7.71(t, J=8Hz, 1H), 7.50(m, 1H), 7.20–7.39(m, 7H), 6.97–7.14(m, 4H), 4.44(t, J=8Hz, 1H), 4.00(s, 3H, OMe), 3.73(m, 2H), 3.24–3.31(m, 1H), 3.10–3.19(m, 1H), 2.92–3.09(m, 1H), 2.75(dd, J=8Hz, 1H). |
| 236 | 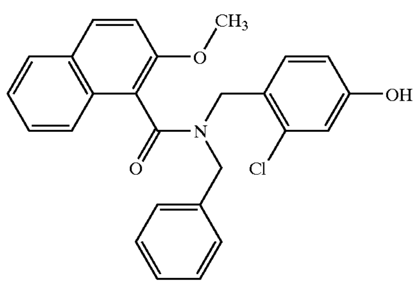 | Naphthalene-1-carboxylic acid benzyl-(2-chloro-4-hydroxy-benzyl)-amide | * | | |
| 237 | 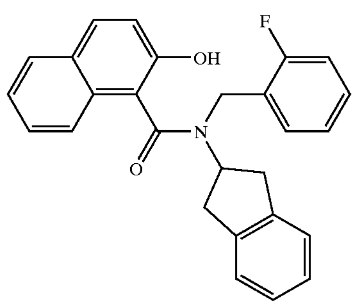 | 2-Hydroxy-naphthalene-1-carboxylic acid(2-fluoro-benzyl)-indan-2-yl-amide | * | | |
| 238 | 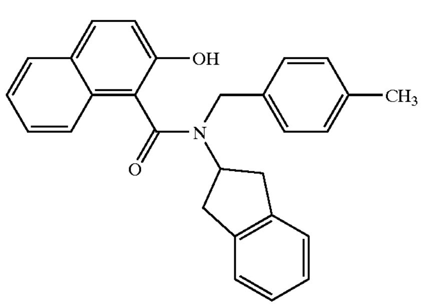 | 2-Hydroxy-naphthalene-1-carboxylic acid(4-methyl-benzyl)-indan-2-yl-amide | * | | |

TABLE III-continued

| CMP # | STRUCTURE | IUPAC NAME | Ca2+ Mob. | LC-MS | NMR |
|---|---|---|---|---|---|
| 239 | 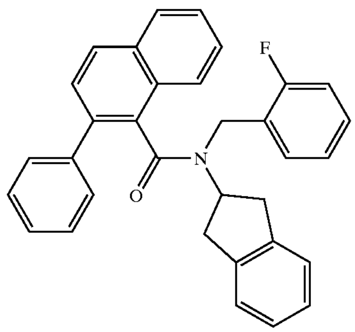 | 2-Phenyl-naphthalene-1-carboxylic acid(2-fluoro-benzyl)-indan-2-yl-amide | * | | |
| 240 | 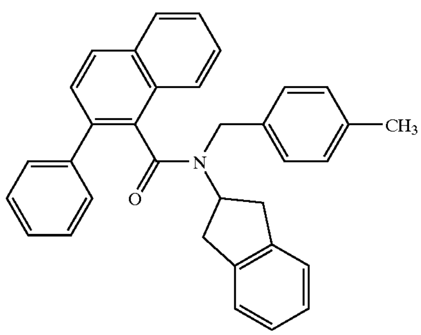 | 2-Phenyl-naphthalene-1-carboxylic acid(4-methyl-benzyl)-indan-2-yl-amide | * | | |
| 241 | 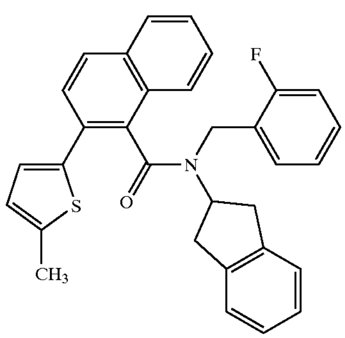 | 2-(5-Methyl-thiopben-2-yl)-naphthalene-1-carboxylic acid(2-fluoro-benzyl)-indan-2-yl-amide | * | | |
| 242 | 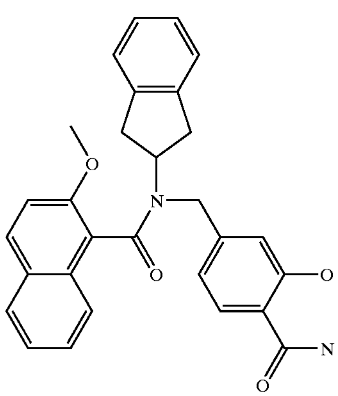 | 2-Methoxy-naphthalene-1-carboxylic acid(4-carbamoyl-3-hydroxy-benzyl)-indan-2-yl-amide | | | |

TABLE III-continued

| CMP # | STRUCTURE | IUPAC NAME | Ca2+ Mob. | LC-MS | NMR |
|---|---|---|---|---|---|
| 243 | 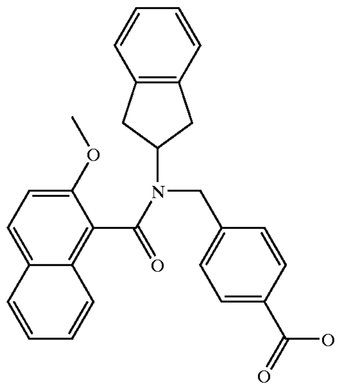 | 4-{[Indan-2-yl-(2-methoxy-naphthalene-1-carbonyl)-amino]-methyl}-benzoic acid | | | |

Example 11

Pharmaceutical Preparations of Oral and Intravenous Administration

A. Tablets containing a C5a antagonist and an anti-arthritic agent which is not a C5a receptor antagonist can be prepared as illustrated below:

| Ingredient | Amount |
|---|---|
| C5a receptor antagonist | 5 mg–500 mg |
| C5a receptor-inactive therapeutic agent | 1 mg–500 mg |
| diluent, binder, disintigrant, lubricant excipients | q.s. 200–400 mg. |

B. Tablets containing a C5a receptor antagonist as the only active ingredient can be prepared as illustrated below:

| Ingredient | mg | mg |
|---|---|---|
| C5a receptor antagonist | 10 | 50 |
| Microcrystalline Cellulose | 70.4 | 352 |
| Grannular Mannitol | 15.1 | 75.5 |
| Croscarmellose Sodium | 3.0 | 15.0 |
| Colloidal Silicon Dioxide | 0.5 | 2.5 |
| Magnesium Stearate (Impalpable Powder) | 1.0 | 5.0 |
| Total (mg) | 100 | 500 |

C. Tablets containing a C5a receptor antagonist and a C5a receptor inactive agent may be prepared as follows:

| Ingredient | mg | mg |
|---|---|---|
| C5a receptor antagonist | 10 | 25 |
| C5a receptor inactive therapeutic agent | 10 | 25 |
| Microcrystalline Cellulose | 40 | 100 |
| Modified food corn starch | 1.05 | 4.25 |
| Magnesium stearate | 1.25 | 0.5 |

D. Intravenous formulations containing a C5a receptor antagonist and a C5a receptor inactive agent may be prepared as follows:

| Ingredient | Amount |
|---|---|
| C5a receptor antagonist | 0.5–10 mg |
| C5a receptor inactive therapeutic agent | 0.5–10 mg |
| Sodium Citrate | 5–50 mg |
| Citric Acid | 1–15 mg |
| Sodium Chloride | 1–8 mg |
| Water for Injection | to 1.0 liter |

E. Oral suspensions containing a C5a receptor antagonist and a C5a receptor inactive agent may be prepared as follows:

| Ingredient | Amount per 5 ml dose |
|---|---|
| C5a receptor antagonist | 5–100 mg |
| C5a receptor inactive therapeutic agent | 5–100 mg |
| Polyvinylpyrrolidone | 150 mg |
| Poly oxyethylene sorbitan monolaurate | 25 mg |
| Benzoic Acid | 10 mg to 5 mL with sorbitol solution (70%) |

Example 12

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.;

ChemSyn Laboratories, Lexena, Kans.; American Radiolabeled Chemicals, Inc., St. Louis, Mo.; and Moravek Biochemicals Inc., Brea, Calif.

For example, alpha-Napthoic acid, [1-$^{14}$C] (Available from American Radiolabeled Chemicals, St. Louis, Mo., Product No. ARC-153) may be used as a starting material in the to obtain many of the biarylamides provided herein using the method shown in Scheme 2.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 13

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Examples.

Example 14

Assay for C5a Receptor Mediated Chemotaxis

This assay is a standard assay of C5a receptor mediated chemotaxis.

Human promonocytic U937 cells or purified human or non-human neutrophils are treated with dibutyryl cAMP for 48 hours prior to performing the assay. Human neutrophils or those from another mammalian species are used directly after isolation. The cells are pelleted and resuspended in culture media containing 0.1% fetal bovine serum (FBS) and 10 ug/ml calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately 3×10$^6$ cells/mL. Aliquots of this cell suspension are transferred to clean test tubes, which contain vehicle (1% DMSO) or varying concentrations of a compound of interest, and incubated at room temperature for at least 30 minutes. The chemotaxis assay is performed in CHEMO TX 101–8, 96 well plates (Neuro Probe, Inc. Gaithersburg, Md.). The bottom wells of the plate are filled with medium containing 0–10 nM of C5a, preferably derived from the same species of mammal as are the neutrophils or other cells (e.g., human C5a for the human U937 cells). The top wells of the plate are filled with cell suspensions (compound or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an IC$_{50}$ value.

As a control to ensure that cells retain chemotactic ability in the presence of the compound of interest, the bottom wells of the plate may be filled with varying concentrations chemo-attractants that do not mediate chemotaxis via the C5a receptor (e.g., zymosan-activated serum (ZAS), N-formylmethionyl-leucyl-phenylalanine (FMLP) or leukotriene B4 (LTB4)), rather than C5a, under which conditions the compounds provided herein preferably do not inhibit chemotaxis.

Preferred compounds exhibit IC$_{50}$ values of less than 1 μM in the above assay for C5a receptor mediated chemotaxis.

Example 15

Expression of a C5a Receptor

A human C5a receptor cDNA is obtained by PCR using 1) a forward primer adding a Kozak ribosome binding site and 2) a reverse primer that added no additional sequence, and 3) an aliquot of a Stratagene Human Fetal Brain cDNA library as template. The sequence of the resulting PCR product is as described by Gerard and Gerard, (1991) *Nature* 349:614–17. The PCR product is subcloned into the cloning vector pCR-Script AMP (STRATAGENE, La Jolla, Calif.) at the Srf I site. It is then excised using the restriction enzymes EcoRI and NotI and subcloned in the appropriate orientation for expression into the baculoviral expression vector pBac-PAK 9 (CLONTECH, Palo Alto, Calif.) that has been digested with EcoRI and NotI.

Example 16

Baculoviral Preparations for C5a Expression

The human C5a (hC5a) receptor baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Lenexa, Kans.) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing 2×10$^6$ Sf9 cells in 5 mls of insect medium. After five days of incubation at 27° C., supernatant medium is harvested from each of the T25 infections for use as passage 1 inoculum.

Two of seven recombinant baculoviral clones are then chosen for a second round of amplification, using 1 ml of passage 1 stock to infect 1×10$^8$ cells in 100 ml of insect medium divided into 2 T175 flasks. Forty-eight hours post infection, passage 2 medium from each 100 ml prep is harvested and plaque assayed for titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post-infection the supernatant medium is harvested to yield passage 3 baculoviral stock.

The remaining cell pellet is assayed for affinity binding using the "Binding Assays" essentially as described by DeMartino et al. (1994) *J. Biol. Chem.* 269:14446–50 at page 14447, adapted as follows. Radioligand is 0.005–0.500 nM [$^{125}$I]C5a (human recombinant; New England Nuclear Corp., Boston, Mass.); the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/ml aprotinin; filtration is carried out using GF/C WHATMAN filters (presoaked in 1.0% polyethyeneimine for 2 hours prior to use); and the filters are washed twice with 5 mLs cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression. A multiplicity of infection of 0.1 and a 72-hour incubation were the best infection parameters found for hC5a receptor expression in up to 1-liter Sf9 cell infection cultures.

Example 17

Baculoviral Infections

Log-phase Sf9 cells (INVITROGEN Corp., Carlsbad, Calif.) are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $G\square_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V6B003), all of which may be obtained from BIOSIGNAL Inc. (Montreal, Canada).

The infections are conveniently carried out at a multiplicity of infection of 0.1:1.0:0.5:0.5. At 72 hours post-infection, a sample of cell suspension is analyzed for viability by trypan blue dye exclusion, and the remaining Sf9 cells are harvested via centrifugation (3000 rpm/10 minutes/4° C.).

Example 18

Purified Recombinant Insect Cell Membranes

Sf9 cell pellets are resuspended in homogenization buffer (10 mM HEPES, 250 mM sucrose, 0.5 ug/ml leupeptin, 2 ug/ml Aprotinin, 200 uM PMSF, and 2.5 mM EDTA, pH 7.4) and homogenized using a POLYTRON homogenizer (setting 5 for 30 seconds). The homogenate is centrifuged (536×g/10 minutes/4° C.) to pellet the nuclei. The supernatant containing isolated membranes is decanted to a clean centrifuge tube, centrifuged (48,000×g/30 minutes, 4° C.) and the resulting pellet resuspended in 30 ml homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100–150 mg of total membrane protein.

Example 19

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, o.1% BSA, pH 7.4, 0.1 mM bacitracin, 100 KIU/ml aprotinin).

For saturation binding analysis, membranes (5–50 μg) are added to polypropylene tubes containing 0.005–0.500 nM [$^{125}$I]C5a (human (recombinant), New England Nuclear Corp., Boston, Mass.). Nonspecific binding is determined in the presence of 300 nM hC5a (Sigma Chemical Co., St. Louis, Mo.) and accounts for less than 10% of total binding. For evaluation of guanine nucleotide effects on receptor affinity, GTPγS is added to duplicate tubes at the final concentration of 50 μM.

For competition analysis, membranes (5–50 μg) are added to polypropylene tubes containing 0.030 nM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounts for less than 10% of total binding. Following a 2-hour incubation at room temperature, the reaction is terminated by rapid vacuum filtration. Samples are filtered over presoaked (in 1.0% polyethyleneimine for 2 hours prior to use) GF/C WHATMAN filters and rinsed 2 times with 5 mLs cold binding buffer without BSA, bacitracin, or aprotinin. Remaining bound radioactivity is quantified by gamma counting. $K_I$ and Hill coefficient ("nH") are determined by fitting the Hill equation to the measured values with the aid of SIGMA-PLOT software (SPSS Inc., Chicago, Ill.).

Example 20

Agonist-induced GTP Binding

Agonist-stimulated GTP-gamma $^{35}$S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the hC5a receptor and three directing the expression of each of the three subunits of a heterotrimeric G-protein) are used to infect a culture of Sf9 cells as described in Example 17.

Agonist-stimulated GTP binding on purified membranes (prepared as described in Example 18) is assessed using hC5a (Sigma Chemical Co., St. Louis, Mo.) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pH 7.0, 120 mM NaCl, 2 mM MgCl2, 2 mM EGTA, 0.1% BSA, 0.1 mM bacitracin, 100 KIU/mL aprotinin, 5 μM GDP) and added to reaction tubes at a concentration of 30 μg protein/reaction tube. After adding increasing doses of the agonist hC5a at concentrations ranging from $10^{-12}$ M to $10^{-6}$ M, reactions are initiated by the addition of 100 pM GTP-gamma $^{35}$S. In competition experiments, non-radiolabeled test compounds are added to separate assays at concentrations ranging from $10^{-10}$ M to $10^{-5}$ M along with 10 nM hC5a to yield a final volume of 0.25 mL.

Neutral antagonists are those test compounds that reduce the C5a-stimulated GTP binding activity towards, but not below, baseline (the level of GTP bound by membranes in this assay in the absence of added C5a or other agonist and in the further absence of any test compound).

In contrast, in the absence of added C5a certain preferred compounds will reduce the GTP binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound that elevates GTP binding activity above baseline in the absence of added hC5a in this GTP binding assay is characterized as having partial agonist activity. Preferred antagonist compounds do not elevate GTP binding activity under such conditions more than 10%, 5% or 2% above baseline.

Following a 60-minute incubation at room temperature, the reactions are terminated by vacuum filtration over GF/C filters (pre-soaked in wash buffer, 0.1% BSA) followed by washing with ice-cold wash buffer (50 mM Tris pH 7.0, 120mM NaCl). The amount of receptor-bound (and thereby membrane-bound) GTP-gamma $^{35}$S is determined by measuring the bound radioactivity, preferably by liquid scintillation spectrometry of the washed filters. Non-specific binding is determined using 10 mM GTP-gamma $^{35}$S and typically represents less than 5 percent of total binding. Data is expressed as percent above basal (baseline). The results of these GTP binding experiments may be conveniently analyzed using SIGMAPLOT software.

Example 21

Calcium Mobilization Assays

A. Response to C5a

U937 cells are grown in differentiation media (1 mM dibutyrl cAMP in RPMI 1640 medium containing 10% fetal bovine serum) for 48 hrs at 37° C. then reseeded onto 96-well plates suitable for use in a FLIPR™ Plate Reader (Molecular Devices Corp., Sunnyvale, Calif.). Cells are grown an additional 24 hours (to 70–90% confluence) before the assay. The cells are then washed once with Krebs Ringer solution. FLUO-3 calcium sensitive dye (Molecular Probes, Inc. Eugene, Oreg.) is added to 10 µg/mL and incubated with the cells at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01–30.0 nM, using the FLIPR™ device (Molecular Devices). Differentiated U937 cells typically exhibit signals of 5,000–50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 µM. This stimulation typically triggers a signal of 1,000 to 12,000 arbitrary fluorescence light units. Certain preferred compounds produce less than a 10%, less than a 5%, or less than a 2% alteration of this calcium mobilization signal when this control assay is carried out in the presence of the compound, as compared to the signal when the assay is performed in the absence of the compound.

C. Assays for the Identification of Receptor Modulatory Agents: Antagonists and Agonists The calcium mobilization assay described above may be readily adapted for identifying test compounds that have agonist or antagonist activity at the human C5a receptor.

For example, in order to identify antagonist compounds, differentiated U937 cells are washed and incubated with Fluo-3 dye as described above. One hour prior to measuring the fluorescence signal, a subset of the cells is incubated with 1 µM of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

Example 22

Assays to Evaluate Agonist Activity of Small Molecule C5a Receptor Antagonists

Preferred compounds provided herein are C5a receptor antagonists that do not possess significant (e.g., greater than 5%) agonist activity in any of the C5a mediated functional assays discussed herein. Specifically, this undesired agonist activity can be evaluated, for example, in the GTP binding assay of Example 20, by measuring small molecule mediated GTP binding in the absence of the natural agonist, C5a. Similarly, in a calcium mobilization assay (e.g., that of Example 21), a small molecule compound can be directly assayed for the ability of the compound to stimulate calcium levels in the absence of the natural agonist, C5a. The preferred extent of C5a agonist activity exhibited by compounds provided herein is less than 10%, more preferably less than 5% and most preferably less than 2% of the response elicited by the natural agonist, C5a.

The foregoing description is illustrative thereof, and it will be understood that variations and modifications can be effected without departing from the scope or spirit of the invention as set forth in the following Claims.

What is claimed is:

1. A compound of the formula:

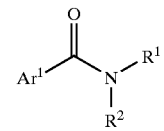

or a pharmaceutically acceptable salt thereof, wherein $Ar^1$ is optionally substituted phenyl having at least one optionally substituted heterocyclic substituent attached thereto at the 2-position relative to the point of attachment, wherein the heterocyclic substituent is chosen from imidazoloyl, pyrrolyl, pyrazolyl, oxazolyl, thiazolyl and pyrimidinyl;

$R^1$ is optionally substituted cycloalkyl, optionally substituted (cycloalkyl)alkyl, optionally substituted (heteroaryl)alkyl, optionally substituted (aryl)alkyl, optionally substituted aryl, optionally substituted heteroaryl having about 5 to 7 ring atoms and between 1 and 3 ring heteroatoms selected from N, O, and S, or optionally substituted (aryl)alkyl, wherein the aryl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from halogen, alkyl and alkoxy; and $R^2$ is optionally substituted indan-2-yl.

2. A compound or salt according to claim 1, of Formula III:

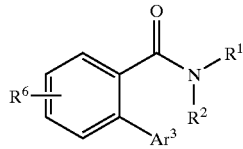

Formula III wherein:

Ar³ is imidazolyl, pyrrolyl, pyrazolyl, oxazolyl, thiazolyl or pyrimidinyl, each of which is substituted with from 0 to 3 substituents independently selected from halogen, hydroxy, amino, cyano, $C_1$–$C_4$alkyl, $C_1$–$C_4$alkoxy, mono- and di-($C_1$–$C_4$alkyl)amino, $C_1$–$C_2$haloalkyl, $C_1$–$C_2$haloalkoxy, $C_1$–$C_2$alkylthio, and —NHC(=O)$C_1$–$C_2$alkyl;

$R^6$ represents from 0 to 4 substituents independently selected from halogen, hydroxy, $C_1$–$C_4$alkyl, $C_1$–$C_4$alkoxy, $C_1$–$C_2$haloalkyl, $C_1$–$C_2$haloalkoxy, $C_1$–$C_2$alkylthio, and —NHC(=O) $C_1$–$C_2$ alkyl;

$R^1$ is:

i) (heteroaryl)$C_0$–$C_4$alkyl or (aryl) $C_0$–$C_4$alkyl, each of which is substituted with from 0 to 3 substituents independently selected from halogen, hydroxy, nitro, cyano, —COOH, —CONH₂, $C_1$–$C_4$ alkyl, $C_2$–$C_4$alkenyl, $C_2$–$C_4$alkynyl, $C_1$–$C_4$alkoxy, $C_1$–$C_4$alkylthio, —NC(=O)$C_1$–$C_2$alkyl, mono- and di($C_1$–$C_2$alkyl)amino, $C_2$–$C_3$alkanoyloxy, $C_1$–$C_3$alkoxycarbonyl, $C_1$–$C_2$haloalkyl, $C_1$–$C_2$haloalkoxy, thienyl, and phenyl; or ii) (aryl)$C_1$–$C_4$alkyl substituted with from 0 to 5 substituents independently chosen from halogen, hydroxy, $C_1$–$C_2$ alkyl, $C_1$–$C_2$ alkoxy, $C_1$–$C_2$haloalkyl, and $C_1$–$C_2$haloalkoxy, wherein the aryl portion is fused to a 5- to 7-membered saturated or partially unsaturated ring that (a) has 0, 1 or 2 ring atoms independently chosen from N, O and S, with remaining ring atoms being carbon, and (b) is substituted with from 0 to 2 substituents independently chosen from halogen, $C_1$–$C_4$alkyl and $C_1$–$C_4$alkoxy; and $R^2$ is indan-2-yl which is substituted with from 0 to 5 substituents independently selected from halogen, hydroxy, $C_1$–$C_4$ alkyl, $C_1$–$C_4$ alkoxy, $C_1$–$C_4$alkylthio, —NC(=O)$C_1$–$C_2$alkyl, $C_1$–$C_2$haloalkyl, $C_1$–$C_2$haloalkoxy, thienyl, and phenyl.

3. A compound according to claim 2, wherein $R^2$ is 2-indanyl substituted with from 0 to 2 substituents independently selected from halogen, $C_1$–$C_4$ alkyl, and $C_1$–$C_4$ alkoxy.

4. A compound or salt according to claim 2 of Formula II, wherein:

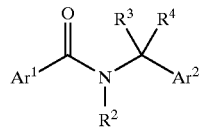

Formula II

Ar¹ is phenyl substituted with from 0 to 4 substituents independently selected from halogen, hydroxy, $C_1$–$C_4$alkyl, $C_1$–$C_4$alkoxy, $C_1$–$C_2$ haloalkyl, $C_1$–$C_2$ haloalkoxy, $C_1$–$C_2$alkylthio, and —NHC(=O) $C_1$–$C_2$ alkyl, and substituted at the 2-position relative to the point of attachment with imidazolyl, pyrrolyl, pyrazolyl, oxazoly, thiazolyl, or pyrimidinyl, each of which is substituted with from 0 to 3 substituents independently selected from halogen, amino, cyano, hydroxy, $C_1$–$C_4$alkyl, $C_1$–$C_4$alkoxy, $C_1$–$C_2$haloalkyl, $C_1$–$C_2$haloalkoxy, mono- and di-$C_1$–$C_4$alkylamino, $C_1$–$C_2$alkylthio, and —NHC(=O) $C_1$–$C_2$alkyl;

Ar² is selected from:
i) phenyl,
ii) naphthyl,
iii) a heterocycle having 1 or 2 rings, 3 to 8 atoms in each ring, and 1 to 3 heteroatoms independently selected from N, O, and S; and
iv) phenyl fused to a 5- to 7-membered saturated or partially unsaturated ring having 0, 1, or 2 ring atoms independently chosen from N, O, and S, with remaining ring atoms being carbon;

wherein each of i), ii), iii), and iv) is substituted with from 0 to 5 substituents independently selected from halogen, hydroxy, —COOH, —CONH₂, $C_1$–$C_4$alkyl, $C_1$–$C_4$alkoxy, $C_1$–$C_2$ haloalkyl, $C_1$–$C_2$ haloalkoxy, $C_1$–$C_2$ alkylthio, and —NHC(=O) $C_1$–$C_2$ alkyl;

$R^2$ is indan-2-yl which is substituted with from 0 to 3 substituents independently selected from halogen, hydroxy, $C_1$–$C_4$ alkyl, $C_1$–$C_4$alkoxy, $C_1$–$C_4$alkylthio, —NC(=O)$C_1$–$C_2$ alkyl, $C_1$–$C_2$ haloalkyl, $C_1$–$C_2$haloalkoxy, thienyl, and phenyl; and $R^3$ and $R^4$ are independently selected from hydrogen, $C_1$–$C_4$ alkyl, $C_2$–$C_4$alkenyl, and $C_2$–$C_4$alkynyl.

5. A compound or salt according to claim 2 wherein $R^2$ is 2-indanyl, substituted with from 0 to 2 substituents independently selected from chloro, fluoro, methyl and methoxy.

6. A compound according to claim 2, wherein $R^2$ is 2-indanyl which is substituted with from 0 to 2 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

7. A compound or salt according to claim 2 of Formula IV:

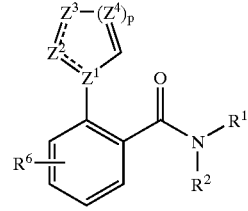

Formula IV wherein $Z^1$ is carbon or nitrogen;

$Z^2$, $Z^3$, and each occurrence of $Z^4$ are independently selected from $CR^7$, $NR^8$, and O such that each O ring atom, if any, is disposed between two $CR^7$ groups, p is an integer ranging from 1 to 2;

$R^6$ represents from 0 to 4 substituents independently selected from halogen, hydroxy, $C_1$–$C_4$alkyl, $C_1$–$C_4$alkoxy, $C_1$–$C_2$haloalkyl, $C_1$–$C_2$haloalkoxy, $C_1$–$C_2$ alkylthio, and —NHC(=O)$C_1$–$C_2$ alkyl;

$R^7$ is independently selected at each occurrence from hydrogen, halogen, hydroxy, amino, $C_1$–$C_6$alkyl, $C_1$–$C_6$alkoxy, $C_1$–$C_6$haloalkyl, $C_1$–$C_6$haloalkoxy, $C_2$–$C_6$alkenyl, $C_2$–$C_6$alkynyl, $C_3$–$C_8$cycloalkyl, mono- and di-($C_1$–$C_6$alkyl)amino, cyano, nitro, and $C_1$–$C_6$alkanoyl; and $R^8$ is independently selected at each occurrence from hydrogen, $C_1$–$C_6$alkyl, $C_1$–$C_6$haloalkyl, $C_2$–$C_6$alkenyl, $C_2$–$C_6$alkynyl, $C_3$–$C_8$cycloalkyl, and $C_1$–$C_6$alkanoyl.

8. A compound or salt according to claim 7 of Formula V:

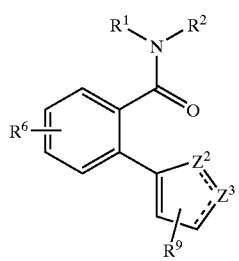

Formula V wherein one of $Z^2$ or $Z^3$ is oxygen; and $R^9$ represents from 0 to 3 substituents independently selected from hydrogen, fluoro, chloro, hydroxy, $C_1$–$C_6$alkyl, $C_1$–$C_6$alkoxy, $C_1$–$C_2$haloalkyl, and $C_1$–$C_6$haloalkoxy.

9. A compound or salt according claim 7 of Formula VI:

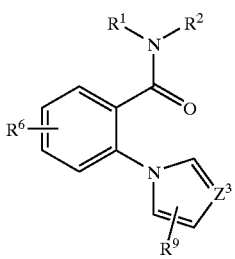

Formula VI wherein $Z^3$ is nitrogen or $CR^9$; and $R^9$ represents from 0 to 3 substituents independently selected from hydrogen, fluoro, chloro, hydroxy, $C_1$–$C_6$alkyl, $C_1$–$C_6$alkoxy, $C_1$–$C_2$haloalkyl, and $C_1$–$C_6$haloalkoxy.

10. A compound or salt according to claim 4 of Formula VII:

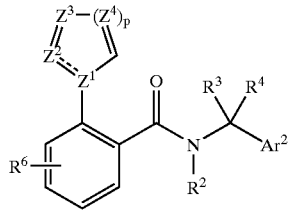

Formula VII wherein $Z^1$ is carbon or nitrogen;

$Z^2$, $Z^3$, and each occurrence of $Z^4$ are independently selected from $CR^7$, $NR^8$, and O such that each O ring atom, if any, is disposed between two $CR^7$ groups, p is an integer ranging from 1 to 2;

$R^6$ represents from 0 to 4 substituents independently selected from halogen, hydroxy, $C_1$–$C_4$alkyl, $C_1$–$C_4$alkoxy, $C_1$–$C_2$haloalkyl, $C_1$–$C_2$haloalkoxy, $C_1$–$C_2$ alkylthio, and —NHC(=O)$C_1$–$C_2$ alkyl;

$R^7$ is independently selected at each occurrence from hydrogen, halogen, hydroxy, amino, $C_1$–$C_6$alkyl, $C_1$–$C_6$alkoxy, $C_1$–$C_6$haloalkyl, $C_1$–$C_6$haloalkoxy, $C_2$–$C_6$alkenyl, $C_2$–$C_6$alkynyl, $C_3$–$C_8$cycloalkyl, mono- and di-($C_1$–$C_6$alkyl)amino, cyano, nitro, and $C_1$–$C_6$alkanoyl; and $R^8$ is independently selected at each occurrence from hydrogen, $C_1$–$C_6$alkyl, $C_1$–$C_6$haloalkyl, $C_2$–$C_6$alkenyl, $C_2$–$C_6$alkynyl, $C_3$–$C_8$cycloalkyl, and $C_1$–$C_6$alkanoyl.

11. A compound or salt according to claim 1 which is:

N-Indan-2-yl-N-(3-methyl-benzyl)-2-pyrrol-1-yl-benzamide;

N-(indan-2-yl)-N-(3-methylbenzyl)-2-(1H-pyrrol-1-yl)benzamide;

N-(indan-2-yl)-N-(4-methylbenzyl)-2-(1H-pyrrol-1-yl)benzamide;

N-Indan-2-yl-N-(4-methyl-benzyl)-2-pyrrol-1-yl-benzamide;

N-(4-chlorobenzyl)-N-(indan-2-yl)-2-(1H-pyrrol-1-yl)benzamide;

N-(indan-2-yl)-2-(1H-pyrrol-1-yl)-N-[4-(trifluoromethyl)benzyl]benzamide;

N-(indan-2-yl)-N-(3,5-dimethylbenzyl)-2-(1H-pyrrol-1-yl)benzamide;

N-(indan-2-yl)-N-(1-naphthylmethyl)-2-(1H-pyrrol-1-yl)benzamide;

N-(indan-2-yl)-N-(2-naphthylmethyl)-2-(1H-pyrrol-1-yl)benzamide;

or a pharmaceutically acceptable salt thereof.

12. A pharmaceutical composition comprising at least one compound or salt according to claim 1, or a prodrug or hydrate thereof, in combination with a physiologically acceptable carrier or excipient.

13. A method for treating a patient suffering from rheumatoid arthritis, psoriasis, or bronchial asthma comprising administering to the patient an effective amount of a compound according to claim 1.

14. A method for treating a patient suffering from ischemia-reperfusion injury comprising administering to the patient an effective amount of a compound according to claim 1.

15. A method for localizing C5a receptors in a tissue sample, comprising:

contacting the tissue sample containing C5a receptors with a radiolabeled compound according to claim 1 under conditions that permit binding of the compound to C5a receptors; and detecting the bound radiolabeled compound by autoradiography or scintillation counting.

16. A packaged pharmaceutical preparation, comprising:

(a) a pharmaceutical composition according to claim 12 in a container; and (b) instructions for using the composition to treat a patient suffering from rheumatoid arthritis, psoriasis, or bronchial asthma.

17. A packaged pharmaceutical preparation (a) a pharmaceutical composition according to claim 12 in a container; and (b) instructions for using the composition to treat or ischemia-reperfusion injury.

18. A pharmaceutical composition according to claim 12, wherein the pharmaceutical composition is formulated as an injectible fluid, an aerosol, a cream, a gel, a pill, a capsule, a syrup, or a transdermal patch.

19. A method for treating a patient suffeting from an autoimmune disorder, comprising administering to the patient an effective amount of a compound or salt according to claim 1.

20. A method for treating a patient suffering from an inflammatory disorder, comprising administering to the patient an effective amount of a compound or salt according to claim 1.

* * * * *